United States Patent
Pellegrino et al.

(10) Patent No.: US 12,059,193 B2
(45) Date of Patent: Aug. 13, 2024

(54) METHODS OF DENERVATING VERTEBRAL BODY USING EXTERNAL ENERGY SOURCE

(71) Applicant: Relievant Medsystems, Inc., Edina, MN (US)

(72) Inventors: Richard C. Pellegrino, Leesburg, VA (US); Rex Peters, San Jose, CA (US)

(73) Assignee: Relievant Medsystems, Inc., Redwood City, CA (US)

( * ) Notice: Subject to any disclaimer, the term of this patent is extended or adjusted under 35 U.S.C. 154(b) by 2 days.

(21) Appl. No.: 18/047,164

(22) Filed: Oct. 17, 2022

(65) Prior Publication Data

US 2023/0138303 A1    May 4, 2023

Related U.S. Application Data

(63) Continuation of application No. 16/205,050, filed on Nov. 29, 2018, now Pat. No. 11,471,210, which is a
(Continued)

(51) Int. Cl.
*A61B 18/14* (2006.01)
*A61B 17/02* (2006.01)
(Continued)

(52) U.S. Cl.
CPC ............ *A61B 18/14* (2013.01); *A61B 17/025* (2013.01); *A61B 18/1815* (2013.01); *A61F 7/00* (2013.01);
(Continued)

(58) Field of Classification Search
CPC ... A61B 18/14; A61B 17/025; A61B 18/1815; A61B 2017/0256; A61B 2018/00339;
(Continued)

(56) References Cited

U.S. PATENT DOCUMENTS 3,054,881 A    9/1962   Metz et al.
3,062,876 A    11/1962  Pons, Jr. et al.
(Continued)

FOREIGN PATENT DOCUMENTS

AU    2012244378 B2    5/2015
EP    0040658           12/1981
(Continued)

OTHER PUBLICATIONS

A Novel Approach for Treating Chronic Lower Back Pain Abstract for Presentation at North American Spine Society 26th Annual Meeting in Chicago IL on Nov. 4, 2011.
(Continued)

*Primary Examiner* — Alexei Bykhovski
(74) *Attorney, Agent, or Firm* — Nelson Mullins Riley & Scarborough LLP

(57) ABSTRACT

Systems and methods are disclosed for treating back pain associated with a vertebral body of a patient. The system may include an external energy source configured to be positioned at a location external to the body of the patient, a linear configured to drive translation of the external source in one or more axes, a computer coupled to the external source and linear drive and programming executable on said computer for determining a target treatment site within or near the vertebral body based on acquired imaging data, positioning a focal point of the external energy source to substantially coincide with the target treatment site, and delivering a treatment dose of therapeutic energy at said target treatment site, wherein the treatment dose is configured to modulate a nerve within or near the vertebral body.

20 Claims, 18 Drawing Sheets

Related U.S. Application Data continuation of application No. 14/369,661, filed as application No. PCT/US2012/071465 on Dec. 21, 2012, now Pat. No. 10,390,877.

(60) Provisional application No. 61/582,165, filed on Dec. 30, 2011, provisional application No. 61/582,170, filed on Dec. 30, 2011.

(51) Int. Cl.
| | |
|---|---|
| A61B 18/18 | (2006.01) |
| A61F 7/00 | (2006.01) |
| A61M 5/00 | (2006.01) |
| A61N 5/04 | (2006.01) |
| A61N 5/10 | (2006.01) |
| A61B 18/00 | (2006.01) |

(52) U.S. Cl.
CPC .............. *A61M 5/00* (2013.01); *A61N 5/045* (2013.01); *A61N 5/10* (2013.01); *A61N 5/1049* (2013.01); *A61B 2017/0256* (2013.01); *A61B 2018/00339* (2013.01); *A61B 2018/00577* (2013.01); *A61B 2018/00982* (2013.01)

(58) Field of Classification Search
CPC . A61B 2018/00577; A61B 2018/00982; A61F 7/00; A61M 5/00; A61N 5/045; A61N 5/10; A61N 5/1049
See application file for complete search history.

(56) References Cited

U.S. PATENT DOCUMENTS

| | | |
|---|---|---|
| 3,565,062 A | 2/1971 | Kuris |
| 3,822,708 A | 7/1974 | Zilber |
| 3,845,771 A | 11/1974 | Vise |
| 3,920,021 A | 11/1975 | Hiltebrandt |
| 3,938,502 A | 2/1976 | Bom |
| 3,997,408 A | 8/1976 | MacKew |
| 4,044,774 A | 8/1977 | Corgin et al. |
| 4,116,198 A | 9/1978 | Roos |
| 4,311,154 A | 1/1982 | Sterzer et al. |
| 4,312,364 A | 1/1982 | Convert et al. |
| 4,378,806 A | 4/1983 | Henley-Cohn |
| 4,448,198 A | 5/1984 | Turner |
| 4,449,528 A | 5/1984 | Auth et al. |
| 4,462,408 A | 7/1984 | Silverstein et al. |
| 4,528,979 A | 7/1985 | Marchenko et al. |
| 4,530,360 A | 7/1985 | Durate |
| 4,541,423 A | 9/1985 | Barber |
| 4,569,351 A | 2/1986 | Tang |
| 4,573,448 A | 3/1986 | Kambin |
| 4,586,512 A | 5/1986 | Do-huu |
| 4,601,296 A | 7/1986 | Yerushalmi |
| 4,612,940 A | 9/1986 | Kasevich et al. |
| 4,657,017 A | 4/1987 | Sorochenko |
| 4,662,383 A | 5/1987 | Sogawa et al. |
| 4,671,293 A | 6/1987 | Shalov |
| 4,676,258 A | 6/1987 | Inokuchi et al. |
| 4,679,561 A | 7/1987 | Doss |
| 4,681,122 A | 7/1987 | Winters et al. |
| 4,750,499 A | 6/1988 | Hoffer |
| 4,754,757 A | 7/1988 | Feucht |
| 4,757,820 A | 7/1988 | Itoh |
| 4,774,967 A | 10/1988 | Zanakis et al. |
| 4,800,899 A | 1/1989 | Elliott |
| 4,813,429 A | 3/1989 | Eshel et al. |
| 4,841,977 A | 6/1989 | Griffith et al. |
| 4,907,589 A | 3/1990 | Cosman |
| 4,924,863 A | 5/1990 | Sterzer |
| 4,936,281 A | 6/1990 | Stasz |
| 4,941,466 A | 7/1990 | Romano |
| 4,950,267 A | 8/1990 | Ishihara et al. |
| 4,951,677 A | 8/1990 | Crowley et al. |
| 4,955,377 A | 9/1990 | Lennox et al. |
| 4,959,063 A | 9/1990 | Kojima |
| 4,961,435 A | 10/1990 | Kitagawa et al. |
| 4,963,142 A | 10/1990 | Loertscher |
| 4,966,144 A | 10/1990 | Rochkind et al. |
| 4,967,765 A | 11/1990 | Turner et al. |
| 4,976,711 A | 12/1990 | Parins et al. |
| 4,977,902 A | 12/1990 | Sekino et al. |
| 5,000,185 A | 3/1991 | Yock |
| 5,002,058 A | 3/1991 | Marinelli |
| 5,002,059 A | 3/1991 | Crowley et al. |
| 5,007,437 A | 4/1991 | Sterzer |
| 5,025,778 A | 6/1991 | Silverstein et al. |
| 5,031,618 A | 7/1991 | Mullett |
| 5,061,266 A | 10/1991 | Hakky |
| 5,070,879 A | 12/1991 | Herres |
| RE33,791 E | 1/1992 | Carr |
| 5,078,736 A | 1/1992 | Behl |
| 5,080,660 A | 1/1992 | Buelna |
| 5,084,043 A | 1/1992 | Hertzmann et al. |
| 5,090,414 A | 2/1992 | Takano |
| 5,098,431 A | 3/1992 | Rydell |
| 5,106,376 A | 4/1992 | Mononen et al. |
| 5,108,404 A | 4/1992 | Scholten et al. |
| 5,131,397 A | 7/1992 | Crowley et al. |
| 5,147,355 A | 9/1992 | Friedman et al. |
| 5,156,157 A | 10/1992 | Valenta, Jr. et al. |
| 5,158,536 A | 10/1992 | Sekins et al. |
| 5,161,533 A | 11/1992 | Prass et al. |
| 5,167,231 A | 12/1992 | Matsui |
| 5,186,177 A | 2/1993 | O'Donnell et al. |
| 5,190,540 A | 3/1993 | Lee |
| 5,190,546 A | 3/1993 | Jervis |
| 5,201,729 A | 4/1993 | Hertzmann et al. |
| 5,207,672 A | 5/1993 | Martinelli et al. |
| 5,209,748 A | 5/1993 | Daikuzono |
| 5,222,953 A | 6/1993 | Dowlatsbabi |
| 5,226,430 A | 7/1993 | Spear et al. |
| 5,242,439 A | 9/1993 | Larsen et al. |
| 5,255,679 A | 10/1993 | Imran |
| 5,271,408 A | 12/1993 | Breyer et al. |
| 5,273,026 A | 12/1993 | Wilk |
| 5,281,213 A | 1/1994 | Milder et al. |
| 5,281,215 A | 1/1994 | Milder et al. |
| 5,282,468 A | 2/1994 | Klepinski |
| 5,292,321 A | 3/1994 | Lee |
| 5,295,484 A | 3/1994 | Marcus et al. |
| 5,300,085 A | 4/1994 | Yock |
| 5,304,214 A | 4/1994 | DeFord et al. |
| 5,305,756 A | 4/1994 | Entrekin et al. |
| 5,314,463 A | 5/1994 | Camps et al. |
| 5,320,617 A | 6/1994 | Leach |
| 5,324,255 A | 6/1994 | Pasafaro et al. |
| 5,325,860 A | 7/1994 | Seward et al. |
| 5,342,292 A | 8/1994 | Nita et al. |
| 5,342,357 A | 8/1994 | Nardella |
| 5,342,409 A | 8/1994 | Mullett |
| 5,344,435 A | 9/1994 | Turner et al. |
| 5,345,940 A | 9/1994 | Seward et al. |
| 5,348,554 A | 9/1994 | Imran et al. |
| 5,350,377 A | 9/1994 | Winston et al. |
| 5,351,691 A | 10/1994 | Brommersma |
| 5,366,443 A | 11/1994 | Eggers et al. |
| 5,366,490 A | 11/1994 | Edwards et al. |
| 5,368,031 A | 11/1994 | Cline et al. |
| 5,368,035 A | 11/1994 | Hamm et al. |
| 5,368,557 A | 11/1994 | Nita et al. |
| 5,368,558 A | 11/1994 | Nita |
| 5,370,675 A | 12/1994 | Edwards et al. |
| 5,370,678 A | 12/1994 | Edwards et al. |
| 5,372,138 A | 12/1994 | Crowley et al. |
| 5,374,265 A | 12/1994 | Sand |
| 5,383,876 A | 1/1995 | Nardella |
| 5,385,148 A | 1/1995 | Lesh et al. |
| 5,385,544 A | 1/1995 | Edwards et al. |
| 5,391,197 A | 2/1995 | Burdette et al. |
| 5,391,199 A | 2/1995 | Ben-Haim |
| 5,405,376 A | 4/1995 | Mulier et al. |

(56) References Cited

U.S. PATENT DOCUMENTS

| | | |
|---|---|---|
| 5,411,527 A | 5/1995 | Alt |
| 5,417,719 A | 5/1995 | Hull et al. |
| 5,419,767 A | 5/1995 | Eggers et al. |
| 5,421,338 A | 6/1995 | Crowley |
| 5,423,811 A | 6/1995 | Imran et al. |
| 5,431,649 A | 7/1995 | Mulier et al. |
| 5,433,739 A | 7/1995 | Sluijter et al. |
| D361,555 S | 8/1995 | Bettin et al. |
| 5,437,661 A | 8/1995 | Rieser |
| 5,441,499 A | 8/1995 | Fritzsch |
| 5,441,527 A | 8/1995 | Erickson et al. |
| 5,443,463 A | 8/1995 | Stern et al. |
| 5,447,509 A | 9/1995 | Millis et al. |
| 5,449,380 A | 9/1995 | Chin |
| 5,454,373 A | 10/1995 | Koger et al. |
| 5,458,596 A | 10/1995 | Lax et al. |
| 5,458,597 A | 10/1995 | Edwards et al. |
| 5,471,988 A | 12/1995 | Fujio et al. |
| 5,472,441 A | 12/1995 | Edwards et al. |
| 5,474,530 A | 12/1995 | Passafaro et al. |
| 5,484,432 A | 1/1996 | Sand |
| 5,486,170 A | 1/1996 | Winston et al. |
| 5,501,703 A | 3/1996 | Holsheimer et al. |
| 5,505,730 A | 4/1996 | Edwarrds |
| 5,514,130 A | 5/1996 | Baker |
| 5,524,624 A | 6/1996 | Tepper et al. |
| 5,526,815 A | 6/1996 | Granz et al. |
| 5,529,580 A | 6/1996 | Hagino et al. |
| 5,540,679 A | 7/1996 | Fram et al. |
| 5,540,681 A | 7/1996 | Strul et al. |
| 5,540,684 A | 7/1996 | Hassler, Jr. |
| 5,545,161 A | 8/1996 | Imran |
| 5,560,362 A | 10/1996 | Silwa, Jr. et al. |
| 5,565,005 A | 10/1996 | Erickson et al. |
| 5,569,242 A | 10/1996 | Lax et al. |
| 5,571,088 A | 11/1996 | Lennox et al. |
| 5,571,147 A | 11/1996 | Sluijter et al. |
| 5,575,772 A | 11/1996 | Lennox |
| 5,575,788 A | 11/1996 | Baker et al. |
| 5,588,432 A | 12/1996 | Crowley |
| 5,596,988 A | 1/1997 | Markle et al. |
| 5,601,526 A | 2/1997 | Chapelon et al. |
| 5,606,974 A | 3/1997 | Castellano et al. |
| 5,609,151 A | 3/1997 | Mulier et al. |
| 5,620,479 A | 4/1997 | Diederich |
| 5,628,317 A | 5/1997 | Starkebaum et al. |
| 5,630,426 A | 5/1997 | Shmulewitz et al. |
| 5,630,837 A | 5/1997 | Crowley |
| 5,643,319 A | 7/1997 | Green et al. |
| 5,643,330 A | 7/1997 | Holshiemer et al. |
| 5,647,361 A | 7/1997 | Damadian |
| 5,647,871 A | 7/1997 | Levine et al. |
| 5,658,278 A | 8/1997 | Imran et al. |
| 5,672,173 A | 9/1997 | Gough et al. |
| 5,681,282 A | 10/1997 | Eggers et al. |
| 5,683,366 A | 11/1997 | Eggers et al. |
| 5,685,839 A | 11/1997 | Baker et al. |
| 5,687,729 A | 11/1997 | Schaetzle |
| 5,688,267 A | 11/1997 | Panescu |
| 5,693,052 A | 12/1997 | Weaver |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,697,927 A | 12/1997 | Imran et al. |
| 5,700,262 A | 12/1997 | Acosta et al. |
| 5,718,231 A | 2/1998 | Chen et al. |
| 5,720,286 A | 2/1998 | Chapelon et al. |
| 5,720,287 A | 2/1998 | Chapelon et al. |
| 5,722,403 A | 3/1998 | McGee et al. |
| 5,725,494 A | 3/1998 | Brisken |
| 5,728,062 A | 3/1998 | Brisken |
| 5,730,706 A | 3/1998 | Gamies |
| 5,733,315 A | 3/1998 | Burdette et al. |
| 5,735,280 A | 4/1998 | Sherman et al. |
| 5,735,811 A | 4/1998 | Brisken |
| 5,735,846 A | 4/1998 | Fleischman et al. |
| 5,735,847 A | 4/1998 | Gough et al. |
| 5,738,680 A | 4/1998 | Mueller et al. |
| 5,741,249 A | 4/1998 | Moss et al. |
| 5,743,904 A | 4/1998 | Edwards |
| 5,746,737 A | 5/1998 | Saadat |
| 5,752,969 A | 5/1998 | Cunci et al. |
| 5,755,663 A | 5/1998 | Johnson et al. |
| 5,762,066 A | 6/1998 | Law et al. |
| 5,762,616 A | 6/1998 | Talish |
| 5,766,153 A | 6/1998 | Eggers et al. |
| 5,766,231 A | 6/1998 | Erickson et al. |
| 5,776,092 A | 7/1998 | Farin et al. |
| 5,785,705 A | 7/1998 | Baker |
| 5,800,378 A | 9/1998 | Edwards et al. |
| 5,800,429 A | 9/1998 | Edwards |
| 5,800,432 A | 9/1998 | Swanson |
| 5,807,237 A | 9/1998 | Tindel |
| 5,807,391 A | 9/1998 | Wijkamp |
| 5,807,392 A | 9/1998 | Eggers |
| 5,807,395 A | 9/1998 | Mulier et al. |
| 5,810,764 A | 9/1998 | Eggers et al. |
| 5,817,021 A | 10/1998 | Reichenberger |
| 5,824,021 A | 10/1998 | Rise |
| 5,840,031 A | 11/1998 | Crowley |
| 5,843,019 A | 12/1998 | Eggers et al. |
| 5,843,021 A | 12/1998 | Edwards et al. |
| 5,844,092 A | 12/1998 | Presta et al. |
| 5,846,218 A | 12/1998 | Brisken et al. |
| 5,849,011 A | 12/1998 | Jones et al. |
| 5,855,576 A | 1/1999 | LeVeen et al. |
| 5,860,951 A | 1/1999 | Eggers et al. |
| 5,865,788 A | 2/1999 | Edwards et al. |
| 5,865,801 A | 2/1999 | Houser |
| 5,868,740 A | 2/1999 | LeVeen et al. |
| 5,871,469 A | 2/1999 | Eggers et al. |
| 5,871,470 A | 2/1999 | McWha |
| 5,871,481 A | 2/1999 | Kannenberg et al. |
| 5,873,855 A | 2/1999 | Eggers et al. |
| 5,873,877 A | 2/1999 | McGaffigan et al. |
| 5,876,398 A | 3/1999 | Mulier et al. |
| 5,888,198 A | 3/1999 | Eggers et al. |
| 5,891,095 A | 4/1999 | Eggers et al. |
| 5,895,370 A | 4/1999 | Edwards et al. |
| 5,902,272 A | 5/1999 | Eggers et al. |
| 5,902,308 A | 5/1999 | Murphy |
| 5,904,681 A | 5/1999 | West, Jr. |
| 5,906,613 A | 5/1999 | Mulier et al. |
| 5,916,213 A | 6/1999 | Haissaguerre et al. |
| 5,916,214 A | 6/1999 | Cosio |
| 5,919,188 A | 7/1999 | Shearon et al. |
| 5,931,805 A | 8/1999 | Brisken |
| 5,935,123 A | 8/1999 | Edwards et al. |
| 5,938,582 A | 8/1999 | Ciamacco et al. |
| 5,941,722 A | 8/1999 | Chen |
| 5,941,876 A | 8/1999 | Nardella et al. |
| 5,944,715 A | 8/1999 | Goble et al. |
| 5,948,007 A | 9/1999 | Starkebaum et al. |
| 5,948,008 A | 9/1999 | Daikuzono |
| 5,954,716 A | 9/1999 | Sharkey et al. |
| 5,964,727 A | 10/1999 | Edwards et al. |
| 5,967,988 A | 10/1999 | Briscoe et al. |
| 5,972,015 A | 10/1999 | Scribner et al. |
| 5,976,105 A | 11/1999 | Marcove et al. |
| 5,983,141 A | 11/1999 | Sluijter et al. |
| 5,997,497 A | 12/1999 | Nita et al. |
| 6,001,095 A | 12/1999 | de la Rama et al. |
| 6,007,533 A | 12/1999 | Casscells et al. |
| 6,007,570 A | 12/1999 | Sharkey et al. |
| 6,012,457 A | 1/2000 | Lesh |
| 6,014,588 A | 1/2000 | Fitz |
| 6,016,452 A | 1/2000 | Kasevich |
| 6,016,809 A | 1/2000 | Mulier et al. |
| 6,017,356 A | 1/2000 | Frederick et al. |
| 6,019,776 A | 2/2000 | Preissman et al. |
| 6,022,334 A | 2/2000 | Edwards et al. |
| 6,024,733 A | 2/2000 | Eggers et al. |
| 6,024,740 A | 2/2000 | Lesh et al. |

(56) References Cited

U.S. PATENT DOCUMENTS

| | | |
|---|---|---|
| 6,030,374 A | 2/2000 | McDaniel |
| 6,030,402 A | 2/2000 | Thompson et al. |
| 6,032,673 A | 3/2000 | Langberg et al. |
| 6,032,674 A | 3/2000 | Eggers et al. |
| 6,033,411 A | 3/2000 | Preissman et al. |
| 6,035,238 A | 3/2000 | Ingle et al. |
| 6,038,480 A | 3/2000 | Hrdlicka et al. |
| 6,045,532 A | 4/2000 | Eggers et al. |
| 6,046,187 A | 4/2000 | Berde et al. |
| 6,047,214 A | 4/2000 | Mueller et al. |
| 6,050,995 A | 4/2000 | Durgin |
| 6,053,172 A | 4/2000 | Hovda et al. |
| 6,053,909 A | 4/2000 | Shadduck |
| 6,056,745 A | 5/2000 | Panescu et al. |
| 6,063,078 A | 5/2000 | Wittkampf |
| 6,063,079 A | 5/2000 | Hovda et al. |
| 6,066,134 A | 5/2000 | Eggers et al. |
| 6,066,139 A | 5/2000 | Ryan et al. |
| 6,068,642 A | 5/2000 | Johnson et al. |
| 6,071,279 A | 6/2000 | Whayne et al. |
| 6,073,051 A | 6/2000 | Sharkey et al. |
| 6,074,352 A | 6/2000 | Hynynen et al. |
| 6,086,585 A | 7/2000 | Hovda et al. |
| 6,090,105 A | 7/2000 | Zepeda et al. |
| 6,095,149 A | 8/2000 | Sharkey et al. |
| 6,099,499 A | 8/2000 | Ciamacco |
| 6,099,514 A | 8/2000 | Sharkey et al. |
| 6,099,524 A | 8/2000 | Lipson et al. |
| 6,102,046 A | 8/2000 | Weinstein et al. |
| 6,104,957 A | 8/2000 | Alo et al. |
| 6,105,581 A | 8/2000 | Eggers et al. |
| 6,106,454 A | 8/2000 | Berg et al. |
| 6,109,268 A | 8/2000 | Thapliyal et al. |
| 6,112,122 A | 8/2000 | Schwardt et al. |
| 6,113,597 A | 9/2000 | Eggers et al. |
| 6,117,101 A | 9/2000 | Diederich et al. |
| 6,117,109 A | 9/2000 | Eggers et al. |
| 6,117,128 A | 9/2000 | Gregory |
| 6,120,467 A | 9/2000 | Schallhorn |
| 6,120,502 A | 9/2000 | Michelson |
| 6,122,549 A | 9/2000 | Sharkey et al. |
| 6,126,682 A | 10/2000 | Ashley et al. |
| 6,137,209 A | 10/2000 | Dahlberg et al. |
| 6,139,545 A | 10/2000 | Utley et al. |
| 6,142,992 A | 11/2000 | Cheng et al. |
| 6,143,019 A | 11/2000 | Motamedi et al. |
| 6,146,380 A | 11/2000 | Racz et al. |
| 6,149,620 A | 11/2000 | Baker et al. |
| 6,159,194 A | 12/2000 | Eggers et al. |
| 6,159,208 A | 12/2000 | Hovda et al. |
| 6,161,048 A | 12/2000 | Sluijter et al. |
| 6,164,283 A | 12/2000 | Lesh |
| 6,165,172 A | 12/2000 | Farley et al. |
| 6,168,593 B1 | 1/2001 | Sharkey et al. |
| 6,169,924 B1 | 1/2001 | Meloy et al. |
| 6,171,239 B1 | 1/2001 | Humphrey |
| 6,176,857 B1 | 1/2001 | Ashley |
| 6,179,824 B1 | 1/2001 | Eggers et al. |
| 6,179,836 B1 | 1/2001 | Eggers et al. |
| 6,179,858 B1 | 1/2001 | Squire et al. |
| 6,183,469 B1 | 2/2001 | Thapliyal et al. |
| 6,190,381 B1 | 2/2001 | Olsen et al. |
| 6,190,383 B1 | 2/2001 | Schmaltz et al. |
| 6,193,715 B1 | 2/2001 | Wrublewski et al. |
| 6,203,542 B1 | 3/2001 | Ellsberry et al. |
| 6,206,842 B1 | 3/2001 | Tu et al. |
| 6,210,393 B1 | 4/2001 | Brisken |
| 6,210,402 B1 | 4/2001 | Olsen et al. |
| 6,210,415 B1 | 4/2001 | Bester |
| 6,216,704 B1 | 4/2001 | Ingle et al. |
| 6,221,038 B1 | 4/2001 | Brisken |
| 6,224,592 B1 | 5/2001 | Eggers et al. |
| 6,228,046 B1 | 5/2001 | Brisken |
| 6,228,078 B1 | 5/2001 | Eggers et al. |
| 6,228,082 B1 | 5/2001 | Baker et al. |
| 6,231,516 B1 | 5/2001 | Keilman et al. |
| 6,231,528 B1 | 5/2001 | Kaufman et al. |
| 6,231,571 B1 | 5/2001 | Ellman et al. |
| 6,231,615 B1 | 5/2001 | Preissman |
| 6,233,488 B1 | 5/2001 | Hess |
| 6,235,020 B1 | 5/2001 | Cheng et al. |
| 6,235,022 B1 | 5/2001 | Hallock et al. |
| 6,235,024 B1 | 5/2001 | Tu |
| 6,237,604 B1 | 5/2001 | Burnside et al. |
| 6,238,391 B1 | 5/2001 | Olsen et al. |
| 6,238,393 B1 | 5/2001 | Mulier et al. |
| 6,241,665 B1 | 6/2001 | Negus et al. |
| 6,241,725 B1 | 6/2001 | Cosman |
| 6,241,734 B1 | 6/2001 | Scribner et al. |
| 6,245,064 B1 | 6/2001 | Lesh et al. |
| 6,246,912 B1 | 6/2001 | Sluijter et al. |
| 6,248,110 B1 | 6/2001 | Reiley et al. |
| 6,248,345 B1 | 6/2001 | Goldenheim et al. |
| 6,254,553 B1 | 7/2001 | Lidgren et al. |
| 6,254,599 B1 | 7/2001 | Lesh et al. |
| 6,254,600 B1 | 7/2001 | Willink et al. |
| 6,258,086 B1 | 7/2001 | Ashley et al. |
| 6,259,952 B1 | 7/2001 | Sluijter |
| 6,261,311 B1 | 7/2001 | Sharkey et al. |
| 6,264,650 B1 | 7/2001 | Hovda et al. |
| 6,264,651 B1 | 7/2001 | Underwood et al. |
| 6,264,652 B1 | 7/2001 | Eggers et al. |
| 6,264,659 B1 | 7/2001 | Ross et al. |
| 6,267,770 B1 | 7/2001 | Truwit |
| 6,270,498 B1 | 8/2001 | Michelson |
| 6,277,112 B1 | 8/2001 | Underwood et al. |
| 6,277,122 B1 | 8/2001 | McGahan et al. |
| 6,280,441 B1 | 8/2001 | Ryan |
| 6,280,456 B1 | 8/2001 | Scribner et al. |
| 6,283,961 B1 | 9/2001 | Underwood et al. |
| 6,287,114 B1 | 9/2001 | Meller et al. |
| 6,287,272 B1 | 9/2001 | Brisken et al. |
| 6,287,304 B1 | 9/2001 | Eggers et al. |
| 6,290,715 B1 | 9/2001 | Sharkey et al. |
| 6,292,699 B1 | 9/2001 | Simon et al. |
| 6,296,619 B1 | 10/2001 | Brisken et al. |
| 6,296,636 B1 | 10/2001 | Cheng et al. |
| 6,296,638 B1 | 10/2001 | Davison et al. |
| 6,305,378 B1 | 10/2001 | Lesh et al. |
| 6,309,387 B1 | 10/2001 | Eggers et al. |
| 6,309,420 B1 | 10/2001 | Preissman |
| 6,312,408 B1 | 11/2001 | Eggers et al. |
| 6,312,425 B1 | 11/2001 | Simpson et al. |
| 6,312,426 B1 | 11/2001 | Goldberg et al. |
| 6,319,241 B1 | 11/2001 | King et al. |
| 6,322,549 B1 | 11/2001 | Eggers et al. |
| 6,348,055 B1 | 2/2002 | Preissman |
| 6,355,032 B1 | 3/2002 | Hovda et al. |
| 6,356,790 B1 | 3/2002 | Maguire et al. |
| 6,361,531 B1 | 3/2002 | Hissong |
| 6,363,937 B1 | 4/2002 | Hovda et al. |
| 6,368,292 B1 | 4/2002 | Ogden et al. |
| 6,379,351 B1 | 4/2002 | Thapliyal et al. |
| 6,383,190 B1 | 5/2002 | Preissman |
| 6,391,025 B1 | 5/2002 | Weinstein et al. |
| 6,398,782 B1 | 6/2002 | Pecor et al. |
| 6,416,507 B1 | 7/2002 | Eggers et al. |
| 6,416,508 B1 | 7/2002 | Eggers et al. |
| 6,423,057 B1 | 7/2002 | He et al. |
| 6,423,059 B1 | 7/2002 | Hanson et al. |
| 6,425,887 B1 | 7/2002 | McGuckin et al. |
| 6,426,339 B1 | 7/2002 | Berde et al. |
| 6,428,491 B1 | 8/2002 | Weiss |
| 6,432,103 B1 | 8/2002 | Ellsberry et al. |
| 6,436,060 B1 | 8/2002 | Talish |
| 6,436,098 B1 | 8/2002 | Michelson |
| 6,440,138 B1 | 8/2002 | Reiley et al. |
| 6,447,448 B1 | 9/2002 | Ishikawa et al. |
| 6,451,013 B1 | 9/2002 | Bays et al. |
| 6,454,727 B1 | 9/2002 | Burbank et al. |
| 6,461,350 B1 | 10/2002 | Underwood et al. |
| 6,461,354 B1 | 10/2002 | Olsen et al. |
| 6,464,695 B2 | 10/2002 | Hovda et al. |
| 6,468,270 B1 | 10/2002 | Hovda et al. |

(56) References Cited

U.S. PATENT DOCUMENTS

| | | |
|---|---|---|
| 6,468,274 B1 | 10/2002 | Alleyne et al. |
| 6,470,220 B1 | 10/2002 | Kraus et al. |
| 6,478,793 B1 | 11/2002 | Cosman et al. |
| 6,482,201 B1 | 11/2002 | Olsen et al. |
| 6,485,271 B1 | 11/2002 | Tack |
| 6,487,446 B1 | 11/2002 | Hill et al. |
| 6,491,893 B1 | 12/2002 | Babich |
| 6,493,592 B1 | 12/2002 | Leonard et al. |
| 6,494,902 B2 | 12/2002 | Hoey et al. |
| 6,500,173 B2 | 12/2002 | Underwood et al. |
| 6,505,075 B1 | 1/2003 | Weiner |
| 6,508,839 B1 | 1/2003 | Lambrecht et al. |
| 6,524,261 B2 | 2/2003 | Talish et al. |
| 6,527,759 B1 | 3/2003 | Tachibana et al. |
| 6,537,306 B1 | 3/2003 | Burdette et al. |
| 6,540,741 B1 | 4/2003 | Underwood et al. |
| 6,544,261 B2 | 4/2003 | Ellsberry et al. |
| 6,557,559 B1 | 5/2003 | Eggers et al. |
| 6,558,385 B1 | 5/2003 | McClurken et al. |
| 6,558,390 B2 | 5/2003 | Cragg |
| 6,560,486 B1 | 5/2003 | Osorio et al. |
| 6,562,033 B2 | 5/2003 | Shah et al. |
| 6,575,919 B1 | 6/2003 | Reiley et al. |
| 6,575,968 B1 | 6/2003 | Eggers et al. |
| 6,575,969 B1 | 6/2003 | Rittman, III et al. |
| 6,575,979 B1 | 6/2003 | Cragg |
| 6,578,579 B2 | 6/2003 | Burnside et al. |
| 6,582,423 B1 | 6/2003 | Thapliyal et al. |
| 6,585,656 B2 | 7/2003 | Masters |
| 6,589,237 B2 | 7/2003 | Woloszko et al. |
| 6,592,559 B1 | 7/2003 | Pakter et al. |
| 6,595,990 B1 | 7/2003 | Weinstein et al. |
| 6,599,288 B2 | 7/2003 | Maguire et al. |
| 6,602,248 B1 | 8/2003 | Sharps et al. |
| 6,604,003 B2 | 8/2003 | Fredricks et al. |
| 6,607,502 B1 | 8/2003 | Maguire et al. |
| 6,607,529 B1 | 8/2003 | Jones et al. |
| 6,608,502 B2 | 8/2003 | Aoki et al. |
| 6,622,731 B2 | 9/2003 | Daniel et al. |
| 6,623,505 B2 | 9/2003 | Scribner et al. |
| 6,632,193 B1 | 10/2003 | Davison et al. |
| 6,632,220 B1 | 10/2003 | Eggers et al. |
| 6,645,202 B1 | 11/2003 | Pless et al. |
| 6,648,883 B2 | 11/2003 | Francischelli et al. |
| 6,651,669 B1 | 11/2003 | Burnside |
| 6,659,106 B1 | 12/2003 | Hovda et al. |
| 6,663,627 B2 | 12/2003 | Francischelli et al. |
| 6,663,647 B2 | 12/2003 | Reiley et al. |
| 6,673,063 B2 | 1/2004 | Brett |
| 6,689,086 B1 | 2/2004 | Nita et al. |
| 6,689,125 B1 | 2/2004 | Keith et al. |
| 6,692,450 B1 | 2/2004 | Coleman |
| 6,699,240 B2 | 3/2004 | Francischelli |
| 6,699,242 B2 | 3/2004 | Heggeness |
| 6,709,432 B2 | 3/2004 | Ferek-Patric |
| 6,718,208 B2 | 4/2004 | Hill et al. |
| 6,719,761 B1 | 4/2004 | Reiley et al. |
| 6,723,087 B2 | 4/2004 | O'Neill et al. |
| 6,723,094 B1 | 4/2004 | Desinger |
| 6,726,684 B1 | 4/2004 | Woloszko et al. |
| 6,736,810 B2 | 5/2004 | Hoey et al. |
| 6,736,835 B2 | 5/2004 | Pellegrino et al. |
| 6,745,079 B2 | 6/2004 | King |
| 6,746,447 B2 | 6/2004 | Davison et al. |
| 6,746,451 B2 | 6/2004 | Middleton et al. |
| 6,749,604 B1 | 6/2004 | Eggers et al. |
| 6,758,846 B2 | 7/2004 | Goble et al. |
| 6,770,071 B2 | 8/2004 | Woloszko et al. |
| 6,772,012 B2 | 8/2004 | Ricart et al. |
| 6,773,431 B2 | 8/2004 | Eggers et al. |
| 6,795,737 B2 | 9/2004 | Gielen et al. |
| 6,805,697 B1 | 10/2004 | Helm et al. |
| 6,827,715 B2 | 12/2004 | Francischelli et al. |
| 6,827,716 B2 | 12/2004 | Ryan et al. |
| 6,832,996 B2 | 12/2004 | Woloszko et al. |
| 6,837,887 B2 | 1/2005 | Woloszko et al. |
| 6,837,888 B2 | 1/2005 | Ciarrocca et al. |
| 6,852,091 B2 | 2/2005 | Edwards et al. |
| 6,863,672 B2 | 3/2005 | Reiley et al. |
| 6,875,219 B2 | 4/2005 | Arramon et al. |
| 6,881,214 B2 | 4/2005 | Cosman et al. |
| 6,896,674 B1 | 5/2005 | Woloszko et al. |
| 6,896,675 B2 | 5/2005 | Leung et al. |
| 6,907,884 B2 | 6/2005 | Pellegrino et al. |
| 6,915,806 B2 | 7/2005 | Pacek et al. |
| 6,922,579 B2 | 7/2005 | Taimisto et al. |
| 6,923,813 B2 | 8/2005 | Phillips et al. |
| 6,936,046 B2 | 8/2005 | Hissong et al. |
| 6,955,674 B2 | 10/2005 | Eick et al. |
| 6,960,204 B2 | 11/2005 | Eggers et al. |
| 6,962,589 B2 | 11/2005 | Mulier et al. |
| 6,974,453 B2 | 12/2005 | Woloszko et al. |
| 6,980,849 B2 | 12/2005 | Sasso |
| 6,981,981 B2 | 1/2006 | Reiley et al. |
| 6,989,010 B2 | 1/2006 | Francischelli et al. |
| 6,997,941 B2 | 2/2006 | Sharkey et al. |
| 7,001,383 B2 | 2/2006 | Keidar |
| 7,041,096 B2 | 5/2006 | Malis et al. |
| 7,044,954 B2 | 5/2006 | Reiley et al. |
| 7,048,743 B2 | 5/2006 | Miller et al. |
| 7,065,408 B2 | 6/2006 | Herman et al. |
| 7,081,122 B1 | 7/2006 | Reiley et al. |
| 7,090,672 B2 | 8/2006 | Underwood et al. |
| 7,094,215 B2 | 8/2006 | Davison et al. |
| 7,104,989 B2 | 9/2006 | Skarda |
| 7,118,574 B2 | 10/2006 | Patel et al. |
| 7,131,969 B1 | 11/2006 | Hovda et al. |
| 7,153,307 B2 | 12/2006 | Scribner et al. |
| 7,163,536 B2 | 1/2007 | Godara |
| 7,177,678 B1 | 2/2007 | Osorio et al. |
| 7,179,255 B2 | 2/2007 | Lettice et al. |
| 7,186,234 B2 | 3/2007 | Dahla et al. |
| 7,192,428 B2 | 3/2007 | Eggers et al. |
| 7,201,731 B1 | 4/2007 | Lundquist et al. |
| 7,201,750 B1 | 4/2007 | Eggers et al. |
| 7,211,055 B2 | 5/2007 | Diederich et al. |
| 7,217,268 B2 | 5/2007 | Eggers et al. |
| 7,238,184 B2 | 7/2007 | Megerman et al. |
| 7,241,297 B2 | 7/2007 | Shaolian et al. |
| 7,250,048 B2 | 7/2007 | Francischelli et al. |
| 7,258,690 B2 | 8/2007 | Sutton et al. |
| 7,270,659 B2 | 9/2007 | Ricart et al. |
| 7,270,661 B2 | 9/2007 | Dahla et al. |
| 7,276,063 B2 | 10/2007 | Davison et al. |
| 7,294,127 B2 | 11/2007 | Leung et al. |
| 7,305,264 B2 | 12/2007 | Larson et al. |
| 7,306,596 B2 | 12/2007 | Hillier et al. |
| 7,306,598 B2 | 12/2007 | Truckai et al. |
| 7,318,823 B2 | 1/2008 | Sharps et al. |
| 7,318,826 B2 | 1/2008 | Teitelbaum et al. |
| 7,326,203 B2 | 2/2008 | Papineau et al. |
| 7,331,956 B2 | 2/2008 | Hovda et al. |
| 7,331,957 B2 | 2/2008 | Woloszko et al. |
| RE40,156 E | 3/2008 | Sharps et al. |
| 7,346,391 B1 | 3/2008 | Osorio et al. |
| 7,386,350 B2 | 6/2008 | Vilims |
| 7,387,625 B2 | 6/2008 | Hovda et al. |
| 7,393,351 B2 | 7/2008 | Woloszko et al. |
| 7,399,306 B2 | 7/2008 | Reiley et al. |
| 7,422,585 B1 | 9/2008 | Eggers et al. |
| 7,429,262 B2 | 9/2008 | Woloszko et al. |
| 7,435,247 B2 | 10/2008 | Woloszko et al. |
| 7,435,250 B2 | 10/2008 | Francischelli et al. |
| 7,442,191 B2 | 10/2008 | Hovda et al. |
| 7,468,059 B2 | 12/2008 | Eggers et al. |
| 7,480,533 B2 | 1/2009 | Cosman et al. |
| 7,502,652 B2 | 3/2009 | Gaunt et al. |
| 7,503,920 B2 | 3/2009 | Siegal |
| 7,503,921 B2 | 3/2009 | Siegal |
| 7,507,236 B2 | 3/2009 | Eggers et al. |
| 7,546,164 B2 | 6/2009 | King |
| 7,553,307 B2 | 6/2009 | Bleich et al. |
| 7,553,309 B2 | 6/2009 | Buysse et al. |
| 7,555,343 B2 | 6/2009 | Bleich |

(56) References Cited

U.S. PATENT DOCUMENTS

| | | |
|---|---|---|
| 7,559,932 B2 | 7/2009 | Truckai et al. |
| 7,569,626 B2 | 8/2009 | Truckai |
| 7,574,257 B2 | 8/2009 | Rittman, III |
| 7,585,300 B2 | 9/2009 | Cha |
| 7,593,778 B2 | 9/2009 | Chandran et al. |
| 7,594,913 B2 | 9/2009 | Ormsby et al. |
| 7,604,636 B1 | 10/2009 | Walters et al. |
| 7,621,952 B2 | 11/2009 | Truckai et al. |
| 7,645,277 B2 | 1/2010 | McClurken et al. |
| 7,678,111 B2 | 3/2010 | Mulier et al. |
| 7,678,116 B2 | 3/2010 | Truckai et al. |
| 7,682,378 B2 | 3/2010 | Truckai et al. |
| 7,708,733 B2 | 5/2010 | Sanders et al. |
| 7,717,918 B2 | 5/2010 | Truckai et al. |
| 7,722,620 B2 | 5/2010 | Truckai et al. |
| 7,731,720 B2 | 6/2010 | Sand et al. |
| 7,738,968 B2 | 6/2010 | Bleich |
| 7,740,631 B2 | 6/2010 | Bleich et al. |
| 7,749,218 B2 | 7/2010 | Pellegrino et al. |
| 7,749,220 B2 | 7/2010 | Schmaltz et al. |
| 7,780,733 B2 | 8/2010 | Carver et al. |
| 7,792,588 B2 | 9/2010 | Harding |
| 7,799,021 B2 | 9/2010 | Leung et al. |
| 7,819,826 B2 | 10/2010 | Diederich et al. |
| 7,819,869 B2 | 10/2010 | Godara et al. |
| 7,824,398 B2 | 11/2010 | Woloszko et al. |
| 7,824,404 B2 | 11/2010 | Godara et al. |
| 7,828,804 B2 | 11/2010 | Li et al. |
| 7,846,156 B2 | 12/2010 | Malis et al. |
| 7,850,685 B2 | 12/2010 | Kunis et al. |
| 7,853,326 B2 | 12/2010 | Rittman, III |
| 7,857,813 B2 | 12/2010 | Schmitz et al. |
| 7,879,032 B1 | 2/2011 | Garito et al. |
| 7,887,534 B2 | 2/2011 | Hamel et al. |
| 7,887,543 B2 | 2/2011 | Sand et al. |
| 7,892,235 B2 | 2/2011 | Ellis |
| 7,896,870 B2 | 3/2011 | Arless et al. |
| 7,896,909 B2 | 3/2011 | Sharkey et al. |
| 7,901,403 B2 | 3/2011 | Woloszko et al. |
| 7,909,827 B2 | 3/2011 | Reiley et al. |
| 7,909,873 B2 | 3/2011 | Tan-Malecki et al. |
| 7,914,526 B2 | 3/2011 | Lehmann et al. |
| 7,914,535 B2 | 3/2011 | Assell et al. |
| 7,917,222 B1 | 3/2011 | Osorio et al. |
| 7,918,849 B2 | 4/2011 | Bleich et al. |
| 7,918,874 B2 | 4/2011 | Siegal |
| 7,938,835 B2 | 5/2011 | Boucher et al. |
| 7,945,331 B2 | 5/2011 | Vilims |
| 7,951,140 B2 | 5/2011 | Arless et al. |
| 7,959,634 B2 | 6/2011 | Sennett |
| 7,963,915 B2 | 6/2011 | Bleich |
| 7,967,827 B2 | 6/2011 | Osorio et al. |
| 7,972,340 B2 | 7/2011 | Sand et al. |
| 8,000,785 B2 | 8/2011 | Ritmann, III |
| 8,021,401 B2 | 9/2011 | Carl et al. |
| 8,025,688 B2 | 9/2011 | Diederich et al. |
| 8,034,052 B2 | 10/2011 | Podhajsky |
| 8,034,071 B2 | 10/2011 | Scribner et al. |
| 8,043,287 B2 | 10/2011 | Conquergood et al. |
| 8,048,030 B2 | 11/2011 | McGuckin, Jr. et al. |
| 8,048,071 B2 | 11/2011 | Youssef et al. |
| 8,048,083 B2 | 11/2011 | Shadduck et al. |
| 8,052,661 B2 | 11/2011 | McGuckin, Jr. et al. |
| 8,062,290 B2 | 11/2011 | Buysse et al. |
| 8,066,702 B2 | 11/2011 | Rittman, III et al. |
| 8,066,712 B2 | 11/2011 | Truckai et al. |
| 8,070,753 B2 | 12/2011 | Truckai et al. |
| 8,082,043 B2 | 12/2011 | Sharkey et al. |
| 8,083,736 B2 | 12/2011 | McClurken et al. |
| 8,092,456 B2 | 1/2012 | Bleich et al. |
| 8,096,957 B2 | 1/2012 | Conquergood et al. |
| 8,100,896 B2 | 1/2012 | Podhajsky |
| 8,109,933 B2 | 2/2012 | Truckai et al. |
| 8,123,750 B2 | 2/2012 | Norton et al. |
| 8,123,756 B2 | 2/2012 | Miller et al. |
| 8,128,619 B2 | 3/2012 | Sharkey et al. |
| 8,128,633 B2 | 3/2012 | Linderman et al. |
| 8,162,933 B2 | 4/2012 | Francischelli et al. |
| 8,163,031 B2 | 4/2012 | Truckai et al. |
| 8,172,846 B2 | 5/2012 | Brunnett et al. |
| 8,182,477 B2 | 5/2012 | Orszulak et al. |
| 8,187,268 B2 | 5/2012 | Godara et al. |
| 8,187,312 B2 | 5/2012 | Sharkey et al. |
| 8,192,424 B2 | 6/2012 | Woloszko et al. |
| 8,192,435 B2 | 6/2012 | Bleich et al. |
| 8,192,442 B2 | 6/2012 | Truckai et al. |
| 8,216,223 B2 | 7/2012 | Wham et al. |
| 8,226,697 B2 | 7/2012 | Sharkey et al. |
| 8,231,616 B2 | 7/2012 | McPherson et al. |
| 8,241,335 B2 | 8/2012 | Truckai et al. |
| 8,246,627 B2 | 8/2012 | Vanleeuwen et al. |
| 8,265,747 B2 | 9/2012 | Rittman, III et al. |
| 8,282,628 B2 | 10/2012 | Paul et al. |
| 8,292,882 B2 | 10/2012 | Danek et al. |
| 8,292,887 B2 | 10/2012 | Woloszko et al. |
| 8,323,277 B2 | 12/2012 | Vilims |
| 8,323,279 B2 | 12/2012 | Dahla et al. |
| 8,343,146 B2 | 1/2013 | Godara et al. |
| 8,348,946 B2 | 1/2013 | McClurken et al. |
| 8,348,955 B2 | 1/2013 | Truckai et al. |
| 8,355,799 B2 | 1/2013 | Marion et al. |
| 8,361,063 B2 | 1/2013 | Godara |
| 8,361,067 B2 | 1/2013 | Pellegrino et al. |
| 8,406,886 B2 | 3/2013 | Gaunt et al. |
| 8,409,289 B2 | 4/2013 | Truckai et al. |
| 8,414,509 B2 | 4/2013 | Diederich et al. |
| 8,414,571 B2 | 4/2013 | Pellegrino et al. |
| 8,419,730 B2 | 4/2013 | Pellegrino et al. |
| 8,419,731 B2 | 4/2013 | Pellegrino et al. |
| 8,425,430 B2 | 4/2013 | Pond, Jr. et al. |
| 8,425,507 B2 | 4/2013 | Pellegrino et al. |
| 8,430,881 B2 | 4/2013 | Bleich et al. |
| 8,430,887 B2 | 4/2013 | Truckai et al. |
| 8,444,636 B2 | 5/2013 | Shadduck et al. |
| 8,444,640 B2 | 5/2013 | Demarais et al. |
| 8,454,594 B2 | 6/2013 | Demarais et al. |
| 8,460,382 B2 | 6/2013 | Helm et al. |
| 8,475,449 B2 | 7/2013 | Werneth et al. |
| 8,486,063 B2 | 7/2013 | Werneth et al. |
| 8,487,021 B2 | 7/2013 | Truckai et al. |
| 8,504,147 B2 | 8/2013 | Deem et al. |
| 8,505,545 B2 | 8/2013 | Conquergood et al. |
| 8,518,036 B2 | 8/2013 | Leung et al. |
| 8,523,871 B2 | 9/2013 | Truckai et al. |
| 8,535,309 B2 | 9/2013 | Pellegrino et al. |
| 8,540,723 B2 | 9/2013 | Shadduck et al. |
| 8,556,891 B2 | 10/2013 | Mathur |
| 8,556,910 B2 | 10/2013 | Truckai et al. |
| 8,556,911 B2 | 10/2013 | Mehta et al. |
| 8,560,062 B2 | 10/2013 | Rittman, III et al. |
| 8,562,598 B2 | 10/2013 | Falkenstein et al. |
| 8,562,607 B2 | 10/2013 | Truckai et al. |
| 8,562,620 B2 | 10/2013 | Truckai et al. |
| 8,579,903 B2 | 11/2013 | Carl |
| 8,585,694 B2 | 11/2013 | Amoah et al. |
| 8,591,507 B2 | 11/2013 | Kramer et al. |
| 8,597,301 B2 | 12/2013 | Mitchell |
| 8,603,088 B2 | 12/2013 | Stern et al. |
| 8,613,744 B2 | 12/2013 | Pellegrino et al. |
| 8,617,156 B2 | 12/2013 | Werneth et al. |
| 8,623,014 B2 | 1/2014 | Pellegrino et al. |
| 8,623,025 B2 | 1/2014 | Tan-Malecki et al. |
| 8,628,528 B2 | 1/2014 | Pellegrino et al. |
| 8,636,736 B2 | 1/2014 | Yates et al. |
| 8,644,941 B2 | 2/2014 | Rooney et al. |
| 8,657,814 B2 | 2/2014 | Werneth et al. |
| 8,663,266 B1 | 3/2014 | Obsuth |
| 8,672,934 B2 | 3/2014 | Benamou et al. |
| 8,676,309 B2 | 3/2014 | Deem et al. |
| 8,679,023 B2 | 3/2014 | Kobayashi et al. |
| 8,690,884 B2 | 4/2014 | Linderman et al. |
| 8,696,679 B2 | 4/2014 | Shadduck et al. |
| RE44,883 E | 5/2014 | Cha |
| 8,740,897 B2 | 6/2014 | Leung et al. |

(56) References Cited

U.S. PATENT DOCUMENTS

| | | |
|---|---|---|
| 8,747,359 B2 | 6/2014 | Pakter et al. |
| 8,747,398 B2 | 6/2014 | Behnke |
| 8,758,349 B2 | 6/2014 | Germain et al. |
| 8,764,761 B2 | 7/2014 | Truckai et al. |
| 8,771,265 B2 | 7/2014 | Truckai |
| 8,771,276 B2 | 7/2014 | Linderman |
| 8,774,913 B2 | 7/2014 | Demarais et al. |
| 8,774,924 B2 | 7/2014 | Weiner |
| 8,777,479 B2 | 7/2014 | Kwan et al. |
| 8,784,411 B2 | 7/2014 | Leuthardt et al. |
| 8,795,270 B2 | 8/2014 | Drake |
| 8,808,161 B2 | 8/2014 | Gregg et al. |
| 8,808,284 B2 | 8/2014 | Pellegrino et al. |
| 8,814,873 B2 | 8/2014 | Schaller et al. |
| 8,818,503 B2 | 8/2014 | Rittman, III |
| 8,821,488 B2 | 9/2014 | Stewart et al. |
| 8,828,001 B2 | 9/2014 | Steams et al. |
| 8,845,631 B2 | 9/2014 | Werneth et al. |
| 8,864,759 B2 | 10/2014 | Godara et al. |
| 8,864,760 B2 | 10/2014 | Kramer et al. |
| 8,864,777 B2 | 10/2014 | Harrison et al. |
| 8,880,189 B2 | 11/2014 | Lipan |
| 8,882,755 B2 | 11/2014 | Leung et al. |
| 8,882,759 B2 | 11/2014 | Manley et al. |
| 8,882,764 B2 | 11/2014 | Pellegrino et al. |
| 8,894,616 B2 | 11/2014 | Harrison et al. |
| 8,894,658 B2 | 11/2014 | Linderman et al. |
| 8,911,497 B2 | 12/2014 | Chavatte et al. |
| 8,915,949 B2 | 12/2014 | Diederich et al. |
| 8,926,620 B2 | 1/2015 | Chasmawala et al. |
| 8,932,300 B2 | 1/2015 | Shadduck et al. |
| 8,939,969 B2 | 1/2015 | Temelli et al. |
| 8,968,288 B2 | 3/2015 | Brannan |
| 8,989,859 B2 | 3/2015 | Deem et al. |
| 8,992,521 B2 | 3/2015 | VanWyk |
| 8,992,522 B2 | 3/2015 | Pellegrino et al. |
| 8,992,523 B2 | 3/2015 | Pellegrino et al. |
| 8,992,524 B1 | 3/2015 | Ellman |
| 9,005,210 B2 | 4/2015 | Truckai et al. |
| 9,008,793 B1 | 4/2015 | Cosman, Sr. et al. |
| 9,017,325 B2 | 4/2015 | Pellegrino et al. |
| 9,023,038 B2 | 5/2015 | Pellegrino et al. |
| 9,028,488 B2 | 5/2015 | Gosbayeshgar |
| 9,028,538 B2 | 5/2015 | Paul et al. |
| 9,039,701 B2 | 5/2015 | Pellegrino et al. |
| 9,044,245 B2 | 6/2015 | Condie et al. |
| 9,044,254 B2 | 6/2015 | Ladtkow et al. |
| 9,044,575 B2 | 6/2015 | Beasley et al. |
| 9,050,109 B2 | 6/2015 | Smith |
| 9,050,112 B2 | 6/2015 | Greenhalgh et al. |
| 9,066,769 B2 | 6/2015 | Truckai et al. |
| 9,078,761 B2 | 7/2015 | Godara et al. |
| 9,095,359 B2 | 8/2015 | Robert et al. |
| 9,113,896 B2 | 8/2015 | Mulier et al. |
| 9,113,911 B2 | 8/2015 | Sherman |
| 9,113,925 B2 | 8/2015 | Smith et al. |
| 9,113,950 B2 | 8/2015 | Schutlz et al. |
| 9,113,974 B2 | 8/2015 | Germain |
| 9,119,623 B2 | 9/2015 | Malis et al. |
| 9,119,639 B2 | 9/2015 | Kuntz |
| 9,119,647 B2 | 9/2015 | Brannan |
| 9,119,650 B2 | 9/2015 | Brannan et al. |
| 9,125,671 B2 | 9/2015 | Germain et al. |
| 9,131,597 B2 | 9/2015 | Taft et al. |
| 9,149,652 B2 | 10/2015 | Wenz et al. |
| 9,151,680 B2 | 10/2015 | Brannan |
| 9,155,895 B2 | 10/2015 | Wacnik et al. |
| 9,161,735 B2 | 10/2015 | Bradford et al. |
| 9,161,797 B2 | 10/2015 | Truckai et al. |
| 9,161,798 B2 | 10/2015 | Truckai et al. |
| 9,161,805 B2 | 10/2015 | Isenberg |
| 9,161,809 B2 | 10/2015 | Germain et al. |
| 9,161,814 B2 | 10/2015 | Brannan et al. |
| 9,168,047 B2 | 10/2015 | To et al. |
| 9,168,054 B2 | 10/2015 | Turner et al. |
| 9,168,078 B2 | 10/2015 | Linderman et al. |
| 9,168,085 B2 | 10/2015 | Juzkiw |
| 9,173,676 B2 | 11/2015 | Pellegrino et al. |
| 9,173,700 B2 | 11/2015 | Godara et al. |
| 9,179,970 B2 | 11/2015 | Utley et al. |
| 9,179,972 B2 | 11/2015 | Olson |
| 9,180,416 B2 | 11/2015 | Phan et al. |
| 9,186,197 B2 | 11/2015 | McKay |
| 9,192,308 B2 | 11/2015 | Brannan et al. |
| 9,192,397 B2 | 11/2015 | Sennett et al. |
| 9,198,684 B2 | 12/2015 | Arthur et al. |
| 9,216,053 B2 | 12/2015 | Godara et al. |
| 9,216,195 B2 | 12/2015 | Truckai et al. |
| 9,226,756 B2 | 1/2016 | Teisen et al. |
| 9,232,954 B2 | 1/2016 | Steiner et al. |
| 9,237,916 B2 | 1/2016 | Crainich et al. |
| 9,238,139 B2 | 1/2016 | Degiorgio et al. |
| 9,241,057 B2 | 1/2016 | Van Wyk et al. |
| 9,241,729 B2 | 1/2016 | Juntz et al. |
| 9,241,760 B2 | 1/2016 | Godara et al. |
| 9,247,970 B2 | 2/2016 | Teisen |
| 9,247,992 B2 | 2/2016 | Ladtkow et al. |
| 9,247,993 B2 | 2/2016 | Ladtkow et al. |
| 9,248,278 B2 | 2/2016 | Crosby et al. |
| 9,248,289 B2 | 2/2016 | Bennett et al. |
| 9,254,168 B2 | 2/2016 | Palanker |
| 9,254,386 B2 | 2/2016 | Lee et al. |
| 9,259,241 B2 | 2/2016 | Pellegrino et al. |
| 9,259,248 B2 | 2/2016 | Leuthardt et al. |
| 9,259,269 B2 | 2/2016 | Ladtkow et al. |
| 9,259,569 B2 | 2/2016 | Brounstein et al. |
| 9,259,577 B2 | 2/2016 | Kaula et al. |
| 9,265,522 B2 | 2/2016 | Pellegrino et al. |
| 9,265,557 B2 | 2/2016 | Sherman et al. |
| 9,277,969 B2 | 3/2016 | Brannan et al. |
| 9,282,979 B2 | 3/2016 | O'Neil et al. |
| 9,282,988 B2 | 3/2016 | Goshayeshgar |
| 9,283,015 B2 | 3/2016 | Tan-Malecki et al. |
| 9,289,607 B2 | 3/2016 | Su et al. |
| 9,295,479 B2 | 3/2016 | Hibri et al. |
| 9,295,517 B2 | 3/2016 | Peyman et al. |
| 9,295,841 B2 | 3/2016 | Fang et al. |
| 9,301,723 B2 | 4/2016 | Brannan et al. |
| 9,301,804 B2 | 4/2016 | Bonn |
| 9,302,117 B2 | 4/2016 | De Vincentiis |
| 9,308,036 B2 | 4/2016 | Robinson |
| 9,308,045 B2 | 4/2016 | Kim et al. |
| 9,314,252 B2 | 4/2016 | Schaller et al. |
| 9,314,613 B2 | 4/2016 | Mashiach |
| 9,314,618 B2 | 4/2016 | Imran et al. |
| 9,333,033 B2 | 5/2016 | Gliner |
| 9,333,144 B2 | 5/2016 | Baxter et al. |
| 9,333,339 B2 | 5/2016 | Weiner |
| 9,333,361 B2 | 5/2016 | Li et al. |
| 9,333,373 B2 | 5/2016 | Imran |
| 9,339,655 B2 | 5/2016 | Carbunaru |
| 9,345,530 B2 | 5/2016 | Ballakur et al. |
| 9,345,537 B2 | 5/2016 | Harrison et al. |
| 9,345,538 B2 | 5/2016 | Deem et al. |
| 9,351,739 B2 | 5/2016 | Mahoney et al. |
| 9,358,059 B2 | 6/2016 | Linderman et al. |
| 9,358,067 B2 | 6/2016 | Lee et al. |
| 9,358,396 B2 | 6/2016 | Holley |
| 9,364,242 B2 | 6/2016 | Tornier et al. |
| 9,364,286 B2 | 6/2016 | Werneth et al. |
| 9,370,348 B2 | 6/2016 | Tally et al. |
| 9,370,373 B2 | 6/2016 | Smith |
| 9,370,392 B2 | 6/2016 | Sharonov |
| 9,370,398 B2 | 6/2016 | Ladtkow et al. |
| 9,375,274 B2 | 6/2016 | Reid |
| 9,375,275 B2 | 6/2016 | Lee et al. |
| 9,375,278 B2 | 6/2016 | Robert et al. |
| 9,375,279 B2 | 6/2016 | Brannan |
| 9,375,283 B2 | 6/2016 | Arts et al. |
| 9,381,024 B2 | 7/2016 | Globerman et al. |
| 9,381,045 B2 | 7/2016 | Donner et al. |
| 9,381,050 B2 | 7/2016 | Lee et al. |
| 9,381,359 B2 | 7/2016 | Parramon et al. |
| 9,387,094 B2 | 7/2016 | Manrique et al. |

(56) References Cited

U.S. PATENT DOCUMENTS

| | | |
|---|---|---|
| 9,393,416 B2 | 7/2016 | Rooney et al. |
| 9,398,931 B2 | 7/2016 | Wittenberger et al. |
| 9,399,144 B2 | 7/2016 | Howard |
| 9,403,038 B2 | 8/2016 | Tyler |
| 9,409,023 B2 | 8/2016 | Burdick et al. |
| 9,414,884 B2 | 8/2016 | Faehndrich et al. |
| 9,421,057 B2 | 8/2016 | Germain |
| 9,421,064 B2 | 8/2016 | Pellegrino et al. |
| 9,421,123 B2 | 8/2016 | Lee et al. |
| 9,421,371 B2 | 8/2016 | Pless et al. |
| 9,421,378 B2 | 8/2016 | Lian et al. |
| 9,439,693 B2 | 9/2016 | Childs et al. |
| 9,439,721 B2 | 9/2016 | Werneth et al. |
| 9,445,859 B2 | 9/2016 | Pageard |
| 9,446,229 B2 | 9/2016 | Omar-Pasha |
| 9,446,235 B2 | 9/2016 | Su et al. |
| 9,452,286 B2 | 9/2016 | Cowan et al. |
| 9,456,836 B2 | 10/2016 | Boling et al. |
| 9,457,182 B2 | 10/2016 | Koop |
| 9,468,485 B2 | 10/2016 | Wittenberger et al. |
| 9,468,495 B2 | 10/2016 | Kunis et al. |
| 9,474,565 B2 | 10/2016 | Shikhman et al. |
| 9,474,906 B2 | 10/2016 | Sachs et al. |
| 9,480,485 B2 | 11/2016 | Aho et al. |
| 9,486,279 B2 | 11/2016 | Pellegrino et al. |
| 9,486,447 B2 | 11/2016 | Peterson et al. |
| 9,486,621 B2 | 11/2016 | Howard et al. |
| 9,492,657 B2 | 11/2016 | Gerber |
| 9,492,664 B2 | 11/2016 | Peterson |
| 9,504,372 B2 | 11/2016 | Kim |
| 9,504,481 B2 | 11/2016 | Germain et al. |
| 9,504,506 B2 | 11/2016 | Crainich et al. |
| 9,504,518 B2 | 11/2016 | Condie et al. |
| 9,504,530 B2 | 11/2016 | Hartmann et al. |
| 9,504,818 B2 | 11/2016 | Moffitt et al. |
| 9,511,229 B2 | 12/2016 | Bradley |
| 9,511,231 B1 | 12/2016 | Kent et al. |
| 9,513,761 B2 | 12/2016 | Shikhman et al. |
| 9,517,077 B2 | 12/2016 | Blain et al. |
| 9,517,200 B2 | 12/2016 | Bleier |
| 9,526,507 B2 | 12/2016 | Germain |
| 9,526,551 B2 | 12/2016 | Linderman |
| 9,526,559 B2 | 12/2016 | Banamou et al. |
| 9,532,828 B2 | 1/2017 | Condie et al. |
| 9,545,283 B2 | 1/2017 | Sack et al. |
| 9,549,772 B2 | 1/2017 | Carl |
| 9,550,041 B2 | 1/2017 | Bedell |
| 9,555,037 B2 | 1/2017 | Podhajsky |
| 9,556,101 B2 | 1/2017 | Robertson et al. |
| 9,556,449 B2 | 1/2017 | Basu et al. |
| 9,566,108 B2 | 2/2017 | Brustad et al. |
| 9,566,449 B2 | 2/2017 | Perryman et al. |
| 9,572,976 B2 | 2/2017 | Howard et al. |
| 9,572,986 B2 | 2/2017 | Moffitt |
| 9,579,127 B2 | 2/2017 | Kostuik et al. |
| 9,579,518 B2 | 2/2017 | Gertner |
| 9,597,091 B2 | 3/2017 | Bromer |
| 9,597,148 B2 | 3/2017 | Olson |
| RE46,356 E | 4/2017 | Pellegrino et al. |
| 9,610,083 B2 | 4/2017 | Kuntz |
| 9,610,117 B2 | 4/2017 | Germain |
| 9,636,175 B2 | 5/2017 | Stern et al. |
| 9,642,629 B2 | 5/2017 | Griffiths et al. |
| 9,649,116 B2 | 5/2017 | Germain |
| 9,675,408 B2 | 6/2017 | Godara et al. |
| 9,681,889 B1 | 6/2017 | Greenhalgh et al. |
| 9,687,255 B2 | 6/2017 | Sennett et al. |
| 9,717,551 B2 | 8/2017 | Krueger et al. |
| 9,724,107 B2 | 8/2017 | Pellegrino et al. |
| 9,724,151 B2 | 8/2017 | Edidin |
| 9,730,707 B2 | 8/2017 | Sasaki et al. |
| 9,743,854 B2 | 8/2017 | Stewart et al. |
| 9,743,938 B2 | 8/2017 | Germain et al. |
| 9,750,560 B2 | 9/2017 | Ballakur et al. |
| 9,750,570 B2 | 9/2017 | Condie et al. |
| 9,757,193 B2 | 9/2017 | Zarins et al. |
| 9,770,280 B2 | 9/2017 | Diederich et al. |
| 9,775,627 B2 | 10/2017 | Patel et al. |
| 9,782,221 B2 | 10/2017 | Srinivasan |
| 9,795,802 B2 | 10/2017 | Mohamed et al. |
| 9,814,514 B2 | 11/2017 | Shelton, IV et al. |
| 9,826,985 B2 | 11/2017 | Slobitker et al. |
| 9,844,406 B2 | 12/2017 | Edwards et al. |
| 9,848,890 B2 | 12/2017 | Yoon et al. |
| 9,848,944 B2 | 12/2017 | Sutton et al. |
| 9,872,687 B2 | 1/2018 | Tornier et al. |
| 9,872,691 B2 | 1/2018 | Griffiths et al. |
| 9,877,707 B2 | 1/2018 | Godara et al. |
| 9,901,392 B2 | 2/2018 | Phan et al. |
| 9,913,675 B2 | 3/2018 | Germain |
| 9,918,786 B2 | 3/2018 | Wang et al. |
| 9,980,771 B2 | 5/2018 | Carter et al. |
| 9,993,285 B2 | 6/2018 | Govari et al. |
| 10,022,140 B2 | 7/2018 | Germain et al. |
| 10,028,753 B2 | 7/2018 | Pellegrino et al. |
| 10,028,784 B2 | 7/2018 | Kramer et al. |
| 10,052,149 B2 | 8/2018 | Germain et al. |
| 10,052,152 B2 | 8/2018 | Tegg et al. |
| 10,052,153 B2 | 8/2018 | Olson |
| 10,058,336 B2 | 8/2018 | Truckai et al. |
| 10,105,175 B2 | 10/2018 | Godara et al. |
| 10,111,674 B2 | 10/2018 | Crainich et al. |
| 10,111,704 B2 | 10/2018 | Pellegrino et al. |
| 10,123,809 B2 | 11/2018 | Germain |
| 10,159,497 B2 | 12/2018 | Kuntz et al. |
| 10,245,092 B2 | 4/2019 | Germain |
| 10,265,099 B2 | 4/2019 | Pellegrino et al. |
| 10,272,271 B2 | 4/2019 | Diederich et al. |
| 10,292,716 B2 | 5/2019 | Aho et al. |
| 10,292,719 B2 | 5/2019 | Burger et al. |
| 10,299,805 B2 | 5/2019 | Germain et al. |
| 10,314,633 B2 | 6/2019 | Linderman et al. |
| 10,327,841 B2 | 6/2019 | Germain |
| 10,357,258 B2 | 7/2019 | Patel et al. |
| 10,357,307 B2 | 7/2019 | Harrison et al. |
| 10,376,271 B2 | 8/2019 | Mehta et al. |
| 10,383,641 B2 | 8/2019 | LeRoy et al. |
| 10,390,877 B2 | 8/2019 | Heggeness et al. |
| 10,441,295 B2 | 10/2019 | Brockman et al. |
| 10,441,354 B2 | 10/2019 | Govari et al. |
| 10,448,995 B2 | 10/2019 | Olson |
| 10,456,187 B2 | 10/2019 | Edidin |
| 10,463,380 B2 | 11/2019 | Purdy et al. |
| 10,463,423 B2 | 11/2019 | Sutton et al. |
| 10,470,781 B2 | 11/2019 | Purdy et al. |
| 10,478,241 B2 | 11/2019 | Purdy et al. |
| 10,478,246 B2 | 11/2019 | Pellegrino et al. |
| 10,493,247 B2 | 12/2019 | Goshayeshgar |
| 10,499,960 B2 | 12/2019 | Sinnott et al. |
| 10,517,611 B2 | 12/2019 | Patel et al. |
| 10,524,805 B2 | 1/2020 | Zilberman et al. |
| 10,582,966 B2 | 3/2020 | Orczy-Timko et al. |
| 10,588,691 B2 | 3/2020 | Pellegino et al. |
| 10,589,131 B2 | 3/2020 | Diederich et al. |
| 10,603,522 B2 | 3/2020 | Diederich et al. |
| 10,624,652 B2 | 4/2020 | Germain et al. |
| 10,660,656 B2 | 5/2020 | Purdy et al. |
| 10,835,234 B2 | 11/2020 | Harari et al. |
| 10,849,613 B2 | 12/2020 | Rosner et al. |
| 10,864,040 B2 | 12/2020 | Dastjerdi et al. |
| 10,898,254 B2 | 1/2021 | Diederich et al. |
| 10,905,440 B2 | 2/2021 | Pellegrino et al. |
| 10,918,363 B2 | 2/2021 | Godara et al. |
| RE48,460 E | 3/2021 | Pellegrino et al. |
| 10,952,771 B2 | 3/2021 | Pellegrino |
| 11,007,010 B2 | 5/2021 | Donovan et al. |
| 11,026,734 B2 | 6/2021 | Truckai et al. |
| 11,026,744 B2 | 6/2021 | Purdy et al. |
| 11,052,267 B2 | 7/2021 | Diederich et al. |
| 11,065,046 B2 | 7/2021 | Edidin |
| 11,116,570 B2 | 9/2021 | Purdy et al. |
| 11,123,103 B2 | 9/2021 | Donovan et al. |
| 11,147,684 B2 | 10/2021 | Neubardt |
| 11,160,503 B2 | 11/2021 | Peesapati et al. |

(56) References Cited

U.S. PATENT DOCUMENTS

| | | |
|---|---|---|
| 11,160,563 B2 | 11/2021 | Patel et al. |
| 11,166,747 B2 | 11/2021 | Brockman et al. |
| 11,207,100 B2 | 11/2021 | Donovan et al. |
| 11,191,575 B2 | 12/2021 | Kidman et al. |
| 11,224,475 B2 | 1/2022 | Godara et al. |
| 11,234,764 B1 | 2/2022 | Patel et al. |
| 11,259,818 B2 | 3/2022 | Brockman et al. |
| 11,291,502 B2 | 4/2022 | Patel et al. |
| 11,344,350 B2 | 5/2022 | Purdy et al. |
| 11,364,069 B2 | 6/2022 | Heggeness |
| 11,376,021 B2 | 7/2022 | Marino et al. |
| 11,389,181 B2 | 7/2022 | Dutertre et al. |
| 11,419,614 B2 | 8/2022 | Weitzman et al. |
| 11,426,199 B2 | 8/2022 | Donovan et al. |
| 11,471,171 B2 | 10/2022 | Pellegrino et al. |
| 11,471,210 B2 | 10/2022 | Pellegrino et al. |
| 11,497,543 B2 | 11/2022 | Sprinkle et al. |
| 11,510,723 B2 | 11/2022 | Defosset et al. |
| 11,596,468 B2 | 3/2023 | Pellegrino et al. |
| 11,690,667 B2 | 7/2023 | Pellegrino et al. |
| 2001/0001314 A1 | 5/2001 | Davison et al. |
| 2001/0001811 A1 | 5/2001 | Burney et al. |
| 2001/0020167 A1 | 9/2001 | Woloszko et al. |
| 2001/0023348 A1 | 9/2001 | Ashley et al. |
| 2001/0025176 A1 | 9/2001 | Ellsberry et al. |
| 2001/0025177 A1 | 9/2001 | Woloszko et al. |
| 2001/0027295 A1 | 10/2001 | Dulak et al. |
| 2001/0029370 A1 | 10/2001 | Hovda et al. |
| 2001/0029373 A1 | 10/2001 | Baker et al. |
| 2001/0029393 A1 | 10/2001 | Tierney et al. |
| 2001/0032001 A1 | 10/2001 | Ricart et al. |
| 2001/0047167 A1 | 11/2001 | Heggeness |
| 2001/0049522 A1 | 12/2001 | Eggers et al. |
| 2001/0049527 A1 | 12/2001 | Cragg |
| 2001/0051802 A1 | 12/2001 | Woloszko et al. |
| 2001/0053885 A1 | 12/2001 | Gielen et al. |
| 2001/0056280 A1 | 12/2001 | Underwood et al. |
| 2002/0016583 A1 | 2/2002 | Cragg |
| 2002/0016600 A1 | 2/2002 | Cosman |
| 2002/0019626 A1 | 2/2002 | Sharkey et al. |
| 2002/0026186 A1 | 2/2002 | Woloszko et al. |
| 2002/0049438 A1 | 4/2002 | Sharkey et al. |
| 2002/0052600 A1 | 5/2002 | Davison et al. |
| 2002/0068930 A1 | 6/2002 | Tasto et al. |
| 2002/0095144 A1 | 7/2002 | Carl |
| 2002/0095151 A1 | 7/2002 | Dahla et al. |
| 2002/0095152 A1 | 7/2002 | Ciarrocca et al. |
| 2002/0099366 A1 | 7/2002 | Dahla et al. |
| 2002/0111661 A1 | 8/2002 | Cross et al. |
| 2002/0115945 A1 | 8/2002 | D'Luzansky et al. |
| 2002/0120259 A1 | 8/2002 | Lettice et al. |
| 2002/0133148 A1 | 9/2002 | Daniel et al. |
| 2002/0147444 A1 | 10/2002 | Shah et al. |
| 2002/0151885 A1 | 10/2002 | Underwood et al. |
| 2002/0165532 A1 | 11/2002 | Hill et al. |
| 2002/0183758 A1 | 12/2002 | Middleton et al. |
| 2002/0188284 A1 | 12/2002 | To et al. |
| 2002/0188290 A1 | 12/2002 | Sharkey et al. |
| 2002/0193708 A1 | 12/2002 | Thompson et al. |
| 2002/0193789 A1 | 12/2002 | Underwood et al. |
| 2003/0009164 A1 | 1/2003 | Woloszko et al. |
| 2003/0014047 A1 | 1/2003 | Woloszko et al. |
| 2003/0014088 A1 | 1/2003 | Fang et al. |
| 2003/0028147 A1 | 2/2003 | Aves et al. |
| 2003/0028189 A1 | 2/2003 | Woloszko et al. |
| 2003/0040710 A1 | 2/2003 | Polidoro |
| 2003/0040742 A1 | 2/2003 | Underwood et al. |
| 2003/0040743 A1 | 2/2003 | Cosman et al. |
| 2003/0055418 A1 | 3/2003 | Tasto et al. |
| 2003/0069569 A1 | 4/2003 | Burdette et al. |
| 2003/0083592 A1 | 5/2003 | Faciszewski |
| 2003/0084907 A1 | 5/2003 | Pacek et al. |
| 2003/0097126 A1 | 5/2003 | Woloszko et al. |
| 2003/0097129 A1 | 5/2003 | Davison et al. |
| 2003/0130655 A1 | 7/2003 | Woloszko et al. |
| 2003/0139652 A1 | 7/2003 | Kang et al. |
| 2003/0158545 A1* | 8/2003 | Hovda ............... A61B 18/148 606/49 |
| 2003/0181963 A1 | 9/2003 | Pellegrino et al. |
| 2003/0208194 A1 | 11/2003 | Hovda et al. |
| 2003/0216725 A1 | 11/2003 | Woloszko et al. |
| 2003/0216726 A1 | 11/2003 | Eggers et al. |
| 2003/0225364 A1 | 12/2003 | Kraft |
| 2004/0006339 A1 | 1/2004 | Underwood et al. |
| 2004/0015163 A1 | 1/2004 | Buysse et al. |
| 2004/0024399 A1 | 2/2004 | Sharps et al. |
| 2004/0054366 A1 | 3/2004 | Davison et al. |
| 2004/0064023 A1 | 4/2004 | Thomas et al. |
| 2004/0064136 A1 | 4/2004 | Crombie et al. |
| 2004/0064137 A1 | 4/2004 | Pellegrino et al. |
| 2004/0068242 A1 | 4/2004 | McGuckin, Jr. |
| 2004/0082942 A1 | 4/2004 | Katzman |
| 2004/0082946 A1 | 4/2004 | Malis et al. |
| 2004/0087937 A1 | 5/2004 | Eggers et al. |
| 2004/0111087 A1 | 6/2004 | Stern et al. |
| 2004/0116922 A1 | 6/2004 | Hovda et al. |
| 2004/0120668 A1 | 6/2004 | Loeb |
| 2004/0120891 A1 | 6/2004 | Hill et al. |
| 2004/0133124 A1 | 7/2004 | Bates et al. |
| 2004/0162559 A1 | 8/2004 | Arramon |
| 2004/0186544 A1 | 9/2004 | King |
| 2004/0193151 A1 | 9/2004 | To et al. |
| 2004/0193152 A1 | 9/2004 | Sutton |
| 2004/0220577 A1 | 11/2004 | Cragg et al. |
| 2004/0225228 A1 | 11/2004 | Ferree |
| 2004/0230190 A1 | 11/2004 | Dahla et al. |
| 2004/0267269 A1 | 12/2004 | Middleton et al. |
| 2005/0004634 A1 | 1/2005 | Ricart et al. |
| 2005/0010095 A1 | 1/2005 | Stewart et al. |
| 2005/0010203 A1 | 1/2005 | Edwards et al. |
| 2005/0010205 A1 | 1/2005 | Hovda et al. |
| 2005/0043737 A1 | 2/2005 | Reiley et al. |
| 2005/0055096 A1 | 3/2005 | Serhan et al. |
| 2005/0124989 A1 | 6/2005 | Suddaby |
| 2005/0177209 A1 | 8/2005 | Leung et al. |
| 2005/0177210 A1 | 8/2005 | Leung et al. |
| 2005/0177211 A1 | 8/2005 | Leung et al. |
| 2005/0182417 A1 | 8/2005 | Pagano |
| 2005/0192564 A1 | 9/2005 | Cosman et al. |
| 2005/0209610 A1 | 9/2005 | Carrison |
| 2005/0209659 A1 | 9/2005 | Pellegrino et al. |
| 2005/0216018 A1 | 9/2005 | Sennett |
| 2005/0234445 A1 | 10/2005 | Conquergood et al. |
| 2005/0261754 A1 | 11/2005 | Woloszko |
| 2005/0267552 A1 | 12/2005 | Conquergood et al. |
| 2005/0278007 A1 | 12/2005 | Godara |
| 2005/0283148 A1 | 12/2005 | Janssen et al. |
| 2006/0004369 A1 | 1/2006 | Patel et al. |
| 2006/0036264 A1 | 2/2006 | Selover et al. |
| 2006/0052743 A1 | 3/2006 | Reynolds |
| 2006/0064101 A1 | 3/2006 | Arramon |
| 2006/0095026 A1 | 5/2006 | Ricart et al. |
| 2006/0095028 A1 | 5/2006 | Bleich |
| 2006/0106375 A1 | 5/2006 | Werneth et al. |
| 2006/0106376 A1 | 5/2006 | Godara et al. |
| 2006/0122458 A1 | 6/2006 | Bleich |
| 2006/0129101 A1 | 6/2006 | McGuckin |
| 2006/0178670 A1 | 8/2006 | Woloszko et al. |
| 2006/0200121 A1 | 9/2006 | Mowery |
| 2006/0206128 A1 | 9/2006 | Conquergood et al. |
| 2006/0206129 A1 | 9/2006 | Conquergood et al. |
| 2006/0206130 A1 | 9/2006 | Conquergood et al. |
| 2006/0206132 A1 | 9/2006 | Conquergood et al. |
| 2006/0206133 A1 | 9/2006 | Conquergood et al. |
| 2006/0206134 A1 | 9/2006 | Conquergood et al. |
| 2006/0206166 A1 | 9/2006 | Weiner |
| 2006/0217736 A1 | 9/2006 | Kaneko et al. |
| 2006/0229625 A1 | 10/2006 | Truckai et al. |
| 2006/0247746 A1 | 11/2006 | Danek et al. |
| 2006/0253117 A1 | 11/2006 | Hovda et al. |
| 2006/0259026 A1 | 11/2006 | Godara et al. |
| 2006/0264957 A1 | 11/2006 | Cragg et al. |
| 2006/0264965 A1 | 11/2006 | Shadduck et al. |
| 2006/0265014 A1 | 11/2006 | Demarais et al. |

(56) References Cited

U.S. PATENT DOCUMENTS

| | | |
|---|---|---|
| 2006/0276749 A1 | 12/2006 | Selmon et al. |
| 2006/0287649 A1 | 12/2006 | Ormsby et al. |
| 2007/0021803 A1 | 1/2007 | Deem et al. |
| 2007/0027449 A1 | 2/2007 | Godara et al. |
| 2007/0055316 A1 | 3/2007 | Godara et al. |
| 2007/0066987 A1 | 3/2007 | Scanlan, Jr. et al. |
| 2007/0074719 A1 | 4/2007 | Danek et al. |
| 2007/0118142 A1 | 5/2007 | Krueger et al. |
| 2007/0129715 A1 | 6/2007 | Eggers et al. |
| 2007/0142791 A1 | 6/2007 | Yeung et al. |
| 2007/0142842 A1 | 6/2007 | Krueger et al. |
| 2007/0149966 A1 | 6/2007 | Dahla et al. |
| 2007/0179497 A1 | 8/2007 | Eggers et al. |
| 2007/0185231 A1 | 8/2007 | Liu et al. |
| 2007/0213584 A1 | 9/2007 | Kim et al. |
| 2007/0213735 A1 | 9/2007 | Saadat et al. |
| 2007/0260237 A1 | 11/2007 | Sutton et al. |
| 2008/0004621 A1 | 1/2008 | Dahla et al. |
| 2008/0004675 A1 | 1/2008 | King et al. |
| 2008/0009847 A1 | 1/2008 | Ricart et al. |
| 2008/0021447 A1 | 1/2008 | Davison et al. |
| 2008/0021463 A1 | 1/2008 | Georgy |
| 2008/0058707 A1 | 3/2008 | Ashley et al. |
| 2008/0065062 A1 | 3/2008 | Leung et al. |
| 2008/0091207 A1 | 4/2008 | Truckai et al. |
| 2008/0114364 A1 | 5/2008 | Goldin et al. |
| 2008/0119844 A1 | 5/2008 | Woloszko et al. |
| 2008/0119846 A1 | 5/2008 | Rioux |
| 2008/0132890 A1 | 6/2008 | Woloszko et al. |
| 2008/0161804 A1 | 7/2008 | Rioux et al. |
| 2008/0275458 A1 | 11/2008 | Bleich et al. |
| 2008/0281322 A1 | 11/2008 | Sherman et al. |
| 2008/0294166 A1 | 11/2008 | Goldin et al. |
| 2008/0294167 A1 | 11/2008 | Schumacher et al. |
| 2009/0030308 A1 | 1/2009 | Bradford et al. |
| 2009/0054951 A1 | 2/2009 | Leuthardt et al. |
| 2009/0069807 A1 | 3/2009 | Eggers et al. |
| 2009/0076520 A1 | 3/2009 | Choi |
| 2009/0105775 A1 | 4/2009 | Mitchell et al. |
| 2009/0112278 A1 | 4/2009 | Wingeier et al. |
| 2009/0118731 A1 | 5/2009 | Young et al. |
| 2009/0131867 A1 | 5/2009 | Liu et al. |
| 2009/0131886 A1 | 5/2009 | Liu et al. |
| 2009/0149846 A1 | 6/2009 | Hoey et al. |
| 2009/0149878 A1 | 6/2009 | Truckai et al. |
| 2009/0204192 A1 | 8/2009 | Carlton et al. |
| 2009/0222053 A1 | 9/2009 | Gaunt et al. |
| 2009/0312764 A1 | 12/2009 | Marino |
| 2010/0010392 A1 | 1/2010 | Skelton et al. |
| 2010/0016929 A1 | 1/2010 | Prochazka |
| 2010/0023006 A1 | 1/2010 | Ellman |
| 2010/0023065 A1 | 1/2010 | Welch et al. |
| 2010/0082033 A1 | 4/2010 | Germain |
| 2010/0094269 A1 | 4/2010 | Pellegrino et al. |
| 2010/0114098 A1 | 5/2010 | Carl |
| 2010/0145424 A1 | 6/2010 | Podhajsky et al. |
| 2010/0179556 A1 | 7/2010 | Scribner et al. |
| 2010/0185082 A1 | 7/2010 | Chandran et al. |
| 2010/0185161 A1* | 7/2010 | Pellegrino .......... A61B 17/3421 604/272 |
| 2010/0211076 A1 | 8/2010 | Germain et al. |
| 2010/0222777 A1 | 9/2010 | Sutton et al. |
| 2010/0261989 A1 | 10/2010 | Boseck et al. |
| 2010/0261990 A1 | 10/2010 | Gillis et al. |
| 2010/0286487 A1 | 11/2010 | Van Lue |
| 2010/0298737 A1 | 11/2010 | Koehler |
| 2010/0298822 A1 | 11/2010 | Behnke |
| 2010/0298832 A1 | 11/2010 | Lau et al. |
| 2010/0305559 A1 | 12/2010 | Brannan et al. |
| 2010/0324506 A1 | 12/2010 | Pellegrino et al. |
| 2011/0022133 A1 | 1/2011 | Diederich et al. |
| 2011/0034884 A9 | 2/2011 | Pellegrino et al. |
| 2011/0040362 A1 | 2/2011 | Godara et al. |
| 2011/0077628 A1 | 3/2011 | Hoey et al. |
| 2011/0087314 A1 | 4/2011 | Diederich et al. |
| 2011/0118735 A1 | 5/2011 | Abou-Marie et al. |
| 2011/0130751 A1 | 6/2011 | Malis et al. |
| 2011/0144524 A1 | 6/2011 | Fish et al. |
| 2011/0152855 A1 | 6/2011 | Mayse et al. |
| 2011/0196361 A1 | 8/2011 | Vilims |
| 2011/0206260 A1 | 8/2011 | Bergmans et al. |
| 2011/0264098 A1 | 10/2011 | Cobbs |
| 2011/0270238 A1 | 11/2011 | Rizq et al. |
| 2011/0276001 A1 | 11/2011 | Schultz et al. |
| 2011/0295245 A1 | 12/2011 | Willyard et al. |
| 2011/0295261 A1 | 12/2011 | Germain |
| 2011/0319765 A1* | 12/2011 | Gertner ................... A61N 7/00 600/453 |
| 2012/0029420 A1 | 2/2012 | Rittman et al. |
| 2012/0116266 A1 | 5/2012 | House et al. |
| 2012/0136346 A1 | 5/2012 | Condie et al. |
| 2012/0136348 A1 | 5/2012 | Condie et al. |
| 2012/0143090 A1 | 6/2012 | Hay et al. |
| 2012/0143341 A1 | 6/2012 | Zipnick |
| 2012/0172858 A1 | 7/2012 | Harrison et al. |
| 2012/0172859 A1 | 7/2012 | Condie et al. |
| 2012/0191095 A1 | 7/2012 | Burger et al. |
| 2012/0196251 A1 | 8/2012 | Taft et al. |
| 2012/0197344 A1 | 8/2012 | Taft et al. |
| 2012/0203219 A1 | 8/2012 | Evans et al. |
| 2012/0226145 A1 | 9/2012 | Chang et al. |
| 2012/0226273 A1 | 9/2012 | Nguyen et al. |
| 2012/0239049 A1 | 9/2012 | Truckai et al. |
| 2012/0239050 A1 | 9/2012 | Linderman |
| 2012/0265186 A1 | 10/2012 | Burger et al. |
| 2012/0330180 A1 | 12/2012 | Pellegrino et al. |
| 2012/0330300 A1 | 12/2012 | Pellegrino et al. |
| 2012/0330301 A1 | 12/2012 | Pellegrino et al. |
| 2013/0006232 A1 | 1/2013 | Pellegrino et al. |
| 2013/0006233 A1 | 1/2013 | Pellegrino et al. |
| 2013/0012933 A1 | 1/2013 | Pellegrino et al. |
| 2013/0012935 A1 | 1/2013 | Pellegrino et al. |
| 2013/0012936 A1 | 1/2013 | Pellegrino et al. |
| 2013/0012951 A1 | 1/2013 | Linderman |
| 2013/0060244 A1 | 3/2013 | Godara et al. |
| 2013/0079810 A1 | 3/2013 | Isenberg |
| 2013/0103022 A1 | 4/2013 | Sutton et al. |
| 2013/0197508 A1 | 8/2013 | Shikhman et al. |
| 2013/0231654 A1 | 9/2013 | Germain |
| 2013/0237979 A1 | 9/2013 | Shikhman et al. |
| 2013/0261507 A1 | 10/2013 | Diederich et al. |
| 2013/0274784 A1 | 10/2013 | Lenker et al. |
| 2013/0296767 A1 | 11/2013 | Zarins et al. |
| 2013/0324993 A1 | 12/2013 | McCarthy et al. |
| 2013/0324994 A1 | 12/2013 | Pellegrino et al. |
| 2013/0324996 A1 | 12/2013 | Pellegrino et al. |
| 2013/0324997 A1 | 12/2013 | Pellegrino et al. |
| 2013/0331840 A1 | 12/2013 | Teisen et al. |
| 2013/0345765 A1 | 12/2013 | Brockman et al. |
| 2014/0031715 A1 | 1/2014 | Sherar et al. |
| 2014/0039500 A1 | 2/2014 | Pellegrino et al. |
| 2014/0046245 A1 | 2/2014 | Cornacchia |
| 2014/0046328 A1 | 2/2014 | Schumacher et al. |
| 2014/0066913 A1 | 3/2014 | Sherman |
| 2014/0088575 A1 | 3/2014 | Loeb |
| 2014/0148801 A1 | 5/2014 | Asher et al. |
| 2014/0148805 A1 | 5/2014 | Stewart et al. |
| 2014/0171942 A1 | 6/2014 | Werneth et al. |
| 2014/0194887 A1 | 7/2014 | Shenoy |
| 2014/0221967 A1 | 8/2014 | Childs et al. |
| 2014/0236137 A1 | 8/2014 | Tran et al. |
| 2014/0236144 A1 | 8/2014 | Krueger et al. |
| 2014/0243823 A1 | 8/2014 | Godara et al. |
| 2014/0243943 A1 | 8/2014 | Rao et al. |
| 2014/0257265 A1 | 9/2014 | Godara et al. |
| 2014/0257296 A1 | 9/2014 | Morgenstern Lopez |
| 2014/0271717 A1 | 9/2014 | Goshayeshgar et al. |
| 2014/0275760 A1 | 9/2014 | Lee et al. |
| 2014/0276713 A1 | 9/2014 | Lee et al. |
| 2014/0276728 A1 | 9/2014 | Goshayeshgar et al. |
| 2014/0276744 A1 | 9/2014 | Arthur et al. |
| 2014/0288544 A1 | 9/2014 | Diederich et al. |
| 2014/0288546 A1 | 9/2014 | Sherman et al. |
| 2014/0296850 A1 | 10/2014 | Condie et al. |

(56) References Cited

U.S. PATENT DOCUMENTS

| | | |
|---|---|---|
| 2014/0303610 A1 | 10/2014 | McCarthy et al. |
| 2014/0303614 A1 | 10/2014 | McCarthy et al. |
| 2014/0316405 A1 | 10/2014 | Pellegrino et al. |
| 2014/0316413 A1 | 10/2014 | Burger et al. |
| 2014/0324051 A1 | 10/2014 | Pellegrino et al. |
| 2014/0330332 A1 | 11/2014 | Danek et al. |
| 2014/0336630 A1 | 11/2014 | Woloszko et al. |
| 2014/0336667 A1 | 11/2014 | Pellegrino et al. |
| 2014/0364842 A1 | 12/2014 | Werneth et al. |
| 2014/0371740 A1 | 12/2014 | Germain et al. |
| 2015/0005614 A1 | 1/2015 | Heggeness et al. |
| 2015/0005767 A1 | 1/2015 | Werneth et al. |
| 2015/0045783 A1 | 2/2015 | Edidin |
| 2015/0057658 A1 | 2/2015 | Sutton et al. |
| 2015/0065945 A1 | 3/2015 | Zarins et al. |
| 2015/0073515 A1 | 3/2015 | Turovskiy et al. |
| 2015/0105701 A1 | 4/2015 | Mayer et al. |
| 2015/0141876 A1 | 5/2015 | Diederich et al. |
| 2015/0157402 A1 | 6/2015 | Kunis et al. |
| 2015/0164546 A1 | 6/2015 | Pellegrino et al. |
| 2015/0196358 A1 | 7/2015 | Goshayeshgar |
| 2015/0216588 A1 | 8/2015 | Deem et al. |
| 2015/0231417 A1 | 8/2015 | Metcalf et al. |
| 2015/0272655 A1 | 10/2015 | Condie et al. |
| 2015/0273208 A1 | 10/2015 | Hamilton |
| 2015/0297246 A1 | 10/2015 | Patel et al. |
| 2015/0297282 A1 | 10/2015 | Cadouri |
| 2015/0320480 A1 | 11/2015 | Cosman, Jr. et al. |
| 2015/0335349 A1 | 11/2015 | Pellegrino et al. |
| 2015/0335382 A1 | 11/2015 | Pellegrino et al. |
| 2015/0342619 A1 | 12/2015 | Weitzman |
| 2015/0342660 A1 | 12/2015 | Nash |
| 2015/0342670 A1 | 12/2015 | Pellegrino et al. |
| 2015/0359586 A1 | 12/2015 | Heggeness |
| 2015/0374432 A1 | 12/2015 | Godara et al. |
| 2015/0374992 A1 | 12/2015 | Crosby et al. |
| 2015/0374995 A1 | 12/2015 | Foreman et al. |
| 2016/0000601 A1 | 1/2016 | Burger et al. |
| 2016/0001096 A1 | 1/2016 | Mishelevich |
| 2016/0002627 A1 | 1/2016 | Bennett et al. |
| 2016/0008593 A1 | 1/2016 | Cairns |
| 2016/0008618 A1 | 1/2016 | Omar-Pasha |
| 2016/0008628 A1 | 1/2016 | Morries et al. |
| 2016/0016012 A1 | 1/2016 | Youn et al. |
| 2016/0022988 A1 | 1/2016 | Thieme et al. |
| 2016/0022994 A1 | 1/2016 | Moffitt et al. |
| 2016/0024208 A1 | 1/2016 | MacDonald et al. |
| 2016/0029930 A1 | 2/2016 | Plumley et al. |
| 2016/0030276 A1 | 2/2016 | Spanyer |
| 2016/0030408 A1 | 2/2016 | Levin |
| 2016/0030748 A1 | 2/2016 | Edgerton et al. |
| 2016/0030765 A1 | 2/2016 | Towne et al. |
| 2016/0045207 A1 | 2/2016 | Kovacs et al. |
| 2016/0045256 A1 | 2/2016 | Godara et al. |
| 2016/0051831 A1 | 2/2016 | Lundmark et al. |
| 2016/0059007 A1 | 3/2016 | Koop |
| 2016/0074068 A1 | 3/2016 | Patwardhan |
| 2016/0074133 A1 | 3/2016 | Shikhman et al. |
| 2016/0074279 A1 | 3/2016 | Shin |
| 2016/0074661 A1 | 3/2016 | Lipani |
| 2016/0081716 A1 | 3/2016 | Boling et al. |
| 2016/0081810 A1 | 3/2016 | Reiley et al. |
| 2016/0095721 A1 | 4/2016 | Schell et al. |
| 2016/0106443 A1 | 4/2016 | Kuntz et al. |
| 2016/0106985 A1 | 4/2016 | Zhu |
| 2016/0106994 A1 | 4/2016 | Crosby et al. |
| 2016/0113704 A1 | 4/2016 | Godara et al. |
| 2016/0115173 A1 | 4/2016 | Bois et al. |
| 2016/0136310 A1 | 5/2016 | Bradford et al. |
| 2016/0144182 A1 | 5/2016 | Bennett et al. |
| 2016/0144187 A1 | 5/2016 | Caparso et al. |
| 2016/0158551 A1 | 6/2016 | Kent et al. |
| 2016/0166302 A1 | 6/2016 | Tan-Malecki et al. |
| 2016/0166835 A1 | 6/2016 | De Ridder |
| 2016/0175586 A1 | 6/2016 | Edgerton et al. |
| 2016/0199097 A1 | 7/2016 | Linderman et al. |
| 2016/0199117 A1 | 7/2016 | Druma |
| 2016/0213927 A1 | 7/2016 | McGee et al. |
| 2016/0220317 A1 | 8/2016 | Shikhman et al. |
| 2016/0220393 A1 | 8/2016 | Slivka et al. |
| 2016/0220638 A1 | 8/2016 | Dony et al. |
| 2016/0220672 A1 | 8/2016 | Chalasani et al. |
| 2016/0228131 A1 | 8/2016 | Brockman et al. |
| 2016/0228696 A1 | 8/2016 | Imran et al. |
| 2016/0235471 A1 | 8/2016 | Godara et al. |
| 2016/0235474 A1 | 8/2016 | Prisco et al. |
| 2016/0243353 A1 | 8/2016 | Ahmed |
| 2016/0246944 A1 | 8/2016 | Jain et al. |
| 2016/0250469 A1 | 9/2016 | Kim et al. |
| 2016/0250472 A1 | 9/2016 | Carbunaru |
| 2016/0262830 A1 | 9/2016 | Werneth et al. |
| 2016/0262904 A1 | 9/2016 | Schaller et al. |
| 2016/0271405 A1 | 9/2016 | Angara et al. |
| 2016/0278791 A1 | 9/2016 | Pellegrino et al. |
| 2016/0278846 A1 | 9/2016 | Harrison et al. |
| 2016/0278861 A1 | 9/2016 | Ko |
| 2016/0279190 A1 | 9/2016 | Watts et al. |
| 2016/0279408 A1 | 9/2016 | Grigsby et al. |
| 2016/0279411 A1 | 9/2016 | Rooney et al. |
| 2016/0279441 A1 | 9/2016 | Imran |
| 2016/0296739 A1 | 10/2016 | Cleveland |
| 2016/0302925 A1 | 10/2016 | Keogh et al. |
| 2016/0302936 A1 | 10/2016 | Billon et al. |
| 2016/0310739 A1 | 10/2016 | Burdick et al. |
| 2016/0317053 A1 | 11/2016 | Srivastava |
| 2016/0317211 A1 | 11/2016 | Harrison et al. |
| 2016/0317621 A1 | 11/2016 | Bright |
| 2016/0324541 A1 | 11/2016 | Pellegrino et al. |
| 2016/0324677 A1 | 11/2016 | Hyde et al. |
| 2016/0325100 A1 | 11/2016 | Lian et al. |
| 2016/0339251 A1 | 11/2016 | Kent et al. |
| 2016/0354093 A1 | 12/2016 | Pellegrino et al. |
| 2016/0354233 A1 | 12/2016 | Sansone et al. |
| 2016/0367797 A1 | 12/2016 | Eckermann |
| 2016/0367823 A1 | 12/2016 | Cowan et al. |
| 2016/0375259 A1 | 12/2016 | Davis et al. |
| 2017/0000501 A1 | 1/2017 | Aho et al. |
| 2017/0001026 A1 | 1/2017 | Schwarz et al. |
| 2017/0007277 A1 | 1/2017 | Drapeau et al. |
| 2017/0014169 A1 | 1/2017 | Dean et al. |
| 2017/0027618 A1 | 2/2017 | Lee et al. |
| 2017/0028198 A1 | 2/2017 | Degiorgio et al. |
| 2017/0028201 A1 | 2/2017 | Howard |
| 2017/0035483 A1 | 2/2017 | Crainich et al. |
| 2017/0036009 A1 | 2/2017 | Hughes et al. |
| 2017/0036025 A1 | 2/2017 | Sachs et al. |
| 2017/0036033 A9 | 2/2017 | Perryman et al. |
| 2017/0042834 A1 | 2/2017 | Westphal et al. |
| 2017/0049500 A1 | 2/2017 | Shikhman et al. |
| 2017/0049503 A1 | 2/2017 | Cosman |
| 2017/0049507 A1 | 2/2017 | Cosman |
| 2017/0049513 A1 | 2/2017 | Cosman |
| 2017/0050017 A1 | 2/2017 | Cosman |
| 2017/0050021 A1 | 2/2017 | Cosman |
| 2017/0050024 A1 | 2/2017 | Bhadra et al. |
| 2017/0056028 A1 | 3/2017 | Germain et al. |
| 2017/0065329 A1 | 3/2017 | Benamou et al. |
| 2017/0112507 A1 | 4/2017 | Crainich et al. |
| 2017/0119461 A1 | 5/2017 | Godara et al. |
| 2017/0128080 A1 | 5/2017 | Torrie |
| 2017/0128112 A1 | 5/2017 | Germain |
| 2017/0135742 A1 | 5/2017 | Lee et al. |
| 2017/0164998 A1 | 6/2017 | Klimovitch |
| 2017/0172650 A1 | 6/2017 | Germain |
| 2017/0181788 A1 | 6/2017 | Dastjerdi et al. |
| 2017/0202613 A1 | 7/2017 | Pellegrino et al. |
| 2017/0238943 A1 | 8/2017 | Sennett et al. |
| 2017/0246481 A1 | 8/2017 | Mischelevich |
| 2017/0266419 A1 | 9/2017 | Goshayeshgar |
| 2017/0303983 A1 | 10/2017 | Linderman et al. |
| 2017/0312007 A1 | 11/2017 | Harley et al. |
| 2017/0333052 A1 | 11/2017 | Ding et al. |
| 2018/0021048 A1 | 1/2018 | Pellegrino et al. |
| 2018/0042656 A1 | 2/2018 | Edidin |

(56) References Cited

U.S. PATENT DOCUMENTS

| | | |
|---|---|---|
| 2018/0055539 A1 | 3/2018 | Pellegino |
| 2018/0103964 A1 | 4/2018 | Patel et al. |
| 2018/0140245 A1 | 5/2018 | Videman |
| 2018/0153604 A1 | 6/2018 | Ayvazyan et al. |
| 2018/0161047 A1 | 6/2018 | Purdy et al. |
| 2018/0193088 A1 | 7/2018 | Sutton et al. |
| 2018/0303509 A1 | 10/2018 | Germain et al. |
| 2019/0029698 A1 | 1/2019 | Pellegrino et al. |
| 2019/0038296 A1 | 2/2019 | Pellegrino |
| 2019/0038343 A1 | 2/2019 | Sutton et al. |
| 2019/0038344 A1 | 2/2019 | Pellegrino |
| 2019/0038345 A1 | 2/2019 | Pellegrino |
| 2019/0090933 A1 | 3/2019 | Pellegrino et al. |
| 2019/0110833 A1 | 4/2019 | Pellegrino et al. |
| 2019/0118003 A1 | 4/2019 | Diederich et al. |
| 2019/0118004 A1 | 4/2019 | Diederich et al. |
| 2019/0118005 A1 | 4/2019 | Diederich et al. |
| 2019/0175252 A1 | 6/2019 | Heggeness |
| 2019/0216486 A1 | 7/2019 | Weitzman |
| 2019/0282268 A1 | 9/2019 | Pellegrino et al. |
| 2019/0290296 A1 | 9/2019 | Patel et al. |
| 2019/0298392 A1 | 10/2019 | Capote et al. |
| 2019/0365416 A1 | 12/2019 | Brockman et al. |
| 2020/0000480 A1 | 1/2020 | Alambeigi et al. |
| 2020/0022709 A1 | 1/2020 | Burger et al. |
| 2020/0022749 A1 | 1/2020 | Malkevich et al. |
| 2020/0030601 A1 | 1/2020 | Molnar et al. |
| 2020/0060695 A1 | 2/2020 | Purdy et al. |
| 2020/0060747 A1 | 2/2020 | Edidin |
| 2020/0069920 A1 | 3/2020 | Goshayeshgar |
| 2020/0078083 A1 | 3/2020 | Sprinkle et al. |
| 2020/0138454 A1 | 5/2020 | Patel et al. |
| 2020/0146743 A1 | 5/2020 | Defosset et al. |
| 2020/0146744 A1 | 5/2020 | Defosset et al. |
| 2020/0179033 A1 | 6/2020 | Benamou et al. |
| 2020/0214762 A1 | 7/2020 | Pellegrino et al. |
| 2020/0281646 A1 | 9/2020 | Pellegrino et al. |
| 2020/0390493 A1 | 12/2020 | Orczy-Timko et al. |
| 2020/0405499 A1 | 12/2020 | Gerbec et al. |
| 2021/0022814 A1 | 1/2021 | Crawford et al. |
| 2021/0077170 A1 | 3/2021 | Wiersdorf et al. |
| 2021/0093373 A1 | 4/2021 | Dastjerdi et al. |
| 2021/0113238 A1 | 4/2021 | Donovan et al. |
| 2021/0145416 A1 | 5/2021 | Godara et al. |
| 2021/0177502 A1 | 6/2021 | Wright et al. |
| 2021/0290254 A1 | 9/2021 | Serrahima Tornel et al. |
| 2021/0361350 A1 | 11/2021 | Pellegrino et al. |
| 2021/0361351 A1 | 11/2021 | Pellegrino et al. |
| 2021/0369323 A1 | 12/2021 | Edidin |
| 2021/0386491 A1 | 12/2021 | Shmayahu et al. |
| 2021/0401496 A1 | 12/2021 | Purdy et al. |
| 2022/0022930 A1 | 1/2022 | Brockman et al. |
| 2022/0031390 A1 | 2/2022 | Ebersole et al. |
| 2022/0096143 A1 | 3/2022 | Godara et al. |
| 2022/0110639 A1 | 4/2022 | Brockman et al. |
| 2022/0192702 A1 | 6/2022 | Donovan et al. |
| 2022/0192722 A1 | 6/2022 | Harshman et al. |
| 2022/0202471 A1 | 6/2022 | Schepis et al. |
| 2022/0218411 A1 | 7/2022 | Druma et al. |
| 2022/0218434 A1 | 7/2022 | Druma |
| 2022/0240916 A1 | 8/2022 | Jung et al. |
| 2022/0296255 A1 | 9/2022 | Patel et al. |
| 2022/0401114 A1 | 12/2022 | Marino et al. |
| 2023/0046328 A1 | 2/2023 | Weitzman et al. |
| 2023/0138303 A1 | 5/2023 | Pellegrino et al. |
| 2023/0172656 A1 | 6/2023 | Druma |
| 2023/0255676 A1 | 8/2023 | Donovan et al. |

FOREIGN PATENT DOCUMENTS

| | | |
|---|---|---|
| EP | 0584959 | 3/1994 |
| EP | 0597463 | 5/1994 |
| EP | 0880938 | 12/1998 |
| EP | 1013228 | 6/2000 |
| EP | 1059067 | 12/2000 |
| EP | 1059087 | 12/2000 |
| EP | 1652486 A1 | 5/2006 |
| EP | 1641406 B1 | 3/2007 |
| EP | 1294323 B1 | 4/2007 |
| EP | 1938765 A1 | 7/2008 |
| EP | 1471836 B1 | 4/2010 |
| EP | 1968472 B1 | 2/2013 |
| EP | 1824424 B1 | 1/2014 |
| EP | 2785260 | 8/2015 |
| EP | 2965782 | 1/2016 |
| EP | 2508225 | 9/2016 |
| EP | 3078395 | 10/2016 |
| EP | 2205313 B1 | 11/2016 |
| EP | 3097946 | 11/2016 |
| EP | 2913081 | 1/2017 |
| EP | 2590579 B1 | 8/2019 |
| JP | 53-139791 | 11/1978 |
| JP | 6-47058 | 2/1994 |
| JP | 10-290806 | 11/1998 |
| JP | 2001-037760 | 2/2001 |
| JP | 2005-169012 | 6/2005 |
| WO | WO96/36289 | 11/1996 |
| WO | WO98/27876 | 7/1998 |
| WO | WO98/34550 | 8/1998 |
| WO | WO99/19025 | 4/1999 |
| WO | WO99/44519 | 9/1999 |
| WO | WO99/48621 | 9/1999 |
| WO | WO00/21448 | 4/2000 |
| WO | WO00/33909 | 6/2000 |
| WO | WO00/49978 | 8/2000 |
| WO | WO00/56237 | 9/2000 |
| WO | WO00/67648 | 11/2000 |
| WO | WO00/67656 | 11/2000 |
| WO | WO01/01877 | 1/2001 |
| WO | WO01/45579 | 6/2001 |
| WO | WO01/57655 | 8/2001 |
| WO | WO 2002/05699 | 1/2002 |
| WO | WO 2002/05897 | 1/2002 |
| WO | WO 2002/026319 | 4/2002 |
| WO | WO 2002/28302 | 4/2002 |
| WO | WO 2002/054941 | 7/2002 |
| WO | WO 2002/067797 | 9/2002 |
| WO | WO 2002/096304 | 12/2002 |
| WO | WO 2006/044794 | 4/2006 |
| WO | WO 2007/001981 | 1/2007 |
| WO | WO2007/008954 | 1/2007 |
| WO | WO 2007/031264 | 3/2007 |
| WO | WO 2008/001385 | 1/2008 |
| WO | WO 2008/008522 | 1/2008 |
| WO | WO 2008/076330 | 6/2008 |
| WO | WO 2008/076357 | 6/2008 |
| WO | WO 2008/121259 | 10/2008 |
| WO | WO 2008/140519 | 11/2008 |
| WO | WO 2008/141104 | 11/2008 |
| WO | WO2008/144709 | 11/2008 |
| WO | WO 2009/042172 | 4/2009 |
| WO | WO 2009/076461 | 6/2009 |
| WO | WO 2009/124192 | 10/2009 |
| WO | WO 2009/155319 | 12/2009 |
| WO | WO 2010/036865 | 4/2010 |
| WO | WO 2010/111246 | 9/2010 |
| WO | WO 2010/135606 | 11/2010 |
| WO | WO 2011/041038 | 4/2011 |
| WO | WO 2012/024162 | 2/2012 |
| WO | WO 2012/065753 | 3/2012 |
| WO | WO 2012/074932 | 6/2012 |
| WO | WO 2013/009516 | 1/2013 |
| WO | WO 2013/134452 | 9/2013 |
| WO | WO 2013/168006 | 11/2013 |
| WO | WO 2013/180947 | 12/2013 |
| WO | WO 2014/004051 | 1/2014 |
| WO | WO 2014/130231 | 8/2014 |
| WO | WO 2014/141207 | 9/2014 |
| WO | WO 2014/165194 | 10/2014 |
| WO | WO 2014/176141 | 10/2014 |
| WO | WO 2015/038317 | 3/2015 |
| WO | WO 2015/047817 | 4/2015 |
| WO | WO 2015/066295 | 5/2015 |
| WO | WO 2015/066303 | 5/2015 |

(56) References Cited

FOREIGN PATENT DOCUMENTS

| | | |
|---|---|---|
| WO | WO 2015/079319 | 6/2015 |
| WO | WO 2015/148105 | 10/2015 |
| WO | WO 2014/145222 | 1/2016 |
| WO | WO 2014/145659 | 1/2016 |
| WO | WO 2014/146029 | 1/2016 |
| WO | WO 2016/033380 | 3/2016 |
| WO | WO 2016/048965 | 3/2016 |
| WO | WO 2014/197596 | 4/2016 |
| WO | WO 2014/210373 | 5/2016 |
| WO | WO 2016/069157 | 5/2016 |
| WO | WO 2016/075544 | 5/2016 |
| WO | WO 2015/024013 | 6/2016 |
| WO | WO 2016/090420 | 6/2016 |
| WO | WO 2016/105448 | 6/2016 |
| WO | WO 2016/105449 | 6/2016 |
| WO | WO 2015/044945 | 8/2016 |
| WO | WO 2015/057696 | 8/2016 |
| WO | WO 2015/060927 | 8/2016 |
| WO | WO 2016/127130 | 8/2016 |
| WO | WO 2016/130686 | 8/2016 |
| WO | WO 2016/134273 | 8/2016 |
| WO | WO 2011/157714 | 9/2016 |
| WO | WO 2016/148954 | 9/2016 |
| WO | WO 2016/154091 | 9/2016 |
| WO | WO 2016/168381 | 10/2016 |
| WO | WO 2016/209682 | 12/2016 |
| WO | WO 2017/009472 | 1/2017 |
| WO | WO2017/010930 | 1/2017 |
| WO | WO 2017/019863 | 2/2017 |
| WO | WO 2017/027703 | 2/2017 |
| WO | WO 2017/027809 | 2/2017 |
| WO | WO 2018/116273 | 6/2018 |
| WO | WO 2020/198150 | 10/2020 |
| WO | WO 2021/016699 A1 | 2/2021 |
| WO | WO 2022/066743 A2 | 3/2022 |
| WO | WO 2022/125875 A1 | 6/2022 |
| WO | WO 2022/191978 A1 | 9/2022 |
| WO | WO 2022/207105 A1 | 10/2022 |
| WO | WO 2023/009697 A1 | 2/2023 |

OTHER PUBLICATIONS

Antonacci M. Darryl et al.; Innervation of the Human Vertebral Body: A Histologic Study; Journal of Spinal Disorder vol. 11 No. 6 pp. 526-531 1998 Lippincott Williams & Wilkins Philadelphia.

Arnoldi Carl C.; Intraosseous Hypertension—A Possible Cause of Low Back Pain?; Clinical Orthopedics and Related Research No. 115 Mar.-Apr. 1976.

Bailey, Jeannie F., "Innervation Patterns of PGP 9.5-Positive Nerve Fibers within the Human Lumbar Vertebra," Journal of Anatomy, (2011) 218, pp. 263-270, San Francisco, California.

Becker, Stephan, et al., "Ablation of the basivertebral nerve for treatment of back pain: a clinical study," The Spine Journal, vol. 17, pp. 218-223 (Feb. 2017).

Bergeron et al. "Fluoroscopic-guided radiofrequency ablation of the basivertebral nerve: application and analysis with multiple imaging modalities in an ovine model" Thermal Treatment of Tissue: Energy Delivery and Assessment III edited by Thomas P. Ryan Proceedings of SPIE vol. 5698 (SPIE Bellingham WA 2005) pp. 156-167.

Bogduk N. The anatomy of the lumbar intervertebral disc syndrome Med J. Aust. 1976 vol. 1 No. 23 pp. 878-881.

Bogduk Nikolai et al.; Technical Limitations to the efficacy of Radiofrequency Neurotomy for Spinal Pain; Neurosurgery vol. 20 No. 4 1987.

Caragee, EG et al.; "Discographic, MRI and psychosocial determinants of low back pain disability andremission: A prospective study in subjects with benign persistent back pain", The Spine Journal: The Official Journal of the North American Spine Society, vol. 5(1), pp. 24-35 (2005).

Choy Daniel SS.J et al.; Percutaneous Laser Disc Decompression A New Therapeutic Modality; SPINE vol. 17 No. 8 1992.

Cosman E.R. et al. Theoretical Aspects of Radiofrequency Lesions in the Dorsal Root Entry Zone. Neurosurgery vol. 1 No. 6 1984 pp. 945-950.

Deardorff Dana L. et al.; Ultrasound applicators with internal cooling for interstitial thermal therapy; SPIE vol. 3594 1999.

Deramond H. et al. Temperature Elevation Caused by Bone Cement Polymerization During Vertebroplasty Bone Ang. 1999 pp. 17S-21S vol. 25 No. 2 Supplement.

Diederich C. J. et al. "IDTT Therapy in Cadaveric Lumbar Spine: Temperature and thermal dose distributions Thermal Treatment of Tissue: Energy Delivery and Assessment" Thomas P. Ryan Editor Proceedings of SPIE vol. 4247:104-108 (2001).

Diederich Chris J. et al., Ultrasound Catheters for Circumferential Cardiac Ablation; SPIE vol. 3594 (1999).

Dupuy D.E. et al. Radiofrequency ablation of spinal tumors: Temperature distribution in the spinal canal AJR vol. 175 pp. 1263-1266 Nov. 2000.

Dupuy Damian E.; Radiofrequency Ablation: An Outpatient Percutaneous Treatment; Medicine and Health/Rhode Island vol. 82 No. Jun. 6, 1999.

Esses Stephen I. et al.; Intraosseous Vertebral Body Pressures; SPINE vol. 17 No. 6 Supplement 1992.

FDA Response to 510(k) Submission by Relievant Medsystems Inc. submitted on Sep. 27, 2007 (date stamped on Oct. 5, 2007) and associated documents.

Fields, AJ et al; "Innervation of pathologies in the lumbar vertebral endplate and intervertebral disc", The Spine Journal: Official Journal of the North American Spine Society, vol. 14(3), pp. 513-521 (2014).

Fields, Aaron J. et al.; "Cartilage endplate damage strongly assocates with chronic low back pain, independent of modic changes", Abstract form Oral Presentation at the ISSLS Annual Meeting in Banff, Canada (May 14-18, 2018).

Fischgrund JS, et al.; "Intraosseous Basivertebral Nerve Ablation for the Treatment of Chronic Low Back Pain: 2-Year Results from a Prospective Randomized Double-Blind Sham-Controlled Multicenter Study", International Journal of Spine Surgery, vol. 13 (2), pp. 110-119 (2019).

Fras M.D., Christian et al., "Substance P-containing Nerves within the Human Vertebral Body: An Immunohistochemical Study of the Basivertebral Nerve", The Spine Journal 3, 2003, pp. 63-67.

Gehl J. "Electroporation: theory and methods perspectives for drug delivery gene therapy and research" Acta Physiol. Scand. vol. 177 pp. 437-447 (2003).

Goldberg S.N. et al. Tissue ablation with radiofrequency: Effect of probe size gauge duration and temperature on lesion volume Acad. Radiol. vol. 2 pp. 399-404 (1995).

Gornet, Matthew G et al.; "Magnetic resonance spectroscopy (MRS) can identify painful lumbar discs and may facilitate improved clinical outcomes of lumbar surgeries for discogenic pain", European Spine Journal, vol. 28, pp. 674-687 (2019).

Hanai Kenji et al.; Simultaneous Measurement of Intraosseous and Cerebrospinal Fluid Pressures in the Lumbar Region; SPINE vol. 10 No. 1 1985.

Heggeness Michael H. et al. The Trabecular Anatomy of Thoracolumbar Vertebrae: Implications for Burst Fractures Journal of Anatomy 1997 pp. 309-312 vol. 191 Great Britain.

Heggeness Michael H. et al. Discography Causes End Plate Deflection; SPINE vol. 18 No. 8 pp. 1050-1053 1993 J.B. Lippincott Company.

Heggeness, M. et al Ablation of the Basivertebral Nerve for the Treatment of Back Pain: A Pilot Clinical Study; The Spine Journal, 2011, vol. 11, Issue 10, Supplement, pp. S65-S66, ISSN 1529-9430.

Hoopes et al. "Radiofrequency Ablation of The Basivertebral Nerve as a Potential Treatment of Back Pain: Pathologic Assessment in an Ovine Model" Thermal Treatment of Tissue: Energy Delivery and Assessment III edited by Thomas P. Ryan Proceedings of SPIE vol. 5698 (SPIE Bellingham WA 2005) pp. 168-180.

Houpt Jonathan C. et al.; Experimental Study of Temperature Distributions and Thermal Transport During Radiofrequency Current Therapy of the Intervertebral Disc; SPINE vol. 21 No. 15 pp. 1808-1813 1996 Lippincott-Raven Publishers.

(56) References Cited

OTHER PUBLICATIONS

Jourabchi, Natanel et al.; "Irreversible electroporation (NanoKnife) in cancer treatment," Gastrointestinal Intervention, vol. 3, pp. 8-18 (2014).
Khalil, J et al.; "A Prospective, Randomized, Multi-Center Study of Intraosseous Basivertebral Nerve Ablation for the Treatment of Chronic Low Back Pain", The Spine Journal (2019), avilable at https://doi.org/10.1016/jspinee.2019.05.598.
Kleinstueck Frank S. et al.; Acute Biomechanical and Histological Effects of Intradiscal Electrothermal Therapy on Human Lumbar Discs; SPINE vol. 26 No. 20 pp. 2198-2207; 2001 Lippincott Williams & Wilkins Inc.
Kopecky Kenyon K. et al. "Side-Exiting Coaxial Needle for Aspiration Biopsy"—AJR—1996; 167 pp. 661-662.
Kuisma M et al.; "Modic changes in endplates of lumbar vertebral bodies: Prevalence and association with low back and sciatic pain among middle-aged male workers", Spine, vol. 32(10), pp. 1116-1122 (2007).
Lehmann Justus F. et al.; Selective Heating Effects of Ultrasound in Human Beings; Archives of Physical Medicine & Rehabilitation Jun. 1966.
Letcher Frank S. et al.; The Effect of Radiofrequency Current and Heat on Peripheral Nerve Action Potential in the Cat; U.S. Naval Hospital Philadelphia PA. (1968).
Lotz JC, et al.; "The Role of the Vertebral End Plate in Low Back Pain", Global Spine Journal, vol. 3, pp. 153-164 (2013).
Lundskog Jan; Heat and Bone Tissue-/an experimental investigation of the thermal properties of bone tissue and threshold levels for thermal injury; Scandinavian Journal of Plastic and Reconstructive Surgery Supplemental 9 From the Laboratory of Experimental Biology Department of anatomy University of Gothenburg Gothenburg Sweden GOTEBORG 1972.
Martin J.B. et al. Vertebroplasty: Clinical Experience and Follow-up Results Bone Aug. 1999 pp. 11S-15S vol. 25 No. 2 Supplement.
Massad Malek M.D. et al.; Endoscopic Thoracic Sympathectomy: Evaluation of Pulsatile Laser Non-Pulsatile Laser and Radiofrequency-Generated Thermocoagulation; Lasers in Surgery and Medicine; 1991; pp. 18-25.
Mehta Mark et al.; The treatment of chronic back pain; Anaesthesia 1979 vol. 34 pp. 768-775.
Modic MT et al.; "Degenerative disk disease: assessment of changes in vertebral body marrow with MR imaging" Radiology vol. 166 pp. 193-199 (1988).
Mok, Florence et al.; "Modic changes of the lumbar spine: Prevalence, risk factors, and association with disc degeneration and low back pain in a large-scale population-based cohort", The Spine Journal: Official Journal of the North American Spine Society, vol. 16(1), pp. 32-41 (2016).
Nau William H. Ultrasound interstitial thermal therapy (USITT) in the prostate; SPIE vol. 3594 Jan. 1999.
Osteocool Pain Management Brochure, Baylis Medical, copyright 2011.
Pang, Henry et al,; The UTE Disc Sign on MRI; A Novel Imaging Biomarker Associated With Degenerative Spine Changes, Low Back Pain, and Disability, SPINE, vol. 42 (Aug. 2017).
Radiological Society of North America. "Pulsed radiofrequency relieves acute back pain and sciatica." ScienceDaily. ScienceDaily, Nov. 27, 2018. <www.sciencedaily.com/releases/2018/11/181127092604.htm>.
Rashbaum Ralph F.; Radiofrequency Facet Denervation A Treatment alternative in Refractory Low Back Pain with or without Leg Pain; Orthopedic Clinics of North America—vol. 14 No. Jul. 3, 1983.
Rosenthal D.I. Seminars in Musculoskeletal Radiology vol. 1 No. 2. pp. 265-272 (1997).
Ryan et al. "Three-Dimensional Finite Element Simulations of Vertebral Body Thermal Treatment"Thermal Treatment of Tissue: Energy Delivery and Assessment III edited by Thomas P. Ryan Proceedings of SPIE vol. 5698 (SPIE Bellingham WA 2005) pp. 137-155.
Shealy C. Norman; Percutaneous radiofrequency denervation of spinal facets Treatment for chronic back pain and sciatica; Journal of Neurosurgery/vol. 43/Oct. 1975.
Sherman Mary S.; The Nerves of Bone The Journal of Bone and Joint Surgery Apr. 1963 pp. 522-528 vol. 45-A No. 3.
Solbiati L. et al. Hepatic metastases: Percutaneous radio-frequency ablation with cooled-tip electrodes. Interventional Radiology vol. 205 No. 2 pp. 367-373 (1997).
Stanton Terry "Can Nerve Ablation Reduce Chronic Back Pain?" AAOS Now Jan. 2012.
The AVAmax System—Cardinal Health Special Procedures Lit. No. 25P0459-01—www.cardinal.com (copyright 2007).
Tillotson L. et al. Controlled thermal injury of bone: Report of a percutaneous technique using radiofrequency electrode and generator. Investigative Radiology Nov. 1989 pp. 888-892.
Troussier B. et al.; Percutaneous Intradiscal Radio-Frequency Thermocoagulation A Cadaveric Study; SPINE vol. 20 No. 15 pp. 1713-1718 1995 Lippincott-Raven Publishers.
Ullrich Jr. Peter F. "Lumbar Spinal Fusion Surgery" Jan. 9, 2013 Spine-Health (available via wayback machine Internet archive at http://web.archive.org/web/20130109095419/http://www/spine-health.com/treatment/spinal-fusion/lumbar-spinal-fusion-surgery).
Weishaupt, D et al,; "Painful Lumbar Disk Derangement: Relevance of Endplate Abnormalities at MR Imaging", Radiology, vol. 218(2), pp. 420-427 (2001).
YouTube Video, "DFINE-STAR Procedure Animation," dated Sep. 30, 2013, can be viewed at https://www.youtube.com/watch?v=YxtKNyc2e-0.
Kim et al., Transforaminal epiduroscopic basivertebral nerve laser ablation for chronic low back pain associated with modic changes: A preliminary open-label study. Pain Research and Management 2018; https://pubmed.ncbi.nlm.nih.gov/30186540.
Rahme et al., The modic vertebral endplate and marrow changes: pathologic significance and relation to low back pain and segmental instability of the lumbar spine. American Journal of Neuroradiology 29.5 (2008): 838-842; http://www.ajnr.org/content/29/5/838.
Macadaeg et al., A prospective single arm study of intraosseous basivertebral nerve ablation for the treatment of chronic low back pain: 12-month results. North American Spine Society Journal; May 27, 2020, 8 pages.
Vadala et al., "Robotic Spine Surgery and Augmented Reality Systems: A State of the Art", Neurospine Epub Mar. 31, 2020; revised: Feb. 22, 2020; accepted: Feb. 24, 2020; retrieved on [Oct. 6, 2022]. Retrieved from the internet URL:https://www.ncbi.nlm.nih.gov/pmc/articles/PMC7136092/pdf/ns-2040060-030.pdf entire document.

* cited by examiner

METHODS OF DENERVATING VERTEBRAL BODY USING EXTERNAL ENERGY SOURCE

CROSS-REFERENCE TO RELATED APPLICATIONS

This application is a continuation of U.S. patent application Ser. No. 16/205,050, filed Nov. 29, 2018, now issued as U.S. Pat. No. 11,471,210, which is a continuation of U.S. patent application Ser. No. 14/369,661, filed Jun. 27, 2014, now issued as U.S. Pat. No. 10,390,877, which is a 371 U.S. national phase entry of International Application No. PCT/US2012/071465, filed Dec. 21, 2012, which claims the benefit of U.S. Provisional Application No. 61/582,170 filed Dec. 30, 2011 and U.S. Provisional Application No. 61/582,165 filed Dec. 30, 2011, the entire contents of each of which are hereby expressly incorporated herein by reference.

FIELD

Various embodiments of the invention pertain generally to methods and systems for therapeutic treatment of pain, and more particularly to therapeutic treatment of back pain.

BACKGROUND

Body pain may originate in muscles, organs, bones, or other areas of the body. One example of body pain is back pain, or pain associated with the spine. Back pain is a huge health problem worldwide and is the cause of much human suffering. Back pain is also a major cause for work-related disability benefits and compensation. Treatments for back pain vary widely, ranging from physical therapy, to pharmacological therapy and pain management, to surgical intervention.

Use of pharmaceuticals to treat back pain has at least three concerns. First, the patient may become dependent upon the pharmaceuticals. Second, the cost of the pharmaceuticals, usually over several years, may be extremely costly. Third, generally, the pain persists over many years.

Surgery also presents several concerns. First, most techniques involve fusing the vertebrae of the spine together and/or removing tissue from between the vertebrae. While surgery usually provides long-term relief, e.g., greater than one-year, surgical techniques require extensive recovery time and additional physical therapy for the patient.

While physical therapy does not present all of the concerns of surgery or using pharmaceuticals, patients receive varying degrees of relief from pain. Additionally, physical therapy usually provides only short-term pain relief, e.g., one to two months, thereby extending treatment over several years, and thus increasing the cost of treatment. Moreover, 1 many patients ultimately require surgery.

SUMMARY

Several embodiments of the invention are directed to a method for treating back pain associated with a vertebral body of a patient, wherein the vertebral body is innervated by a basivertebral nerve having an origin at a medial branch of a sinuvertebral nerve and that courses medially under the posterior longitudinal ligament to enter the vertebral body at a basivertebral foramen of the vertebral body. In some embodiments, the method comprises identifying at least a portion of a basivertebral nerve associated with the vertebral body and isolating the basivertebral nerve at a location external to the vertebral body. In some embodiments, the method comprises modulating (e.g., denervating, temporarily or permanently blocking nerve conduction, altering a conductive property, stimulating, severing, cutting, crimping, heating, cooling, radiating, agitating, or altering the chemical composition of) the basivertebral nerve at the external location to treat pain associated with the vertebral body.

Several embodiments of the invention are directed to a method for treating back pain associated with a vertebral body of a patient. In some embodiments, the method comprises percutaneously guiding a delivery device within or near the vertebral body. In some embodiments, the method comprises identifying at least a portion of a basivertebral nerve associated with the vertebral body and isolating the basivertebral nerve at a location external to the vertebral body. In some embodiments, the method comprises delivering a treatment device to the external location using the delivery device and operating the treatment device at the external location. In some embodiments, the operation of the treatment device is configured to modulate the basivertebral nerve at the external location to treat pain associated with the vertebral body. In one embodiment, the delivery device comprises a catheter comprising a first lumen for advancing an imaging device and a second lumen for advancing the treatment device.

In some embodiments, the basivertebral nerve comprises a medial branch of a sinuvertebral nerve, wherein the basivertebral nerve emanates at a first end at a junction of the sinuvertebral nerve and wherein the basivertebral nerve courses medially from the junction under the posterior longitudinal ligament. In some embodiments, the basivertebral nerve enters the vertebral body at a second end located at a basivertebral foramen of the vertebral body. Modulation of the basivertebral nerve may be performed at a location on the basivertebral nerve at or near the second end located within the basivertebral foramen.

In some embodiments, identifying at least a portion of the basivertebral nerve comprises locating the sinuvertebral nerve and locating the junction of the basivertebral nerve with the sinuvertebral nerve. In one embodiment, modulating the basivertebral nerve comprises modulating the basivertebral nerve at a location on the basivertebral nerve at or near the junction with the sinuvertebral nerve. In one embodiment, the method comprises verifying that the basivertebral nerve courses medially under the posterior longitudinal ligament prior to modulating the basivertebral nerve. In some embodiments, the posterior longitudinal ligament is dilated to allow visualization of the basivertebral foramen prior to modulation of the basivertebral nerve.

In several embodiments, isolating the basivertebral nerve comprises following the basivertebral nerve from the junction medially under the posterior longitudinal ligament and dilating a space under the posterior longitudinal ligament to visualize the basivertebral foramen. In one embodiment, the method comprises locating the basivertebral foramen via direct visualization with an imaging device and modulating the basivertebral nerve at a location on the basivertebral nerve at or near the second end located within the basivertebral foramen.

In some embodiments, the step of modulating the basivertebral nerve comprises positioning an energy delivery device into the basivertebral foramen and directing a field of energy into the basivertebral foramen to denervate the basivertebral nerve, wherein the directed energy field is focused to be confined in a first direction into the basivertebral foramen. In some embodiments, the step of identifying at least a portion of the basivertebral nerve comprises locating the sinuvertebral nerve via direct visualization with an imaging device and locating the junction of the basivertebral nerve with the sinuvertebral nerve.

Several embodiments of the invention are directed to a system for treating back pain associated with a vertebral body of a patient. The system may comprise a delivery assembly configured to be percutaneously delivered to a treatment region adjacent the vertebral body. The delivery assembly may comprise a catheter having one or more lumens and an energy delivery device configured to be advanced within one of the catheter lumens. In some embodiments, the energy delivery device is sized to allow positioning of a distal end of the energy delivery device at a treatment region (such as the origin of the basivertebral nerve with the sinuvertebral nerve, or into the basivertebral foramen). In one embodiment, the energy delivery device comprises an energy delivery element configured to direct a focused field of energy (e.g., for focusing energy into the basivertebral foramen to modulate the basivertebral nerve) such that the directed energy field is focused to be confined in a first 3 direction into the basivertebral foramen.

In some embodiments, the energy delivery element is configured to emit therapeutic energy radially outward from the distal end of the energy delivery device while substantially shielding energy delivery toward a proximal end of the energy delivery device. In some embodiments, the delivery assembly comprises an imaging device (e.g., visualization scope or camera) to aid in visualization of the basivertebral foramen and delivery of the energy delivery device into the basivertebral foramen. In one embodiment, the delivery assembly comprises an aspirating device to be delivered under the posterior longitudinal ligament via the one ore more lumens of the catheter. The aspiration device may be configured to dilate a space under the posterior longitudinal ligament to aid in visualization of the basivertebral foramen.

Several embodiments of the invention are directed to a method for denervating a basivertebral nerve to treat back pain using an externally positioned energy source (e.g., radiation, ultrasound, microwave source). The energy source may comprise a plurality of sources. The plurality of sources may be configured to deliver different energy modalities and/or deliver energy at different times. In one embodiment, the method includes acquiring imaging data of the vertebra. In one embodiment, the method comprises determining a target treatment site within or near the vertebra based on the acquired imaging data that corresponds to a location of a basivertebral nerve associated with pain in the vertebral body. In one embodiment, the step of determining a target treatment site is performed visually without acquiring imaging data. In one embodiment, the method comprises positioning a focal point of an external energy source to substantially coincide with the target treatment site. The target treatment site may be within or outside the vertebral body. The target treatment site may correspond to a location of a basivertebral nerve associated with pain in the vertebral body. In several embodiments, the target treatment site is a location within a basivertebral foramen of the vertebral body.

In one embodiment, the external energy source is positioned at a location external to the body of a patient. In one embodiment, the method comprises delivering a treatment dose of therapeutic energy at the target treatment site, wherein the treatment dose is configured to modulate (e.g., denervate, temporarily or permanently block or eliminate nerve conduction, alter a conductive property, stimulate, heat, cool, radiate, agitate, disrupt, ablate, or alter the chemical composition of) the basivertebral nerve.

In one embodiment, the method comprises acquiring patient feedback prior to delivering the treatment dose (e.g., using one or more sensors or monitors or through 4 conversation with the patient). In one embodiment, acquiring patient feedback comprises delivering an identification dose that is a lesser dose than the treatment dose to the target treatment site and eliciting feedback from the patient with respect to a change in the sensation of pain. The identification dose may be prescribed such that the identification dose temporarily alters the sensation of pain experienced by the patient. In one embodiment, the method comprises modifying the target treatment site or location according to the acquired feedback.

Treatment may be delivered to the target treatment site to modulate at least a portion of the basivertebral nerve (e.g., terminus or junction or a portion of the basivertebral nerve between the terminus or junction and the posterior wall). In one embodiment, a portion of the basivertebral nerve is modulated by delivering focused energy (e.g., radiation, acoustic or ultrasonic energy) to an isolated region of the basivertebral nerve. In one embodiment, the focused energy is high-intensity focused ultrasonic energy. In another embodiment, a portion of the basivertebral nerve is modulated by delivering an agent to the treatment region to isolate treatment to that region. In accordance with several embodiments of the invention, the treatment is advantageously focused on a location of the basivertebral nerve that is upstream of one or more branches of the basivertebral nerve.

In some embodiments, delivering the treatment dose comprises delivering a first incremental dose that is a fraction of the treatment dose and then acquiring imaging data of the patient. The method may comprise measuring the distance between the focal point of the energy source and the target treatment site and then moving the external energy source such that the focal point of the external energy source coincides with the target treatment site if the measured distance is not within a predetermined threshold. In some embodiments, delivering the treatment does comprises delivering a second incremental dose if the measured distance is within the predetermined threshold.

Nerves within bones other than the vertebrae or spine may be targeted by the external energy source, for example, non-spinal joints or in non-orthopedic applications (e.g., cardiac, pulmonary, renal, or treatment of other organs and/or their surrounding nerves). The external energy source may comprise at least one radiation source or at least one acoustic energy source. In one embodiment, the at least one acoustic energy source comprises one or more transducers configured to deliver focused ultrasonic energy (e.g., high-intensity focused ultrasonic energy or low-intensity focused ultrasonic energy). In one embodiment, the external energy source comprises at least one microwave source.

In some embodiments, the step of determining a target treatment site 5 comprises acquiring a vertebral reference point corresponding to a radiographically identifiable anatomical feature of the vertebra and generating coordinates for the target treatment site as a function of a calculated distance from the vertebral reference point. In one embodiment, the calculated distance corresponds to a predicted basivertebral nerve location that is obtained from analysis of the acquired imaging data.

In some embodiments, the step of acquiring imaging data comprises restraining at least a portion of the patient to an external support. In one embodiment, the external support comprises a radiographically identifiable marker. Acquiring imaging data may comprise imaging the patient and locating the radiographically identifiable marker within the acquired image. The method may comprise assigning an external reference point corresponding to the location of the radiographically identifiable marker. In one embodiment, the external reference point is as a base point for positioning the focal point of the external energy source at the target treatment site. In one embodiment, the method comprises acquiring a vertebral reference point corresponding to a radiographically identifiable anatomical feature of the vertebra and generating coordinates for the target treatment site as a function of a calculated distance from the vertebral reference point. In some embodiments, the step of determining a target treatment site is performed by direct visualization without calculations based on acquired imaging data.

Several embodiments of the invention are directed to a system for treating back pain associated with the spine (e.g., one or more vertebrae) of a patient. In several embodiments, the system provides non-invasive treatment of the back pain by modulating spinal nerves (e.g., intraosseous or basivertebral nerves) from outside the body. In some embodiments, the system comprises an external energy (e.g., radiation) source configured to be positioned at a location external to the body of the patient. In one embodiment, the system comprises a linear drive configured to drive translation of the external energy source with respect to the patient in one or more axes. In one embodiment, the system comprises a computer coupled to the external energy source and to the linear drive. In one embodiment, the system comprises programming instructions executable on the computer. In several embodiments, the programming instructions comprise one or more modules for performing one or more of the following: determining a target treatment site within or near the spine (e.g., vertebral body) based on acquired imaging data or based on direct visualization; controlling the linear drive to position a focal point of the external energy source to substantially coincide with a target treatment site that corresponds to a location of a basivertebral nerve associated with pain in the spine (e.g., vertebral body); and controlling the 6 external energy source to deliver a treatment dose of therapeutic energy at the target treatment site. In several embodiments, the treatment dose is configured to modulate (e.g., denervate) the basivertebral nerve. The therapeutic system may include a treatment device and an imaging device. In one embodiment, the treatment device and the imaging device are combined into a single unitary device. The focal point may be adjusted depending on imaging obtained by the imaging device or other feedback mechanisms.

In some embodiments, the system comprises an imaging source coupled to the computer for acquiring imaging data of the spine (e.g., vertebrae or vertebral bodies). In one embodiment, the system comprises a support configured to restrain at least a portion of the patient to an external support. The support may comprise a radiographically identifiable marker. In one embodiment, the executable program instructions are configured to control the imaging source for imaging the patient, locate the radiographically identifiable marker within the acquired image; and assign an external reference point corresponding to the location of the radiographically identifiable marker. The external reference point may be used as a base point for positioning the focal point of the external energy source at the target treatment site.

In some embodiments, the system comprises a radial drive coupled to the external energy source. The radial drive may be configured to rotate the external energy source about the target treatment site during delivery of the treatment dose. The external energy source may comprise one or more radiation-emitting and/or acoustic energy sources having a common focal point or different focal points.

Several embodiments of the invention are directed to a radiotherapy method for treating back pain associated with a vertebral body of a vertebra of a patient. In one embodiment, the method comprises acquiring imaging data of the vertebra and determining a target treatment site within the vertebra based on the acquired imaging data. In one embodiment, the target treatment site corresponds to a location of a basivertebral nerve associated with pain in the vertebral body. The method may further comprise positioning a focal point of an external radiation source to substantially coincide with the target treatment site and delivering a treatment dose of therapeutic energy at the target treatment site to modulate the basivertebral nerve.

Several embodiments of the invention are directed to a radiotherapy system for treating back pain associated with a vertebral body of a patient. In some embodiments, the system comprises an external radiation source configured to be positioned at a location external to the body of the patient. In one embodiment, the system comprises a 7 linear drive coupled to the radiation source, the linear drive configured to drive translation of the radiation source in one or more axes. In some embodiments, the system comprises a computer coupled to the radiation source and to the linear drive. The computer may comprise programming instructions executable on the computer for determining a target treatment site within or near the vertebra based on acquired imaging data, wherein the target treatment site corresponds to a location of a basivertebral nerve associated with pain in the vertebral body. In one embodiment, the programming instructions are further configured to control the linear drive to position a focal point of the external energy source to substantially coincide with the target treatment site and/or to control the external radiation source to deliver a treatment dose of therapeutic energy at the target treatment site. In some embodiments, the treatment dose is configured to modulate the basivertebral nerve at the location.

Further aspects of embodiments of the invention will be discussed in the following portions of the specification. With respect to the drawings, elements from one figure may be combined with elements from the other figures.

BRIEF DESCRIPTION OF THE DRAWINGS

Several embodiments of the invention will be more fully understood by reference to the following drawings which are for illustrative purposes only.

DETAILED DESCRIPTION

In accordance with several embodiments, back pain may be associated with one or more nerves in the spine. For example, one or more intraosseous or basivertebral nerves within one or more vertebrae of the spine may be the source of the back pain. In some embodiments, the nerves are treated (e.g., modulated) at nerve portions that are isolated outside of the bony tissue of the vertebral body (e.g., external to the vertebral body). In some embodiments, the nerves are treated from a location external to the skin (e.g., extracorporeal, non-invasive) treatment.

Identification, Isolation, and Modulation of Basivertebral Nerve

Figure 1:
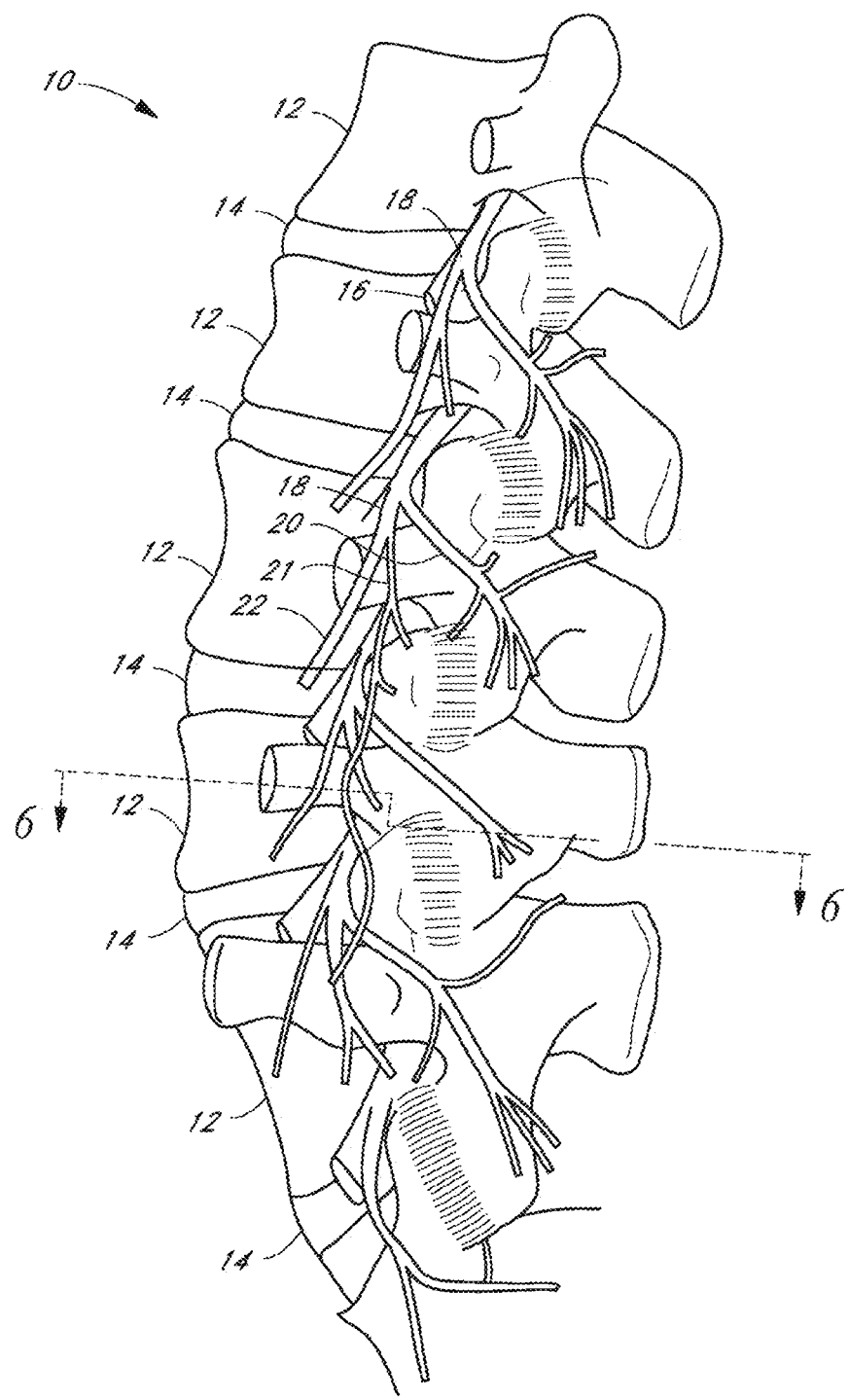
FIG. 1 illustrates a left posterior view of the lumbar spine showing branches of associated nerves.

FIG. 1 illustrates a left posterior view of the lumbar spine 10 showing branches of associated nerves. Spine 10 comprises intervertebral discs 14 disposed between adjacent vertebrae 12. Lumbar dorsal rami 18 branch at nearly right angles from a corresponding ventral ramus 16 at each vertebra 12. The dorsal rami 18 divide into two or three branches: medial branch 20, lateral branch 22, and variable intermediate branch 21.

Figure 2:
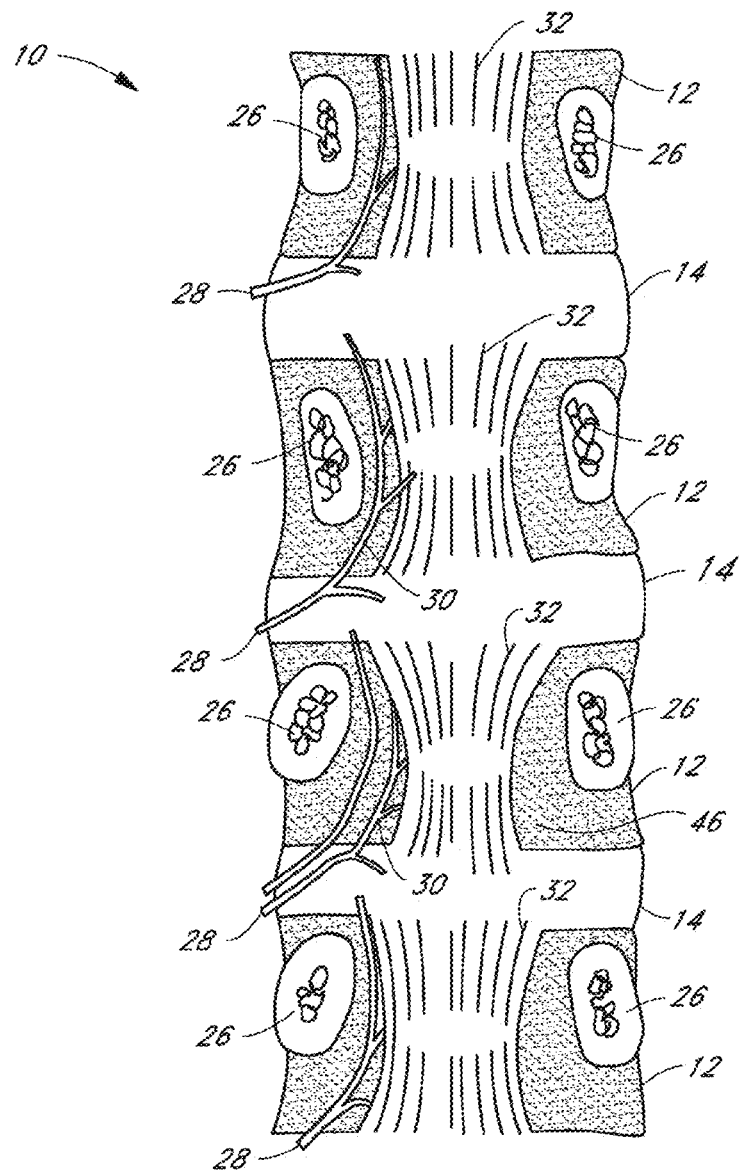
FIG. 2 is a posterior view of the spine, with pedicles transected, dural sac removed to show the path and branches of the left sinuvertebral nerve.
Figure 3:
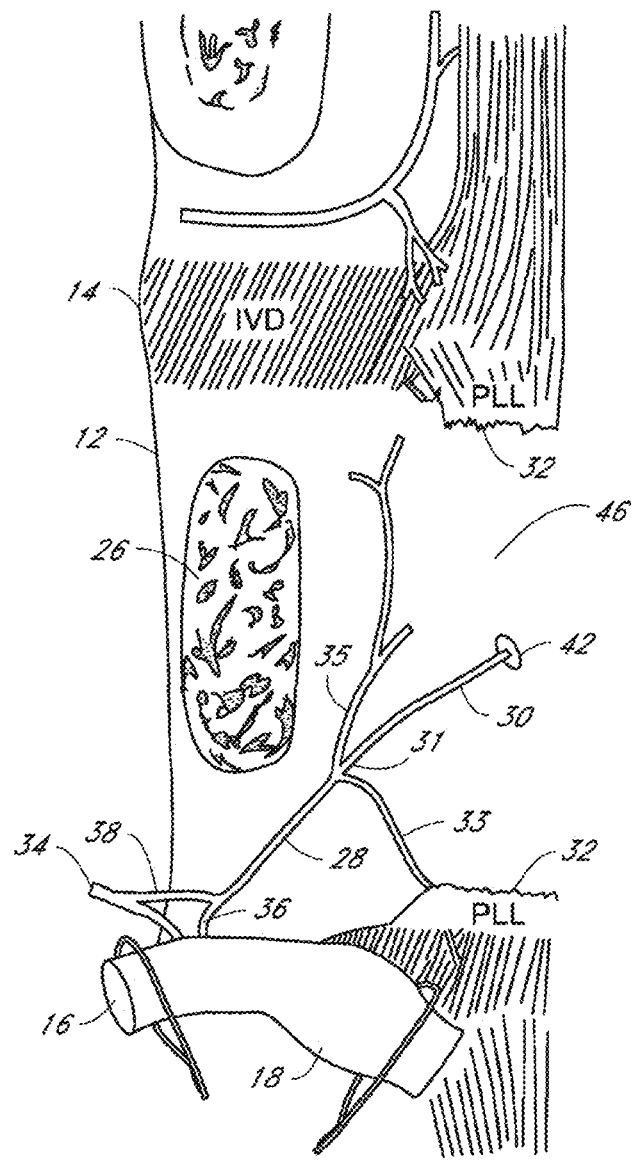
FIG. 3 is a posterior view of the spine, with pedicles transected and dural sac removed, and posterior longitudinal ligament cut out to show the path and branches of the left sinuvertebral nerve.

Referring to FIGS. 2 and 3, the sinuvertebral nerves 28 (left and right) are recurrent branches of the ventral rami 16 that re-enter (e.g., retrograde) the intervertebral foramina 25 to be distributed within the vertebral canal 46. FIG. 2 is a posterior view of the spine 10 with pedicles 26 transected, dural sac removed to show the path and branches of the left sinuvertebral nerve 28 (posterior longitudinal ligament 32 is intact). FIG. 3 is a posterior view of the spine 10 with pedicles 26 transected and dural sac removed, and posterior longitudinal ligament 32 cut out to show the path and branches of the left sinuvertebral nerve 28 and floor of the vertebral canal 46. In FIG. 3, the ventral ramus 16 and dorsal root ganglion 18 are retracted to show the originals of the origin of the sinuvertebral nerve 28.

As shown in FIG. 3, the sinuvertebral nerves 28 are mixed polysegmental nerves and nerve plexuses, each being formed by a somatic root 36 from a ventral ramus 16 and an autonomic root 38 from the grey ramus communicans 34. The lumbar sinuvertebral nerves 28 run across the back of the vertebral body 40, just below the upper pedicle 26. Within the vertebral canal 46, the sinuvertebral nerve 28 forms a major ascending branch 35 travelling nostrally parallel to the posterior longitudinal ligament 32, a lesser descending branch 33, and a larger medial branch 30 that crosses under the posterior longitudinal ligament 32.

In accordance with several embodiments, the medial branch 30 comprises the basivertebral nerve that innervates the vertebral body 40, and is in large part responsible for back pain experienced by a subject (e.g., human or animal patient).

FIG. 3 illustrates a basivertebral nerve 30 that emanates from a trifurcated junction 31 of the sinuvertebral nerve 28, comprising ascending branch 35, descending branch 33 and medial basivertebral nerve branch 30. As seen in FIG. 3, the basivertebral nerve extends from trifurcated junction 31 below the posterior longitudinal ligament 32 and into one of the basivertebral foramina 42. The basivertebral nerve 30 shown in FIG. 3 is the left basivertebral nerve that enters the left-most basivertebral foramen 42. Correspondingly, the right basivertebral nerve (not shown) follows a similar path from under the opposite pedicle 26 and into the right basivertebral foramen 42.

Figure 4:
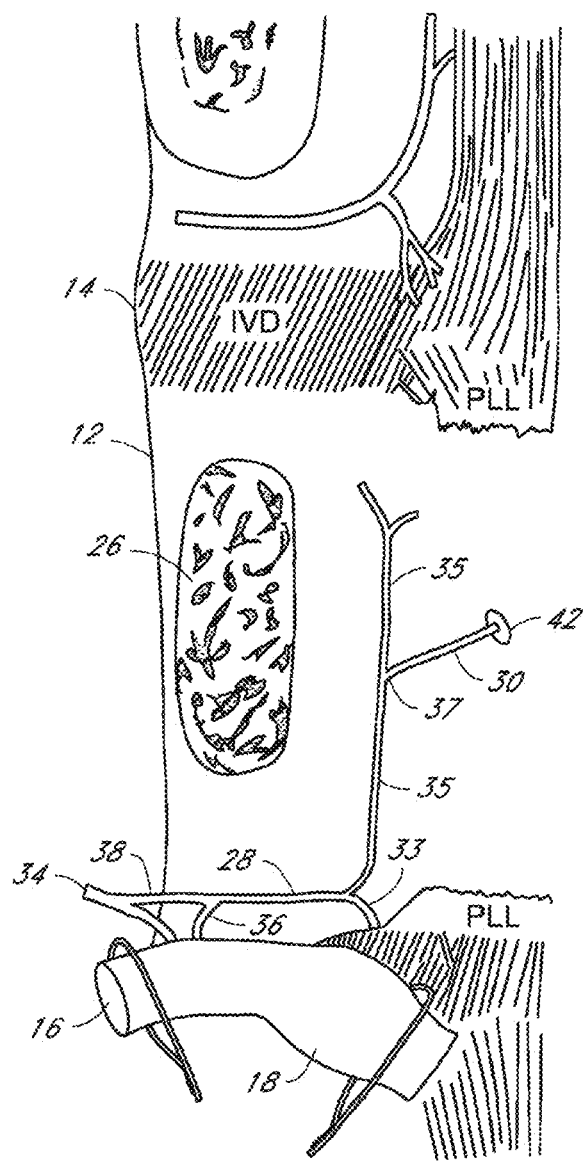
FIG. 4 shows a posterior view of the spine showing the basivertebral nerve emanating from a bifurcated branch of the sinuvertebral nerve.
Figure 5:
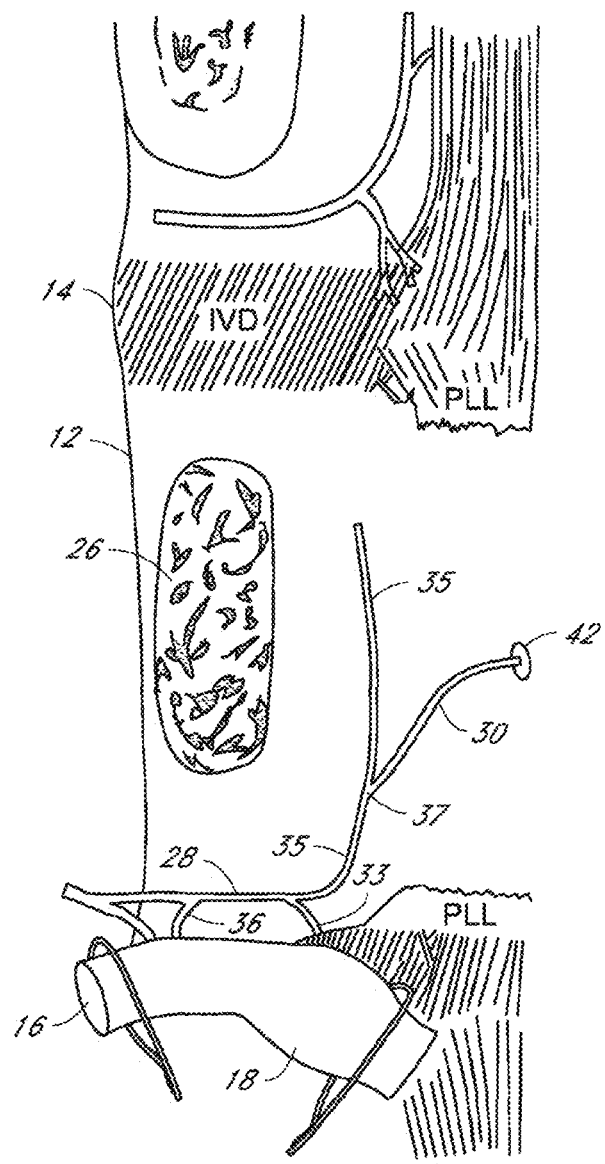
FIG. 5 shows a posterior view of another spine sample showing the basivertebral nerve emanating from a bifurcated branch of the sinuvertebral nerve.

FIGS. 4 and 5 are similar posterior views of the spine 10 showing the basivertebral nerve 30 emanating from a bifurcated junction 37 of the sinuvertebral nerve 28. In each of these cases, the lesser descending branch 33 is formed from a first junction with the ascending branch 35 of the sinuvertebral nerve 28. The basivertebral nerve 30 then emanates from the ascending branch 35 at the bifurcated junction 37, and runs medially under the posterior longitudinal ligament 32 and into the basivertebral foramen 42. FIG. 5 shows an example where the bifurcated junction (e.g., basivertebral nerve junction) 37 is closer to the origination of the sinuvertebral nerve 28 with somatic root 36 and anatomic root 38.

The basivertebral nerve 30 comprises the largest medial branch emanating from the sinuvertebral nerve 28, which runs medially under the posterior longitudinal ligament 32. The basivertebral nerve 30 travels into the basivertebral foramen 42 to innervate the vertebral body.

Figure 6:
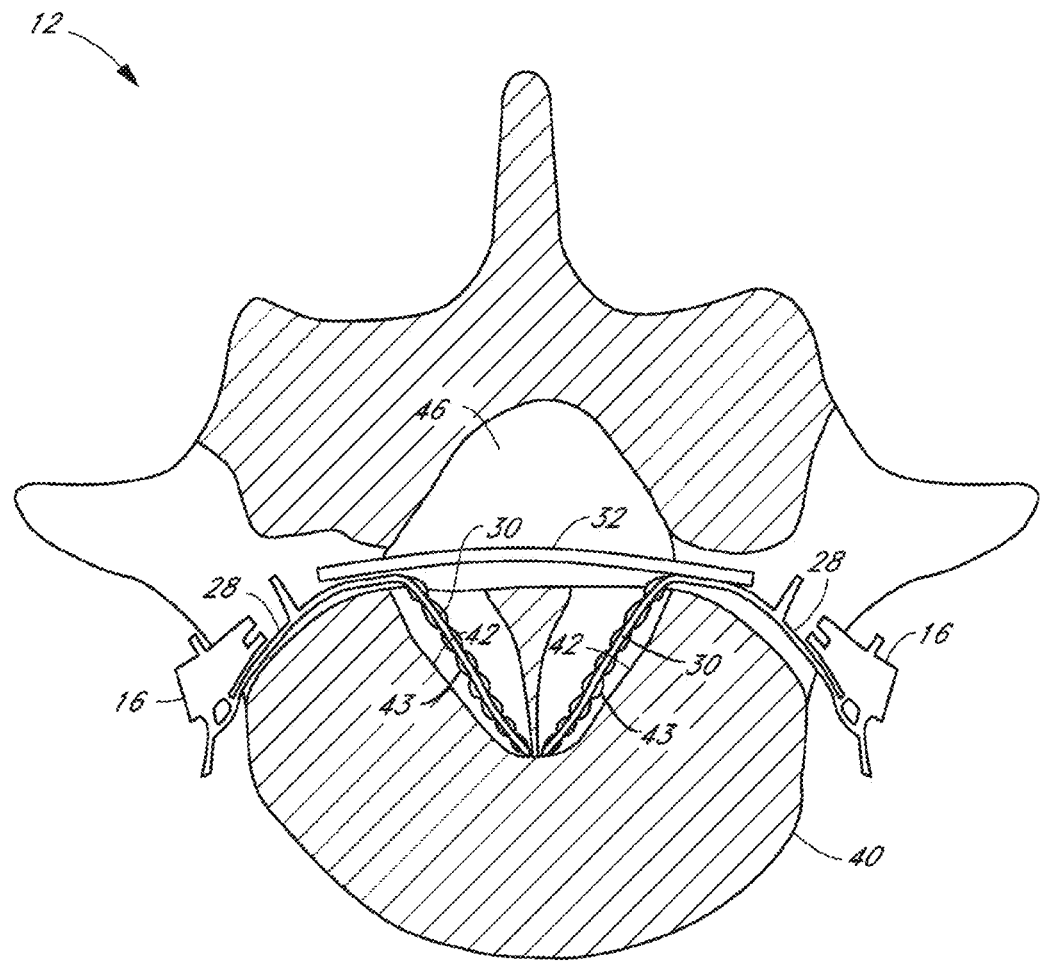
FIG. 6 illustrates a cross-sectional view of a vertebral body shown in FIG. 1.

FIG. 6 illustrates a cross-sectional view of the vertebral body 12 shown in FIG. 1, with associated anatomy. As shown in FIG. 6, the left and right basivertebral nerves 30 emanate from the sinuvertebral nerve 28 and travel medially under the posterior longitudinal ligament 32 and into the vertebral foramina 46. Each corresponding basivertebral nerve 30 then enters corresponding left and right basivertebral foramen 42, where they generally bundle with basivertebral blood vessels 43 and travel to the end of the conical-shaped basivertebral foramen 42 to then enter the bony mass of the vertebral body 40. In some cases, there may be only one basivertebral foramen (shown in FIG. 13), and both left and right basivertebral nerves may travel toward the distal end of the same basivertebral foramen.

Figure 7:
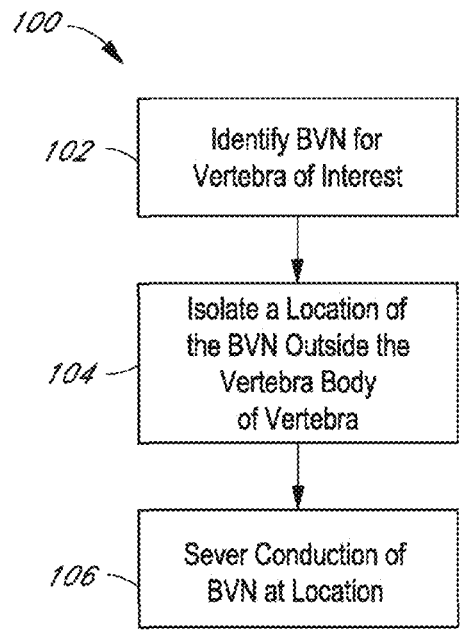
FIG. 7 illustrates a schematic diagram of an embodiment of a method for treatment of pain via denervation of the basivertebral nerve at a location external to the vertebral body.

FIG. 7 illustrates a schematic diagram of an embodiment of a method 100 for treatment of pain via modulation of the basivertebral nerve 30 within a patient. In accordance with several embodiments, access to the basivertebral nerve 30 for subsequent intraosseous nerve modulation (e.g., ablation, denervation, stimulation) may be achieved in at least two ways. In a first "minimally invasive" approach, the patient's skin may be penetrated with a surgical instrument, which is then used to access the desired basivertebral nerves, e.g., percutaneously.

In a second "open" approach, the intraosseous nerves (e.g., basivertebral nerves) may be modulated during an open surgery or surgical repair of the spine 10, wherein the patient's spine, or a portion thereof, is fully exposed for the primary surgery (e.g., vertebral fracture repair, spinal fixation, tumor removal, etc.). The basivertebral nerves 30 may be permanently or temporarily denervated (e.g., ablated, cut, crimped) as a prophylactic measure against subsequent post-surgical back pain. In some embodiments, intraosseous nerve modulation (e.g., ablation, denervation, stimulation) may also occur prior to the primary spinal surgery.

Regardless of whether the basivertebral nerve modulation is performed percutaneously or as a secondary procedure during a conventional spinal surgical repair, the following discussion is directed to various embodiments of surgical methods for accessing basivertebral nerves. While the following description is limited to three different approaches for accessing the basivertebral nerves, alternative approaches may be taken by the surgeon depending upon the clinical setting without varying from the spirit and/or scope of the disclosure.

Figure 10:
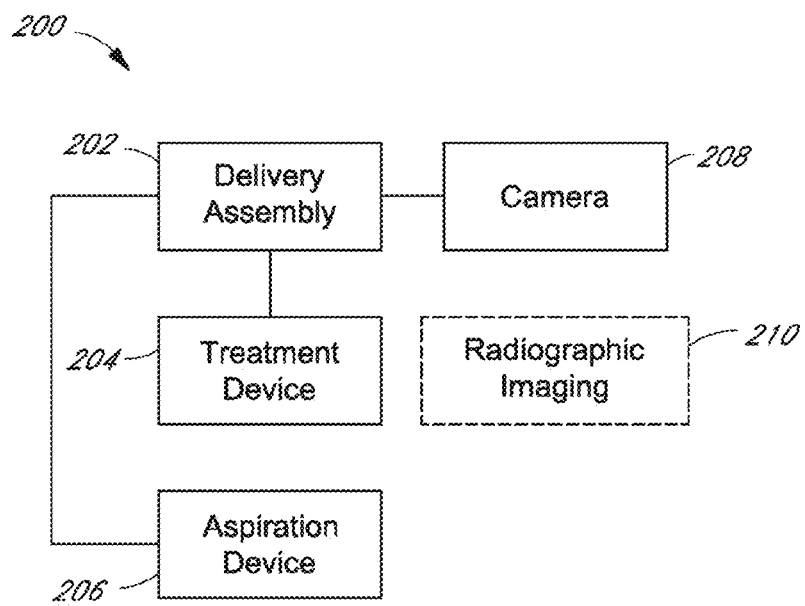
FIG. 10 shows an embodiment of a delivery and treatment system for minimally-invasively treating the basivertebral nerve at a location external to the vertebral body.
Figure 11:
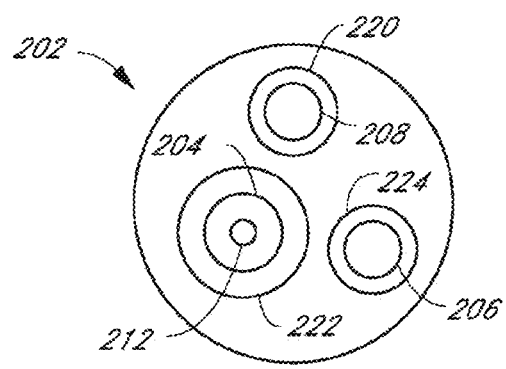
FIG. 11 shows a distal-end view of an embodiment of a delivery assembly.

Referring back to FIG. 7, in accordance with several embodiments, the first step 102 in method 100 is to identify at least a portion of the left or right basivertebral nerve 30 for the particular vertebral body of interest (e.g., the L3, L4, L5, S1, or S2 vertebra). Next, at step 104, a portion of the basivertebral nerve 30 is isolated at a location outside the vertebral body. In some implementations, the isolation is achieved by locating the origin of the basivertebral nerve 30 with the sinuvertebral nerve 28 at junctions 31 or 37 (see FIGS. 3-5). In some implementations, the isolation is achieved by locating the entry of the basivertebral nerve 30 into the vertebral body 40 (e.g. at basivertebral foramen 42 shown in FIG. 7). Identification and/or isolation at steps 102 and 104 may be performed via direct visualization with a catheter-based delivery system 200, as shown in FIGS. 10 and 11, or with an external imaging system (e.g., ultrasound, optical coherence tomography, MR imaging, CT imaging, Doppler, X-ray).

Figures 8, 9:
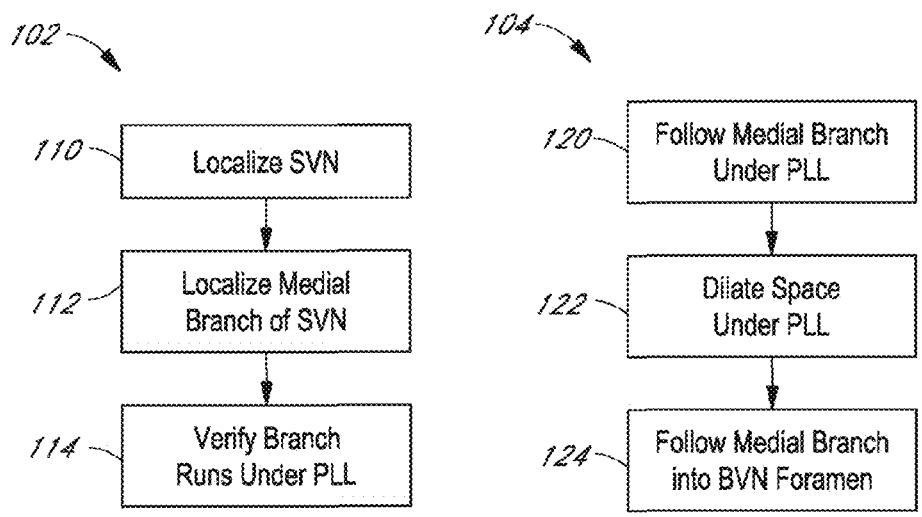
FIG. 8 illustrates a schematic diagram of an embodiment of a method for identifying the basivertebral nerve.
FIG. 9 illustrates a schematic diagram of an embodiment of a method for isolating the basivertebral nerve.

Referring to FIG. 8, in accordance with several embodiments, step 104 (isolating the basivertebral nerve 30 at junctions 31 or 37) is first performed by locating the sinuvertebral nerve 28 at step 110. In some embodiments, locating the sinuvertebral nerve 28 is performed percutaneously through intervening facie and tissues. Next, at step 112, the sinuvertebral nerve 28 is followed away from its origination ascending upward until the largest medial branch 30 is located at trifurcated junction 31 (trifurcated branch shown in FIG. 3) or bifurcated junction 37 (bifurcated branch shown in FIG. 4 or 5). The determination may then be verified at step 114 by verifying that the branch of the basivertebral nerve 30 runs under the posterior longitudinal ligament 32.

Referring to FIG. 9, in accordance with several embodiments, locating the entry of the basivertebral nerve 30 into the vertebral body 40 via step 104 may be performed by first following the medial branch 30 under the posterior longitudinal ligament 32 at step 120. In some embodiments, the space under the posterior longitudinal ligament 32 may then be dilated at step 122 to visualize the space underneath the posterior longitudinal ligament 32. The medial branch 30 may then be followed into the basivertebral foramen 42 at step 124. In some embodiments, to locate the entry of the basivertebral nerve 30 into the vertebral body 40, an alternative approach may be to dilate the posterior longitudinal ligament 32 and identify and/or visualize the basivertebral foramen 42 without identifying or following the medial branch of the sinuvertebral nerve 28. By locating basivertebral foramen 42, the basivertebral nerve 30 is also located, as the basivertebral nerve enters the vertebral body 40 via the basivertebral foramen 42.

Referring back to FIG. 7, in accordance with several embodiments, once the basivertebral nerve 30 is located and isolated for treatment, the desired treatment location of the basivertebral nerve 30 is denervated at step 106. For purposes of this disclosure, the terms "modulate" or "neuromodulate" as used herein, shall be given their ordinary meaning, and shall include modifying the conductive properties of the nerve, such that the transmission of signals from the nerve endings within the vertebral body are stimulated, altered, blocked, or eliminated altogether, to provide a therapeutic effect within or related to the vertebral body. Modulation shall also include ablation, denervation, disruption, inhibition, therapeutic stimulation, diagnostic stimulation, necrosis, desensitization, or other effect on tissue. Neuromodulation shall refer to modulation of a nerve (structurally and/or functionally) and/or neurotransmission. Modulation is not limited to nerves and may include effects on other tissue. Modulation may comprise a partial or total and/or partial or temporary loss or alteration of conduction of the nerve across the location for treatment of the nerve. In several embodiments, modulating (e.g., denervating) the nerve may be achieved by cutting, crimping, heating, cooling, radiating, agitating, or altering the chemical composition of the nerve at the treatment location.

The goal of the treatment or modulation (e.g., denervation) may be ablation or necrosis of the target nerve or tissue, or some lesser degree of treatment to denervate the basivertebral nerve. For example, the treatment energy, frequency and/or other treatment parameters may be just sufficient to stimulate the nerve to block the nerve from transmitting signals (e.g., signals indicative of pain).

In one embodiment, the treatment system 200 (shown in FIGS. 10 and 11 and described in further detail below) may comprise a number of different treatment modalities for therapeutic treatment of the target region. For example, in one embodiment, the treatment devices or probes in system 200 operate in a manner that produces heat or thermal energy (such as described in U.S. Pat. No. 6,699,242, herein incorporated by reference in its entirety) that modulates (e.g., ablates) the tissue of the target region (e.g., a basivertebral nerve) at the target region (e.g., a basivertebral nerve location). In some embodiments, the treatment devices or probes in system 200 operate in a manner that produces acoustic energy. The treatment devices or probes may include one or more energy sources (e.g., RF energy sources, ultrasonic transducers or elements, microwave energy sources, light energy sources, plasma ion sources). In some embodiments, energy sources of different energy modalities may be used in combination. For example, one energy source may emit ultrasound energy while another energy source may emit microwave or electrical energy. The energy output may be dynamically controlled by changing the power intensity, the frequency, the angle of dispersion, the focus, or other dynamically controllable parameters. In some embodiments, the treatment devices or probes in system 200 comprise surgical cutting devices or fluid delivery devices. In one embodiment, the treatment device s or probes comprise a bipolar RF probe with a pair of electrodes. In some embodiments, the fluid delivery device comprises a catheter, tube, sleeve, needle, cannula, wicking device, or other conduit configured to deliver fluid. The fluid may comprise neurolytic agents, chemotherapy agents, radioactive substances, medications, drugs, pharmaceuticals, alcohols, acids, solvents, cooling agents, nerve blocking agents, and/or other chemical agents.

In one embodiment, the treatment device is configured to deliver therapeutic treatment that is targeted to block nerve conduction without ablating the nerve (e.g., treatment is delivered to the nerve via thermal therapy, chemical agent, or the like) that results in denervation of the basivertebral nerve without necrosis of tissue. This may be achieved via delivery of a lesser amount of energy or agent to the tissue site (either in the form of less exposure time, concentration, intensity, etc.) than is required for ablation, but an amount sufficient to achieve some amount of temporary or permanent denervation. In some embodiments, the treatment device is configured to stimulate nerves.

In one embodiment, dosing of the treatment therapy may be tailored to the desired goal for modulation, the region or type of tissue to be treated, and the modality being used, among other factors.

In one embodiment, when heating is the applied modality, a minimum dose threshold of 30 CEMs (Cumulative Equivalent Minutes), with temperatures between 40° C. and 100° C. (e.g., between about 40° C. and about 60° C., between about 40° C. and about 80° C., between about 50° C. and about 90° C., between about 60° and about 100° C., between about 50° C. and about 80° C., or overlapping ranges thereof) is applied for some tissues. In some embodiments, cooling is administered to the target tissue (using either the treatment device or a separate device.

In some embodiments, a thermal dose of 300 CEMs may be used to ablate tissues, and sometimes the dose may reach 1000 CEMs or more. The delivered dose may be a function of several different variables: e.g., tissue type, thermal conduction of the surrounding tissues, treatment region, treatment type, and other uncontrolled variables. In various embodiments, the thermal dose may be between about 30 and about 1000 CEMs, between about 100 and about 500 CEMs, between about 50 and about 300 CEMs, between about 200 and about 400 CEMs, between about 300 and about 800 CEMs, between about 400 and about 900 CEMs, between about 500 and about 1500 CEMs, or overlapping ranges thereof.

In some embodiments, such as when RF energy is used, the impedance of the target tissue may also have an effect and be factored in the desired dosing treatment plan. If ultrasound energy is used, the propagation of the energy through the tissues is a major factor, (e.g., ultrasound generally propagates better through soft tissues than hard tissues, such as bone). Propagation of the energy (e.g., via ultrasound or RF) may be also be enhanced or modified by other substances added to the local tissues. The ultrasound energy may be used for cavitation or non-cavitation.

In one embodiment, the material used to enhance the conduction of the energy may be a biological material such as blood. In some embodiments, the biological material may serve to enhance the energy delivery while simultaneously acting as an insulator for another area of the body. For example, delivery of blood may enhance the propagation of thermal energy at some temperatures, but may act as in insulator if exposed to higher temperatures, thus effectively blocking the transmission of potently damaging thermal energy to other neighboring nerves or anatomy once a threshold temperature is exceeded.). In embodiments where RF energy is used for heating the nerve or other target tissue, the frequency may be any integer between about 100 kHz and 1 MHz, between 400 kHz and 600 kHz, between 300 kHz and 500 kHz, between 350 kHz and 600 kHz, between 450 kHz and 600 kHz, between 300 kHz and 450 kHz, between 350 kHz and 500 kHz, between 400 kHz and 600 kHz, between 450 kHz and 550 kHz, between 460 kHz and 500 kHz overlapping ranges thereof, or any frequency within the recited ranges.

For stimulation of the nerve using RF energy, in accordance with several embodiments, the frequency may be applied at a substantially lower level, e.g., in the range of approximately 1 Hz to 200 kHz, and may be used in a pulsed or continuous mode. In one embodiment, the total CEMs in the stimulation mode are maintained below 30 to limit tissue damage. Pulsed energy may be used to stimulate the nerve in one mode and then the frequency, pulse width or intensity may be modulated (e.g., increased) to achieve ablative/destructive doses of energy. In one embodiment, stimulation of the nerve is performed to block the travel of signals indicative of pain. Stimulation may comprise mechanical, electrical, or electromechanical stimulation.

Each vertebra generally comprises a left and right basivertebral nerve 30 that leads into the vertebral body 40. Accordingly, once a first side (e.g. left side) is treated, the procedure may then be repeated for the corresponding opposite side (e.g. right side). In some embodiments, a "side" is defined by a center line extending from the center of the posterior outer cortical wall to the center of the anterior cortical wall. In other embodiments, "side" can be defined by any line extending through the center of the vertebral body.

Patient feedback may be acquired at particular stages within the procedure. For example, in one embodiment, the target region of the basivertebral nerve 30 may be heated at a lower, non-destructive or "stimulating" level to generate a desired temporary therapeutic response from the patient. Patient feedback may then be obtained to verify that the location is correct before a destructive or permanent dose is delivered.

FIG. 10 shows one embodiment of a delivery and treatment system 200 for minimally-invasively treating the basivertebral nerve 30 at a location external to the vertebral body. System 200 comprises a delivery assembly 202, such as the multi-lumen catheter 202, that is configured to be introduced into the body subcutaneously and delivered to the basivertebral nerve 30 at one its junctions 31, 37 with sinuvertebral nerve 28, and/or to the basivertebral foramen 42 under the posterior longitudinal ligament 32.

In some embodiments, the treatment system 200 comprises a treatment device 204 for achieving the desired denervation at the treatment location at the basivertebral nerve 30. The treatment device 204 may be configured to deliver any number of treatment modalities (singly or in combination) at the treatment site for therapeutic denervation of the basivertebral nerve 30 or other nerves within bone. For example, treatment may be affected by monopolar, bipolar or tripolar RF, ultrasound, acoustic, radiation, steam, microwave, laser, light, or other heating means. Additionally, in some embodiments, the treatment device 204 may comprise a fluid delivery catheter that deposits an agent (e.g., bone cement, chemoablative fluid, radioactive substance, or other therapeutic agent) to the treatment location at the basivertebral nerve 30. In one embodiment, cryogenic cooling may be delivered for localized treatment of the basivertebral nerve 30. In one embodiment, treatment may be affected by any mechanical destruction and or removal means capable of severing or denervating the basivertebral nerve 30. For example, a cutting blade, bur or mechanically actuated cutter may be used to affect denervation of the basivertebral nerve 30.

In accordance with several embodiments, and in addition to or separate from treating the basivertebral nerve, a sensor (not shown) may be delivered to the region to preoperatively or postoperatively measure nerve conduction or heating at the treatment region. In this configuration, the sensor may be delivered on a distal tip of a flexible probe that may or may not have treatment elements (e.g., electrodes, ultrasound transducers, microwave elements) as well.

In one embodiment, system 200 comprises a camera 208 or other imaging device sized to be received within delivery assembly 202. The camera 208 can be configured to provide visualization of the nerves and surrounding anatomy for navigating to the proper location and identification of the basivertebral nerve 30 and surrounding anatomy. The imaging device can comprise one or more optical fibers for lighting and/or one or more optical fibers for imaging.

In one embodiment, system 200 further comprises an aspiration device 206 sized to be received within delivery assembly 202 for delivering fluid to the region (e.g., under the posterior longitudinal ligament 32 to dilate a space under the posterior longitudinal ligament 32 for visualization of the basivertebral nerve 30, basivertebral foramen 42, or other anatomy). Aspiration of the surrounding anatomy may be used for navigating to the proper location and identification of the basivertebral nerve 30 and surrounding anatomy (e.g. sinuvertebral nerve, 28 and/or basivertebral foramen 42).

In one embodiment, system 200 may comprise a secondary visualization and/or imaging means 210, such as radiographic (x-ray) imaging, to be used in combination with, or in alternative to, direct imaging. For example, the basivertebral foramen 42 may be located via radiographic imaging for direct treatment of the basivertebral nerve 30 within the basivertebral foramen.

FIG. 11 shows a distal-end view of one embodiment of a delivery assembly 202. Delivery assembly 202 may comprise a multi-lumen catheter with a plurality of lumens 220, 222, and 224 for minimally-invasively delivering diagnostic and treatment instruments to the treatment location.

In one embodiment, catheter 202 comprises a first lumen 220 for delivery of a camera 208 or other imaging device. In some embodiments, catheter 202 comprises a second delivery lumen 222 for delivery of a treatment device 204, which may comprise a treatment element 212. Treatment element 212 may comprise an energy/therapy delivery applicator (e.g., RF element, agent delivery lumen, cutting blade, or the like) for treatment of the basivertebral nerve 30 at the treatment location. In one embodiment, catheter 202 comprises a third lumen 224 for delivery of an aspiration device 206 simultaneously with either the imaging device 208 or treatment device 204.

Figure 12:
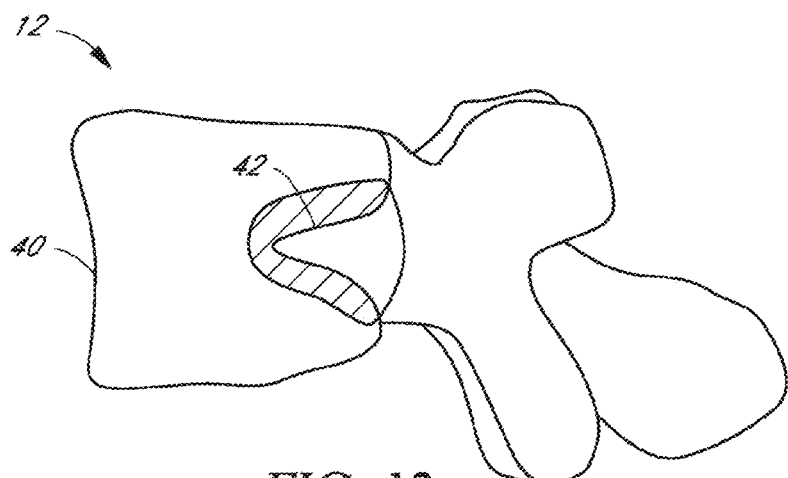
FIG. 12 illustrates cut-out side view of a lumber vertebra.
Figure 13:
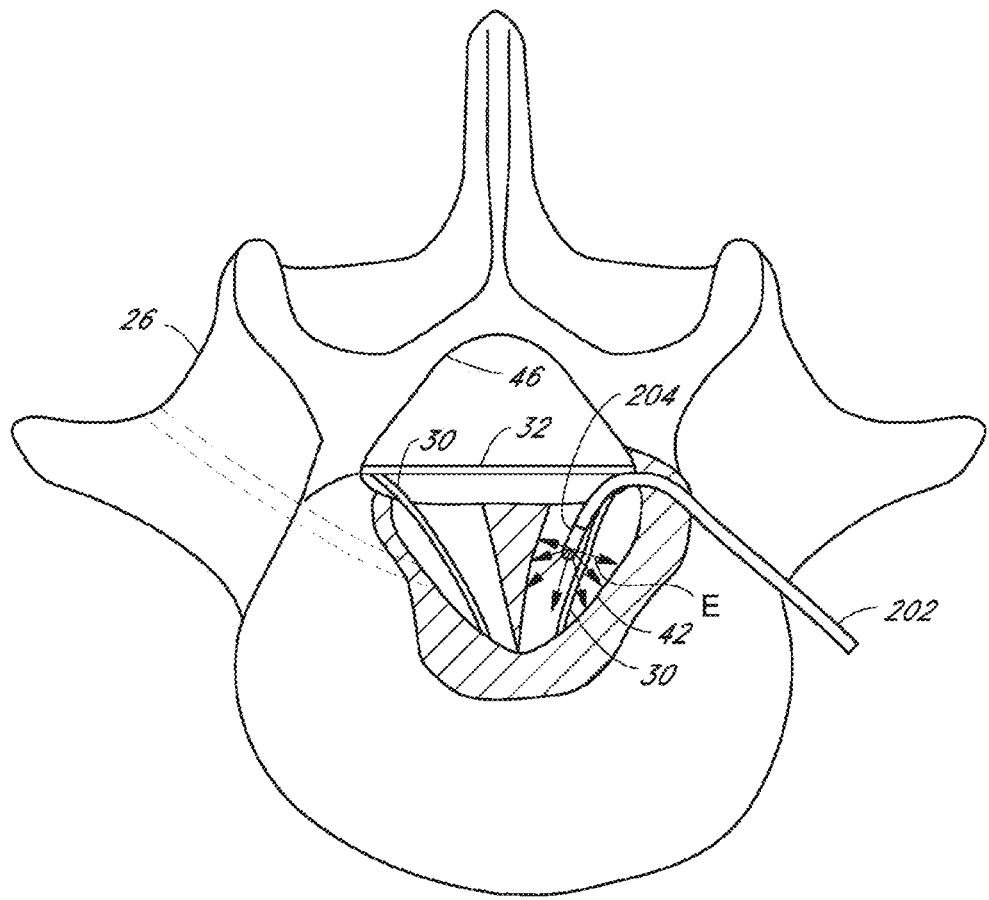
FIG. 13 illustrates a cut-out top view of a vertebral body showing placement of an embodiment of a treatment delivery assembly within a first of two basivertebral foramen.
Figure 14:
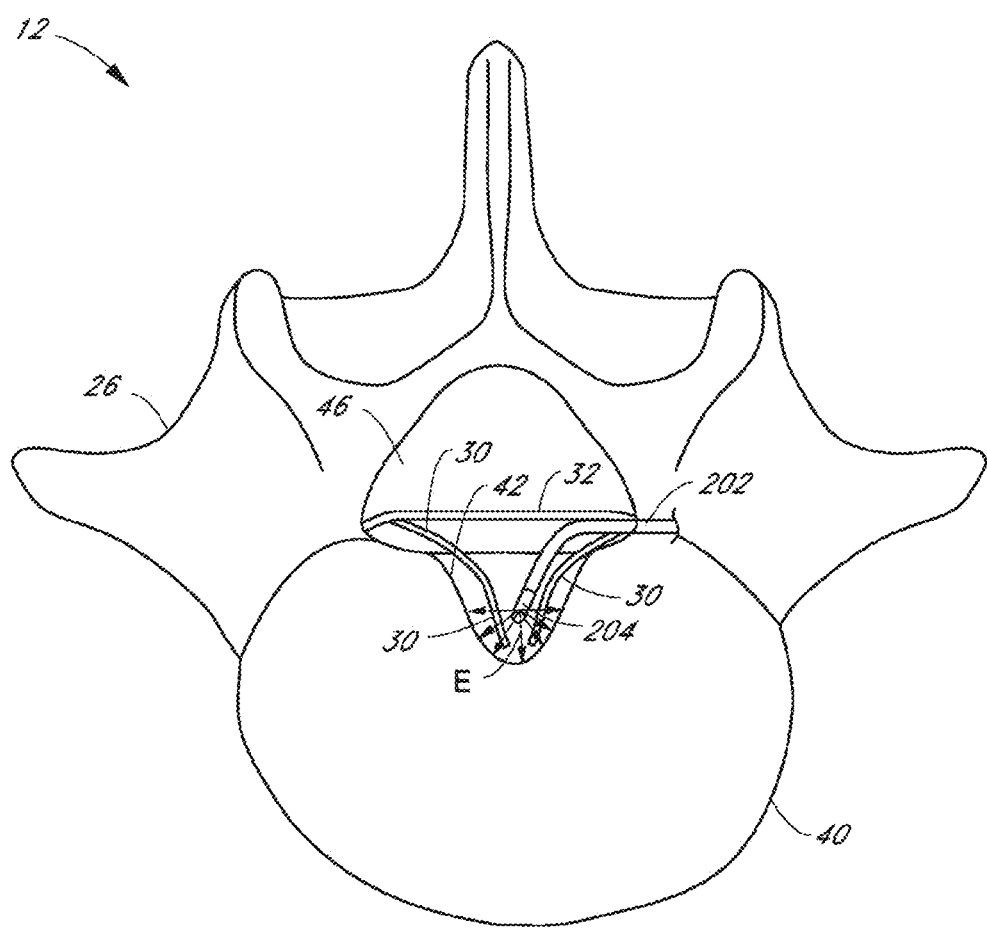
FIG. 14 illustrates a cut-out top view of a vertebral body showing placement of an embodiment of a treatment delivery assembly within a vertebra having one basivertebral foramen.

As explained above, the treatment location may comprise the location of the basivertebral nerve 30 at the entry point within the vertebral body 40 within the basivertebral foramen 42. FIGS. 12-14 show the basivertebral foramen 42 and one embodiment of the treatment assembly 202 delivered at the treatment location within the basivertebral foramen 42.

FIG. 12 illustrates a cut-out side view of a lumber vertebra 12. As shown m the cutout m vertebral body 40, the basivertebral foramen 42 is a conical opening emanating from the spinal canal 46 and generally positioned along the midline of the vertebral body 40. Previous systematic histological analysis of the vertebral body 40 has established the predominant entry point for vertebral intraosseous nerves as the basivertebral foramen 42, and the major source of innervation of the vertebral body 40 as the basivertebral nerve 30. The large basivertebral foramina 42 universally penetrate the posterior cortex of the vertebral body 40 at a midline of the vertebral body. The basivertebral nerves (which arise as a branch of the sinuvertebral nerve, which in turn anastomoses with the sympathetic chain) enter the vertebral body 40 through these foramina 42, arborize and innervate the vertebral body 40 down to and including the endplates. Nociceptive function of these basivertebral nerves has been confirmed by staining.

FIG. 13 illustrates a cutout top view of a vertebral body showing placement of one embodiment of a treatment delivery assembly 202 within a first of two basivertebral foramen 42. In one embodiment, the treatment device 204 is delivered into the basivertebral foramen 42 and then actuated to modulate (e.g., denervate) the basivertebral nerve 30 (this location may comprise multiple branches of the basivertebral nerve 30) within the cavity of the basivertebral foramen 42. FIG. 13 is shown with one embodiment of an energy delivery device (e.g. ultrasound or RF applicator) delivering a field of energy E into the basivertebral foramen 42 to denervate the basivertebral nerve 30. Other modalities (e.g., cutting blade, agent delivery, etc.) may also be delivered into the cavity 42 with appropriate non-energy delivery devices. In one embodiment, energy is delivered radially outward and/or forward into the cavity 42 so as to form a conduction block of the basivertebral nerve 30 toward at least one location within the basivertebral foramen 42. The field of energy may be delivered omnidirectionally or in a controlled direction. Device 204 may comprise shielding or directed energy delivery so as not to direct energy backward into the spinal canal 46, and only direct energy into the basivertebral foramen 42, where the energy is contained within the bony walls of the basivertebral foramen 42.

In one embodiment, once the first basivertebral nerve 30 is treated within the first basivertebral foramen 42, the treatment device 204 may then be disposed in the other basivertebral foramen 42 to treat the basivertebral nerve 30 on the other side. This may be achieved by advancing treatment assembly 202 further within the canal 46, or by accessing the other basivertebral foramen 42 from the opposite side of the vertebra 12.

In one embodiment, the basivertebral foramen 42 is accessed through a transpedicular approach, where a channel (shown as dashed lines in FIG. 13) is bored into pedicle 26. The channel may generally comprise a curved channel based on the location and size of the basivertebral foramen 42, and bored with instruments and methods as detailed in U.S. Patent Pub. No. 2010/0324506, filed on Aug. 26, 2010, and U.S. patent application Ser. No. 13/612,541, filed on Sep. 12, 2012, each of which is incorporated by reference herein in its entirety.

As seen in FIG. 14, the vertebra 12 may only comprise one basivertebral foramen 42. In this case, the treatment delivery assembly 202 and treatment device 204 are delivered into the singular basivertebral foramen 42, and may deliver energy field E to treat both left and right basivertebral nerves 30 simultaneously.

Cadaver Study of the Proximal Basivertebral Neuroanatomy

The following study was performed on the neuroanatomy of the proximal basivertebral system, with the specific objective of identifying neural components entering the basivertebral foramina, and tracing the primary basivertebral nerve to a point of origin. A series of three cadaver studies were conducted to identify the origination of the basivertebral nerve and path into the vertebral body. The three cadaver studies are non-limiting examples of embodiments of identification of basivertebral nerve origin.

Cadaver Dissection I (Cadaver A)

With the cadaver in the prone position, a midline incision was made over the lumbar spine from L2 to S1 and extended laterally 10 cm at each end into an 'H'. The paraspinal muscles and other soft tissues were elevated and dissected clear of the posterior spine with sharp dissection, and the lamina exposed. The dorsal spine and lamina were totally excised utilizing an oscillating saw, exposing the spinal canal and cord (within the dura) and the dorsal ganglia.

The cord was gently retracted with dural retractors, ligatures placed for traction, and the Posterior Lateral Ligament isolated and gently elevated clear of the posterior spinal canal with blunt dissection technique.

The adherent elements of soft tissue were gently cleared by blunt dissection using alternating saline saturated and dry gauze sponges, exposing elements of the neural network and the basivertebral foramina. Further local dissection at each foramen was conducted to provide visibility for specific appreciation of the various elements entering the foramina.

Figure 15:
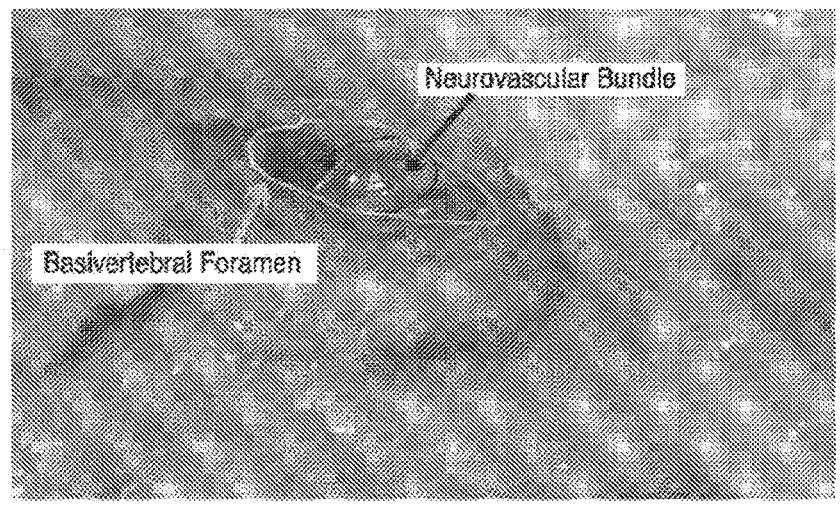
FIG. 15 is a picture of a cadaver showing numerous small neural elements converged on the foraminal ostia.
Figure 16:
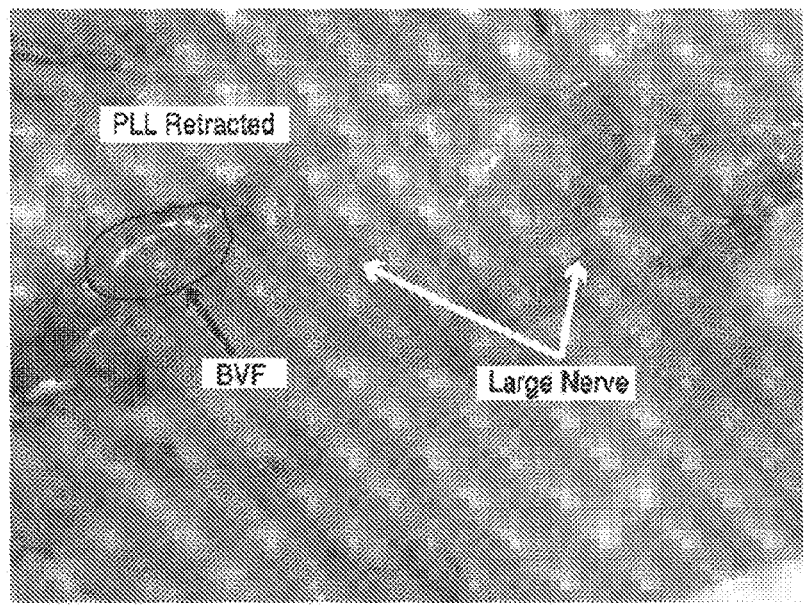
FIG. 16 is a picture of a cadaver showing larger, more singular nerves observed entering from the general region of the nerve root.

Referring to FIG. 15, it was observed that numerous small neural elements converged on the foraminal ostia, which then generally followed the vascular elements into the vertebral body, forming a classic neurovascular bundle. As seen in FIG. 16, larger, more singular nerves were observed entering from the general region of the nerve root. Due to the mechanical disruption of soft tissue in this area from the laminectomy, the exposure utilized rendered tracing these nerves entering the canal to their point of origin (from inside the canal tracing outwards) unfeasible in this cadaver. It was determined that a subsequent dissection utilizing an alternate approach would be conducted focusing on the post-ganglionic anatomy, tracing any nerves entering the canal from that region (from outside the canal tracing inwards).

Cadaver Dissection II (Cadaver B)

With the cadaver in the prone position, a midline incision was created overlying the Lumbar spine approximately 20 cm in length. Sharp dissection was used to expose the posterior aspect of the lumbar spinous processes. With these landmarks well exposed, the incision was extended laterally approximately 5 cm in each direction at both ends of the original incision to create a very wide exposure (in the shape of an "H"). Following this, the lamina and facet joints of L1, L2, L3, and L4, were widely exposed. Rongeurs and osteotomes were then used to remove the facet joints, lamina, and ligamentum flavum creating a wide exposure of the dura, the Dorsal Root Ganglion, and exiting nerve roots. Pedicles were divided on the coronal plane.

Beginning on the left side, the nerve roots were divided as they exited the central dural sac. The central dura thus drained of CSF, collapsed and was gently retracted medially out of the field. The root itself was then gently retracted laterally. With careful elevation of the nerve root, the sinuvertebral nerve was easily identified at each of the levels dissected, as it branched off of the large nerve root and coursed back through the foramen (between the remaining stumps of the pedicles).

Results

Figure 17:
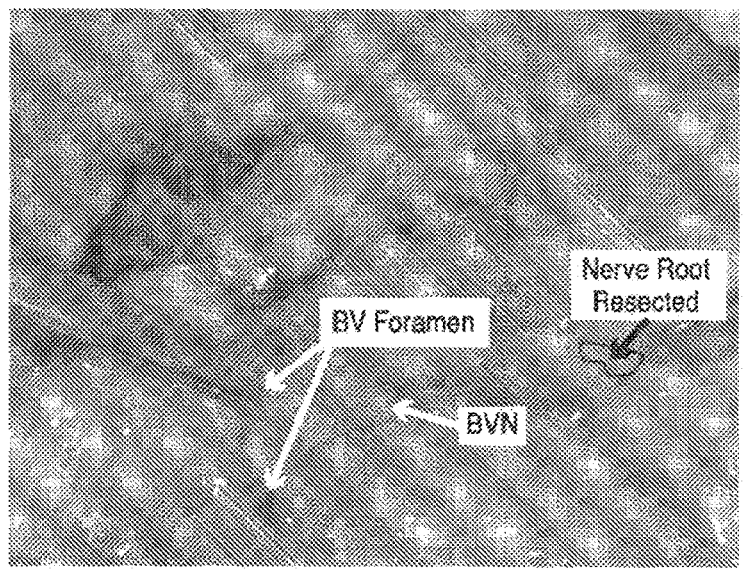
FIG. 17 is a picture of a cadaver showing largest medial branch of the sinuvertebral nerve.
Figure 18:
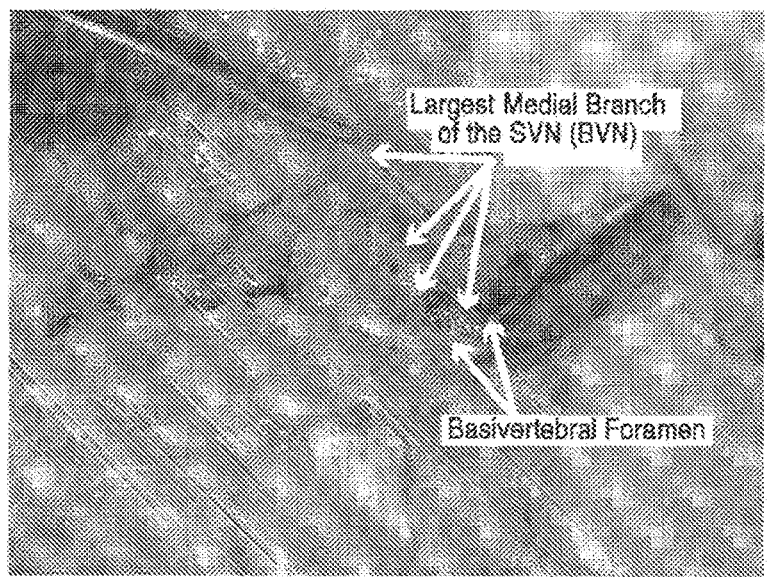
FIG. 18 is another picture of a cadaver of FIG. 17.

The sinuvertebral nerve divided variably into 3 or more branches, as expected. In every case, however, a branch of the sinuvertebral nerve was seen to course medially beneath the posterior longitudinal ligament. The posterior longitudinal ligament in this cadaver was very white and somewhat flaccid, and the space beneath it could be well visualized by only partially dividing it. Referring to FIG. 17, the largest medial branch of the sinuvertebral nerve was seen in every case to course directly into the basivertebral foramen, where it then divided usually into 3 to 5 smaller branches and entered the bone (see FIG. 18). The dissection clearly documented that the basivertebral nerve is a branch of the sinuvertebral nerve.

Having successfully established the basivertebral nerve's origin as a branch of the sinuvertebral nerve and having mapped the basivertebral nerve's usual course, additional detailed dissections were undertaken to further document and illuminate these findings and to gain some understanding of the nature and prevalence of individual variants.

Cadaver Dissection III

Cadavers were positioned prone on a dissecting table. A longitudinal midline incision was made from L1 to the mid sacral level. The skin, subcutaneous fat was divided to expose the lumbar fascia. The fascial incision was carried out, also longitudinally, and the paraspinal muscles were dissected off of the spinous processes and the lamina bilaterally. The skin incision was then extended laterally from the proximal and distal end, approximately 8 cm on both sides to create the shape of an H.

These large flaps were then developed on both sides to allow good exposure of the spinous processes, lamina, facet joints and interlaminal spaces from L5 to L1.

Spinous processes were removed with rib cutters, and the lumbar lamina then removed with rongeurs and Cloward type punches. Blunt dissection allowed exposure of the dural sac. The facet joints were then completely removed bilaterally using osteotomes and rongeurs to expose the pedicle, which was viewable "end on" transected in the coronal plane. Exiting nerve roots were identified, and exposed from the axilla, to at least one cm beyond the lateral border of the pedicle, and beyond the thickened portion of the dorsal root ganglion. Following the gross exposure, superior visualization surgical loupes (3.5×) were used for visualization of the finer neurovascular structures during the remainder of the dissection.

Exposure of the sinuvertebral nerve was accomplished by transecting the nerve root at its base as it branched off of the dural sac. The root was then carefully and gently reflected laterally and the volar aspect inspected. In all cases, the sinuvertebral nerve was seen to exit the volar aspect of the sheath, at or immediately lateral to the distal portion of the ganglion. In many cases, other small nerves were also seen to emerge immediately distal to the dorsal root ganglion, sometimes (but not always) anastamosing with the sinuvertebral nerve. Most of the other small nerves coursed dorsally or posteriorly. Generally, only one nerve (the sinuvertebral nerve) coursed retrograde back through the foramen.

The details of the anatomy at each exposed level are described below:

Cadaver C

L5 left: The sinuvertebral nerve entered the epidural space before the first small branch was noted, which coursed directly caudad. The larger branch coursed cephalad to the level of the inferior border of the L5 pedicle, when a large branch travelled medially, directly to the basivertebral foramen L5 Right: Two branches were seen to arise from the root, just past the thickening of the ganglion. The smaller branch coursed inferomedially before branching into two equally sized nerves just before travelling beneath the posterior longitudinal ligament. It was not possible to follow them further. The "other sinuvertebral nerve" coursed cephalomedially until dividing into two approximately equally sized branches, just medial to the posterior longitudinal ligament. One branch coursed directly medially onto the basivertebral foramen, the other coursed cephalad.

L4 left: This sinuvertebral nerve coursed cephalomedially until it neared the edge of the posterior longitudinal ligament, where it divided into two branches. The inferior branch coursed caudad, parallel to the border of the posterior longitudinal ligament. The other coursed cephalad, immediately lateral to the border of the posterior longitudinal ligament before branching at the level of the inferior pedicle, creating a branch that coursed medially, beneath the posterior longitudinal ligament, to enter the basivertebral foramen.

L4 Right: This sinuvertebral nerve coursed directly medial, sending small branches cephalad and caudad shortly after entering the epidural space. The larger central branch continued medial until immediately after passing beneath the posterior longitudinal ligament, it divided into 2 nearly equal branches. One of these coursed inferiorly and medially, the other coursed cephalomedially directly to the basivertebral foramen.

L3 Left: The sinuvertebral nerve coursed cephalomedially to about the level of the middle of the L3 pedicle, where it trifurcated, sending one branch caudad, one branch cephalolaterally, and one branch medially. The medial branch coursed directly toward the basivertebral foramen, and divided into three smaller nerves at the basivertebral foramen, all of which entered the basivertebral foramen.

L3 Right: This sinuvertebral nerve had a curved course, travelling cephalomedially, trifurcating at the level of the lateral border of the posterior longitudinal ligament. A very small branch coursed directly caudad. The remaining branches were equivalent in size. One travelled cephalad, the other coursed medially and slightly inferiorly to enter the basivertebral foramen.

Cadaver D

L5 left: The sinuvertebral nerve entered the epidural space coursing medially, and did not branch until approximately 3 mm medial to the medial border of the pedicle where it began coursing cephalad. The first branch coursed medially directly to the basivertebral foramen. A second medial branch was seen that also coursed directly to the basivertebral foramen. The sinuvertebral nerve continued to course cephalad, and was not explored as it travelled past the upper border of the pedicle.

L5 right: Two small nerves exited the root, just beyond the pedicle and coursed back into the spinal canal. The caudad nerve coursed inferiorly. The second coursed medially for approx 0.3 cm before curving cephalad at the level of the basivertebral foramen; this nerve branched once, both branches entered the basivertebral foramen.

L4 Left: sinuvertebral nerve coursed into the epidural space, the first branch coursed inferiorly. The larger branch coursed cephalad. At above the level of the middle of the pedicle it split into 4 branches. Two of them coursed directly to the basivertebral foramen, and the other two coursed cephalad.

L4 right: The sinuvertebral nerve coursed medially for approx 3 mm, and then split into 4 branches, one coursed cephalad, one caudad and two coursed to the basivertebral foramen and entered it.

L3 left: the sinuvertebral nerve coursed medially for about 2 mm, then split into 4 nerves. One coursed superiorly, one coursed to the basivertebral foramen and entered it, one coursed medially (inferior to the basivertebral foramen), and one coursed caudad.

L3 right: The sinuvertebral nerve coursed medially approx 4 mm, a branch then travelled caudad, and another travelled obliquely caudad and medial. This branch divided into two, one coursing to the basivertebral nerve and one continuing cephalad L2 left: The sinuvertebral nerve coursed medially and slightly cephalad before a branch was produced that travelled caudad. A second branch the was seen to course medially, inferior to the basivertebral foramen, the larger branch travelled very close to the basivertebral foramen and a short branch travelled medially to enter the basivertebral foramen, the continuation of this sinuvertebral nerve continued cephalad and branched again medially, above the level of the basivertebral foramen.

L2 right: the sinuvertebral nerve coursed cephalad and medial. The first branch coursed caudad. The second branch coursed cephalad and medial to enter the basivertebral foramen. The other branch continued cephalad.

Cadaver Dissection IV

Designs for Vision surgical loupes (6.0×) were used for visualization of the finer neurovascular structures during the remainder of the dissection.

Cadaver E

L5 left: a large sinuvertebral nerve branched more laterally than most, dividing into three branches; one coursed caudad, one cranially, and the "middle" one coursed directly to the basivertebral foramen where several small branches entered the foramen. Interestingly the larger branch continued cephalad, actually appearing to travel slightly Right of the midline.

L5 Right: This small sinuvertebral nerve coursed directly cephalomedially to enter the basivertebral foramen. No other branches were identified.

L4 left: The sinuvertebral nerve branched into three distinct nerves at the level of the foramen. One branch coursed caudad, one cephalad and the middle branch coursed directly to the basivertebral foramen.

L4 Right: This sinuvertebral nerve coursed very similarly to the sinuvertebral nerve on the Left. A large sinuvertebral nerve divided into 3 nearly equally sized branches at the level of the foramen. One branch curved cephalad, another curved Caudad, and the middle branch coursed directly to the basivertebral foramen.

L3 left: Only one small nerve was identified leaving the root and reentering the canal. This nerve coursed directly to enter the basivertebral foramen without other visible branches.

L3 Right: the sinuvertebral nerve was seen to enter the epidural space in a very medial direction. It divided into two branches at immediately beneath the lateral border of the dural sac. One barge branch coursed caudad. The other branch coursed cephalad, but broke before reaching the level of the inferior border of the pedicle. The broken end could not be reliably identified.

L2 left: the sinuvertebral nerve divided into two nearly equal branches immediately beneath the lateral border of the dural sac. One coursed caudad and medial, the other coursed directly toward the basivertebral foramen. This nerve trifurcated at the basivertebral foramen, sending one branch into the basivertebral foramen, while another branch continued cephalad. A smaller branch coursed inferomedially.

L2 Right: The sinuvertebral nerve abruptly separated into three branches within 2 mm of the dorsal root ganglion, at the level of the lateral border of the pedicle.

One branch coursed inferomedially, another cephalad, and the "middle' one coursed directly to the basivertebral foramen, and was seen to enter it.

Cadaver F

L5 Right: The sinuvertebral nerve coursed in an almost pure medial direction, before dividing at one point into two branches. One coursed caudad one coursed nearly vertically directly to the basivertebral foramen, which it entered. The remaining branch coursed cephalad.

L5 Left: The nerve entered the epidural space and coursed obliquely in the direction of the basivertebral foramen, approximately 2 mm from the midline it branched, sending one branch to enter the basivertebral foramen, and another to course cephalad. No branches were seen coursing caudad, but it is possible that such were severed during the dissection.

L4 Left: The sinuvertebral nerve coursed medially for approx 3 mm, the first small branch coursed caudad. The larger branch of the sinuvertebral nerve coursed cephalad, at about the level of the inferior border of the pedicle where it divided into two nearly equally sized branches; one branch was seen to travel obliquely cephalad and medial to enter the basivertebral foramen. The other branch of the sinuvertebral nerve continued cephalad.

L4 Right: The sinuvertebral nerve coursed medial and cephalad. No branch was identified coursing caudad. At approximately the level of the inferior border of the L4 pedicle, a large branch diverged from the sinuvertebral nerve and coursed obliquely medial and cephalad and directly entered the BV foramen. The other branch continued to course cephalad.

L3 Left: The sinuvertebral nerve divided into two large branches while still lateral to the foramen. These branches coursed cephalad and caudad, without sending identifiable branches to the basivertebral foramen L3 Right: The sinuvertebral nerve was not clearly identifiable at this level, very possibly due to disruption of the anatomy during pedicle removal. Therefore the nerve could not be traced antegrade. When dissection medially was undertaken to attempt a retrograde dissection, a "large" branch of a nerve was found to enter the basivertebral foramen from a cranial direction. Dissection at the L2 level above revealed a large "sinuvertebral nerve" nerve from immediately distal to the L2 ganglion, that coursed directly to the L3 basivertebral foramen; this nerve branched twice at the level of the L2-3 disc, sending small branches medially and laterally. The L2 nerve root also produced a "second sinuvertebral nerve" the coursed medially and centrally at the L2 level. This nerve was not explored further.

SUMMARY

Lumbar Spinal dissection was performed on a total of five cadavers with the successful approach as described. A total of 18 levels, ranging from L1 to S1 were bilaterally exposed. A total of 34 basivertebral nerves were successfully traced from their point of origin at the sinuvertebral nerve, beneath the posterior longitudinal ligament and to the point of entry into the basivertebral foramen. In every case, the innervation of the basivertebral foramen was traced to one or both (L, R) basivertebral nerve branches from the sinuvertebral nerve. In the majority of levels dissected (16118) basivertebral foramen innervations was clearly bilateral. The fragility of the branches of the sinuvertebral nerve has been noted by other authors. It is suspected that nerve breakage during dissection may have allowed some branches of the sinuvertebral nerve to have remained undetected. The typical anatomy is illustrated in FIG. 4, with variants as described illustrated in FIGS. 5 and 6. In all cases, the innervation of the vertebral body via the basivertebral foramen was from one or more medial branches of the large branch of the sinuvertebral nerve that was consistently seen coursing cephalad within the ventral epidural space.

Discussion

The paraspinal neuroanatomy (including innervation of the disc) has been extensively described. The innervation of the vertebral body has been documented as well. The neuroanatomical communication between paraspinal and intervertebral innervation and its implications has been less studied. In this study, emphasis was placed on the proximal basivertebral system, following the basivertebral nerve to its point of origin. As described above, the basivertebral nerve system originates as a medial branch of the sinuvertebral nerve.

The sinuvertebral nerve was specifically identified as a branch of the exiting lumbar nerve root. The sinuvertebral nerve was clearly seen to course back into the ventral epidural space, and usually was seen to branch into at least three easily identifiable branches.

In this study, the medial branches of the nerve were followed as they course underneath the posterior longitudinal ligament. The largest medial branches of the sinuvertebral nerve were seen to course under the posterior longitudinal ligament, and directly enter the basivertebral foramen. Such branches were seen at every level dissected. The basivertebral nerve was consistently present bilaterally.

Imaging and External Radiation of Basivertebral Nerve

Although the location of the basivertebral nerve is somewhat well known, the basivertebral nerve is a normally functioning anatomical feature that is radiolucent, so its precise location cannot be easily identified by an X-ray, angiography, or other indirect imaging methods. Since the basivertebral nerve may also be extremely thin in some embodiments, knowingly directing externally applied energy in close proximity to the basivertebral nerve, without risk to neighboring anatomy, may be problematic.

Several embodiments of the invention access the basivertebral nerve outside of the vertebral body, and denervate the basivertebral nerve to cut off or reduce conduction within the nerve (permanently or temporarily) to downstream locations within the vertebral body. Several embodiments of the invention predictably identify and treat the basivertebral nerve via an energy source located external to the skin (e.g., extracorporeal treatment) or external to the vertebral body of the patient (e.g., human or animal subject).

Several embodiments of the invention are directed to devices and methods for treating back pain by modulating (e.g., denervating, stimulating) the basivertebral nerve from an energy source located external to the body (e.g., external to the skin). While the embodiments listed below are directed to systems and methods that utilize radiation as the primary therapeutic energy modality, any type of energy capable of being directed to a focused point within the body of a patient (in one embodiment, preferably without destruction of intervening tissues and/anatomy) may be used (e.g., high-intensity or low-intensity focused ultrasound). The energy output may be dynamically controlled by changing the power intensity, the frequency, the angle of dispersion, the focus, or other dynamically controllable parameters. In some embodiments, radioactive implants may deliver energy instead of or in combination with external beam therapy.

For external therapy systems involving ultrasonic energy sources, the neuromodulating effects may include application of focused ultrasound energy to achieve sustained heating, sonication, and/or cavitation. In some embodiments, the focal intensity of the ultrasonic energy may range from about 100 W/cm2 to about 1 MW/cm2, from about 1 kW/cm2 to about 10 kW/cm2, from about 10 kW/cm2 to about 100 kW/cm2 or overlapping ranges thereof. In some embodiments, the frequency of the ultrasonic energy may range from about 500 kHz to about 10 MHz, from about 1 MHz to about 5 MHz, from about 5 MHz to about 10 MHz, or overlapping ranges thereof. In some embodiments, focused ultrasound energy may be selected to heat the tissue within the vertebral body to between about 35° C. and about 90° C., between about 40° C. and about 50° C., between about 45° C. and about 60° C., between about 50° C. and about 70° C., between about 60° C. and about 85° C., or overlapping ranges thereof. The treatment time may range from about 2 seconds to about 1 hour, from about 5 seconds to about 10 seconds, from about 10 seconds to about 30 seconds, from about 20 seconds to about 1 minute, from about 1 minute to about 5 minutes, from about 5 minutes to about 10 minutes, from about 10 minutes to about 20 minutes, from about 20 minutes to about 40 minutes, from about 30 minutes to about 45 minutes, from about 40 minutes to about 60 minutes, or overlapping ranges thereof.

Figure 19:
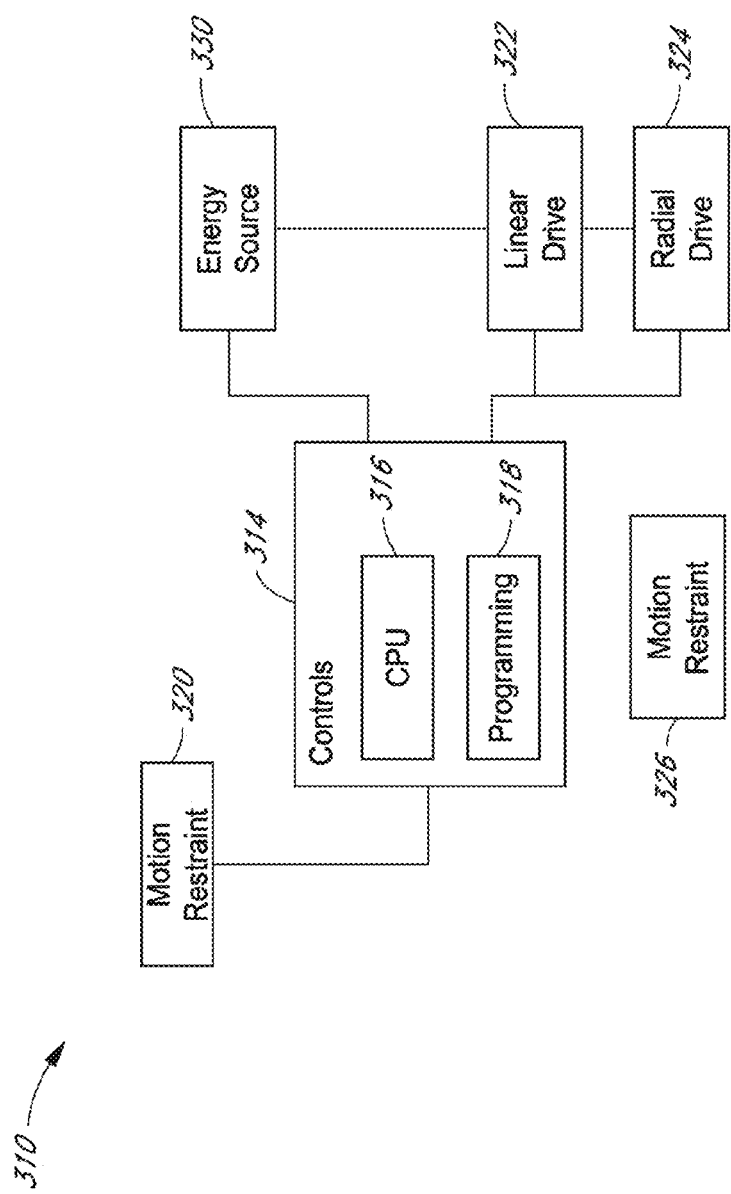
FIG. 19 is a block diagram of an embodiment of a radiotherapy apparatus for treating back pain.
Figure 20:
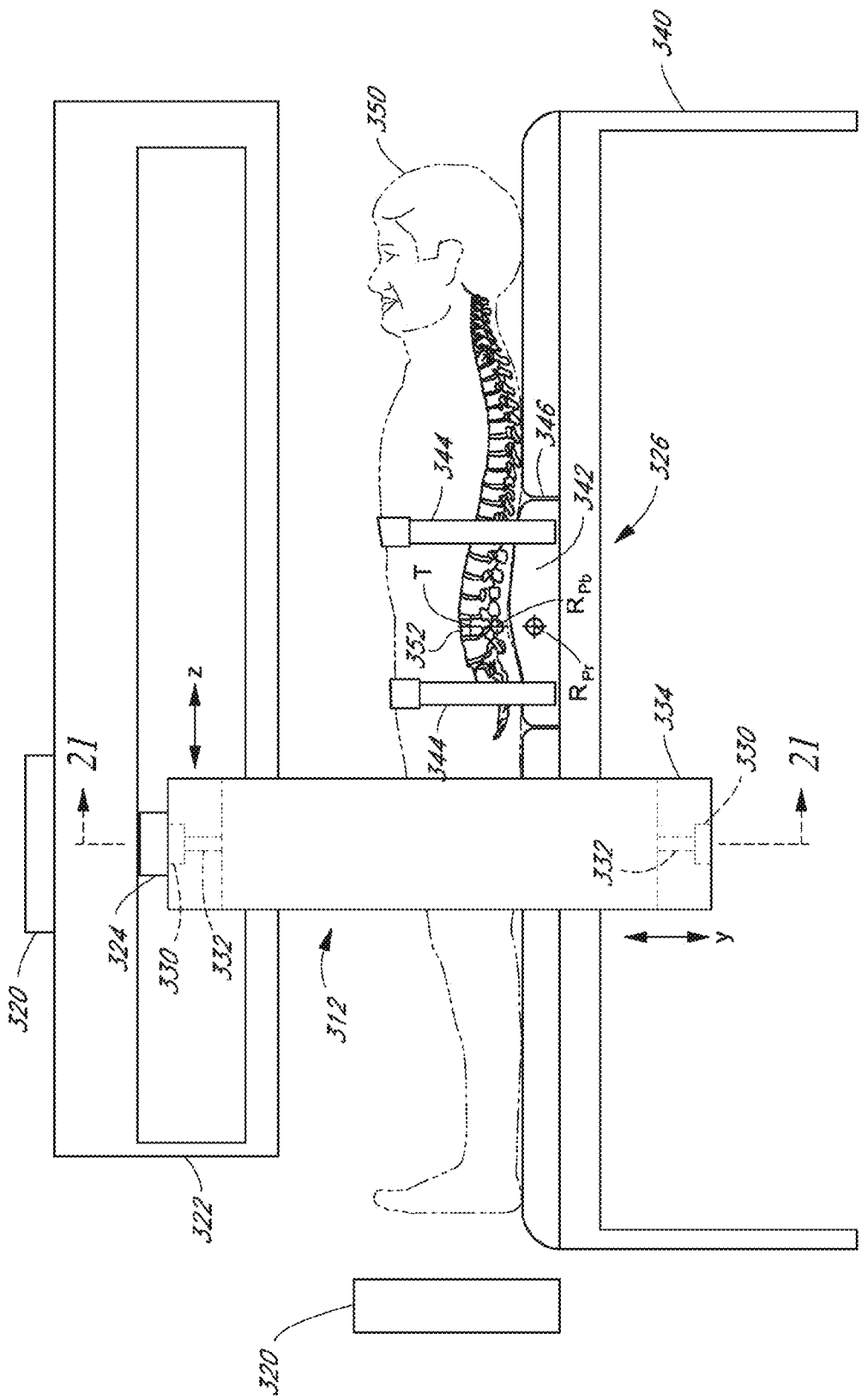
FIG. 20 is a schematic diagram of an embodiment of the radiotherapy apparatus of FIG. 19.
Figure 21:
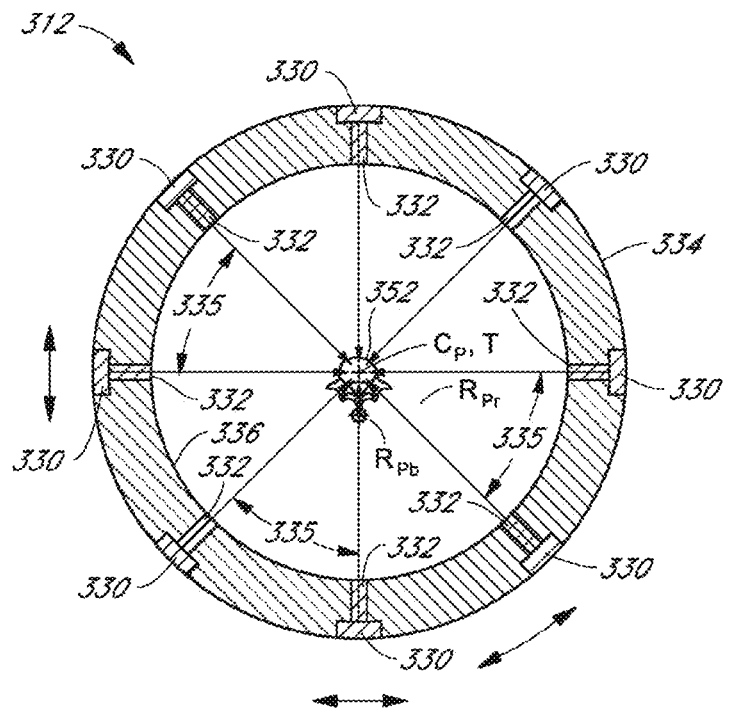
FIG. 21 is a sectional view of an embodiment of the radiotherapy gantry of FIG. 20.

FIGS. 19-21 detail the components of several embodiments of a radiotherapy system 310 configured to direct therapeutic energy to a region of the spine for purposes of modulating the basivertebral nerve. FIG. 19 illustrates a block diagram illustrating the primary components of radiotherapy system 310. FIG. 20 illustrates a schematic diagram of an example radiotherapy system 310 having a moveable gantry 312.

Referring to FIG. 19, one embodiment of an external therapy (e.g., radiotherapy) system 310 comprises a control module 314 (e.g., computer or series of computers) having a processor 316 and application programming modules 318 for controlling the delivery of energy from one or more energy sources 330. In some implementations, the control module 314 and application programming modules 318 are configured to control and monitor output from each energy source 330 to ensure proper dosing, while simultaneously controlling motion of the energy source 330 and gantry 312 through linear drive 322 and radial drive 324 to ensure the proper delivery location of therapeutic energy into the patient 350. The control module 314 and application programming modules 318 may also be configured to receive data (real-time or pre-acquired) from one or more imaging sources 320 (e.g., X-ray, CT, MRI, fluoroscopy, etc.). In some embodiments, external therapy (such as radiotherapy) system 310 further comprises a motion restraint 326 for immobilizing or minimizing motion of a particular spinal segment to be treated.

FIG. 20 illustrates a side view of one embodiment of a radiotherapy system 310 with a patient positioned for treatment. System 310 may include a table 340 that is fixed in relation to moveable gantry 312. In one embodiment, table 340 comprises a recess 346 sized to receive lumbar support 342 of motion restraint 326. Motion restraint 326 is shown in FIG. 20 as a lumbar restraint for immobilizing the lumbar spine segment from motion. However, motion restraint 326 may be configured with a support for immobilizing other regions of the spine (e.g. thoracic or cervical vertebrae). In some embodiments, motion restraint 326 comprises a plurality of straps 344 that wrap around the patient torso 350 for securing the support 342 to the patient's back adjacent to the lumber spine. In one embodiment, the motion restraint 326 is further configured to lock into the recess 346 so that the support 342 does not move with respect to the table 340.

In one embodiment, one or more radiation sources 330 are disposed in a moveable gantry 312 that is allowed to translate in (x, y, z) directions via linear drive 322. FIG. 21 shows a sectional view of one embodiment of the radiotherapy gantry 312. The gantry 312 comprises a tubular frame 334 configured to house one or more radiation sources 330. Each of the radiation sources may be embedded into the frame and configured to direct radiation energy through dedicated collimators 332 so as to focus the radiation beams 335 at the center-point of the gantry Cp.

In FIG. 21, the gantry 312 is shown centered about the target treatment site T (e.g., the center-point of the gantry Cp is shown coincident with the treatment target T). In some embodiments, imaging sources 320 are used (optionally in conjunction with images obtained from pre-acquired patient imaging) to help center the gantry 312 at the treatment location T (shown in FIG. 21 as the vertebral body 356 of L4 vertebra 352).

In accordance with several embodiments, gantry 312 is shown in FIG. 21 as housing eight radially spaced-apart radiation sources 330. However, the number of radiation sources 330 may vary from one to several hundred, depending on the type of radiation sources being used.

In accordance with several embodiments, in order to treat the basivertebral nerve of vertebral body 352, which is deep within the body of the patient, the radiation 335 penetrates the intervening healthy tissue in order to irradiate and modulate (e.g., denervate) the basivertebral nerve. In several embodiments, the treatment is performed without exposing large volumes of healthy tissue to harmful doses of radiation, thereby resulting in reduced recovery periods for the patient. In some embodiments, the patient is treated with ionizing radiation and treatment protocols so as to expose the target tissue to a dose of radiation that results in the desired cell modification, while keeping the exposure of healthy tissue to a minimum.

In order to avoid excessive doses being applied to healthy tissue, in some embodiments, the incident direction may be varied throughout the treatment period (e.g., by rotating gantry 312 with the various beams of radiation 335 each converging on a single point). Radial drive 324 may thus be employed to rotate the gantry 312 about the z-axis as shown in FIGS. 20 and 21.

In some embodiments, a large number of radiation sources 330 (e.g., from about 200 to about 300, from about 50 to about 100, from about 100 to about 200, overlapping ranges thereof, over 200) may be employed at a lower dose that individually have a negligible effect on intervening tissue. The single center point (Cp) may thereby receive a full dose, while the surrounding areas receive only a minimal dose. It is also possible to employ both a combination of multiple sources 330 and a rotating gantry 312.

Radiation sources 330 may comprise one of a number of different types, e.g., particle beam (proton beam therapy) sources, cobalt-60 based (photon or gamma-ray sources such as found in the Gamma Knife® technology), linear accelerator based (linac source such as that used in the CyberKnife® or Novalis® Tx technology). Gamma Knife® sources may produce gamma rays from the decay of Co-60 at an average energy of 1.25 MeV. The radiation sources 330 may include over 200 sources arrayed to deliver a variety of treatment angles. In some embodiments, linear accelerators emit high energy X-rays, usually referred to as "X-ray therapy" or "photon therapy." The x-rays are produced from the impact of accelerated electrons striking a high z target (usually tungsten). Linear accelerators therefore can generate any number of energy x-rays (e.g., 6 MV photons). For linear accelerators, the gantry generally moves in space to change the delivery angle.

Figure 22:
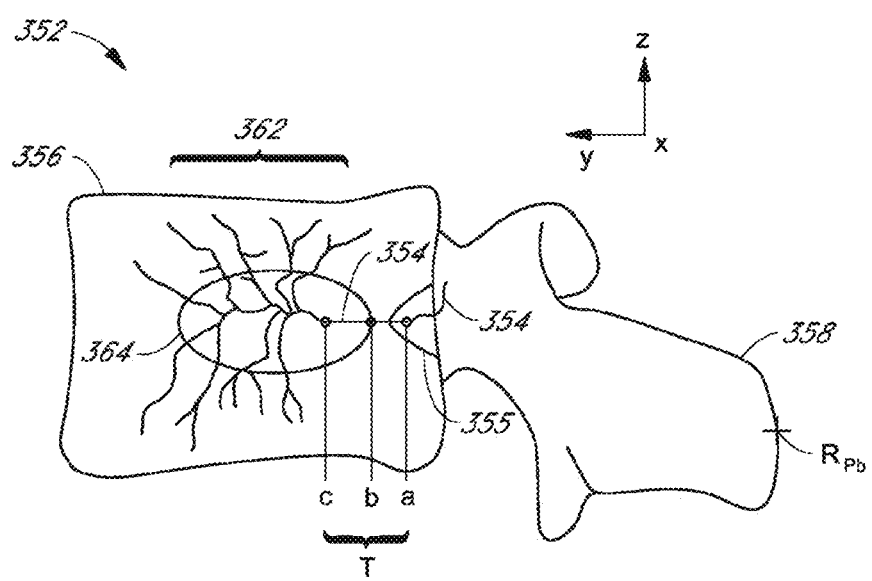
FIG. 22 is a side view of a lumbar vertebra showing innervation of the vertebral body.
Figure 23:
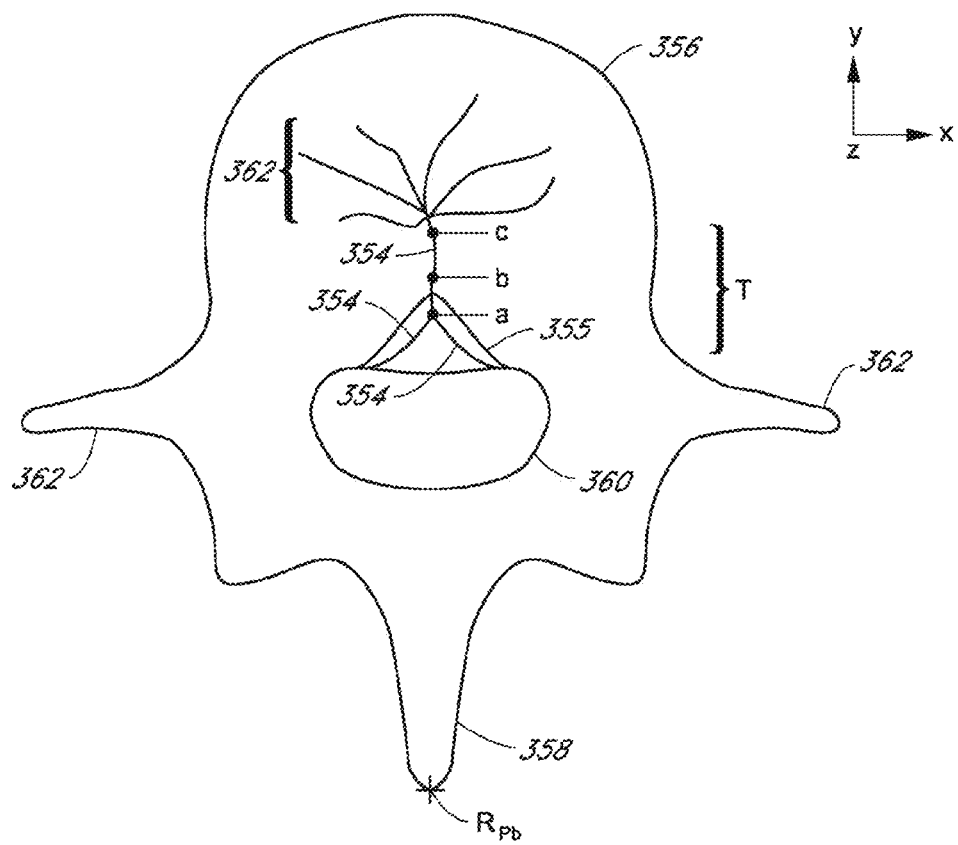
FIG. 23 is a top view of the lumber vertebra of FIG. 22.

Referring now to FIGS. 22 and 23, which illustrate the anatomy of a typical lumbar vertebra 352, the treatment target (e.g., basivertebral nerve) is a normally functioning anatomical feature that is radiolucent, so it generally cannot be seen or identified by an X-ray, angiography, or other indirect imaging methods. Accordingly, several embodiments of the invention use a novel approach for determining and verifying the target treatment site T.

FIGS. 22 and 23 illustrate side and top views, respectively, of a lumbar vertebra 312, showing vertebral body 356, and spinous process 358, in addition to the path 354 and plexus 362 of the basivertebral nerve. One or more basivertebral nerves 354 enter the vertebral body 356 through the basivertebral foramen 355, which is a conical opening emanating from the spinal canal 360, and generally penetrate the posterior cortex of the vertebral body 356 along the midline of the vertebral body 356. The basivertebral nerves 354 enter the vertebral body 356 at the basivertebral foramen 355, continue distally (anteriorly) through the vertebral body, and arborize at plexus 362 to innervate the vertebral body 356 down to and including the endplates In some embodiments, the target region T of the basivertebral nerve 354 is located within the cancellous portion of the bone (e.g., to the interior of the outer cortical bone region), and at or proximal to the junction or plexus 362 of the basivertebral nerve 354 having a plurality of branches. In some embodiments, treatment in this region (at or proximal to the junction or plexus 362) is advantageous because only a single portion of the basivertebral nerve 354 need be effectively treated to denervate (temporarily or permanently) the entire downstream nerve system. In contrast, treatment of the basivertebral nerve 354 at locations more downstream than the junction 362 may require the denervation of each individual branch.

Treatment in accordance with several embodiments of the invention can be effectuated by focusing energy 335 in the target region T of the vertebral body 356 located between 60% (point C) and 90% (point A) of the distance between the posterior and anterior ends of the vertebral body. Point A will often reside in the basivertebral foramen 355, and therefore energy directed to that region may not be as contained (basivertebral foramen 355 opens to the vertebral canal 360, containing sensitive anatomy such as the spinal chord) as when directed into the vertebral body at points B or C (which are surrounded at all sides by bone). Point C may run the risk of being downstream from the nerve junction.

In various embodiments, treatment can be effectuated by focusing in the region of the vertebral body located at a region that is more than 1 cm from the outer cortical wall of the vertebral body, within a region that is centered at or about 50% of the distance from the posterior outer cortical wall of the vertebral body to the anterior outer cortical wall, and/or within a region that is between 10% and 90% (e.g., between about 10% and about 60%, between about 20% and about 80%, between about 35% and about 65%, between about 25% and about 75%, between about 10% and about 55%, between about 30% and about 70%, or overlapping ranges thereof) of the distance from the posterior outer cortical wall of the vertebral body to the anterior outer cortical wall.

In accordance with several embodiments, because the basivertebral nerve is not visible from radiographic imaging, a radiographically identifiable reference point RPb may be advantageously established to determine a target treatment site T that corresponds with the correct location within the vertebral body. In FIGS. 20 through FIG. 24, reference point RPb is shown at the tip of the spinous process 358. Other physical landmarks may also be used without departing from the spirit and/or scope of the disclosure. The table 340 and/or motion restraint 326 may have a radiographically identifiable marker to establish external reference point RPr, which may be used for identifying the target T with respect to the treatment source 330 focal point/center point Cp.

Figure 24:
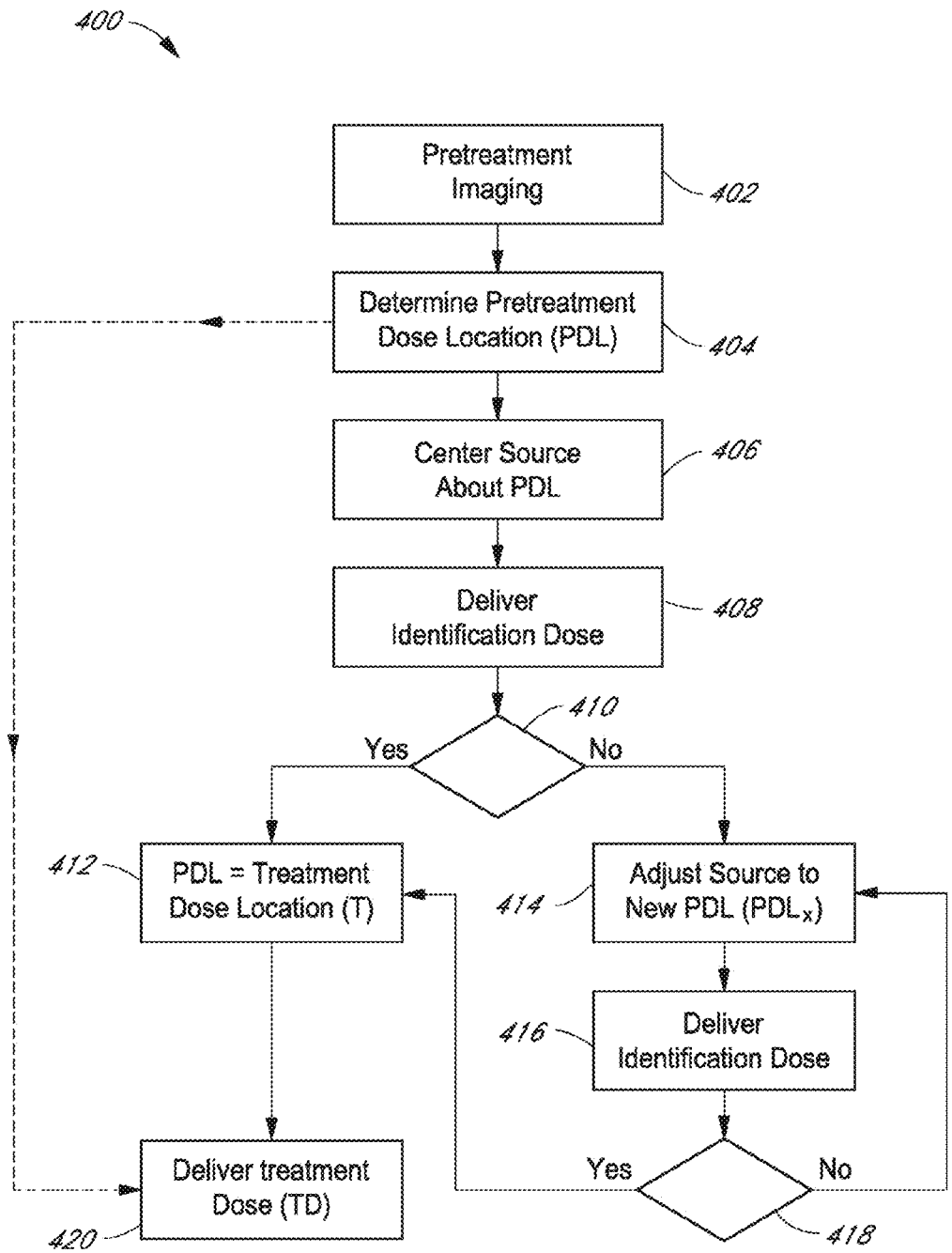
FIG. 24 is flow diagram of an embodiment of a radiotherapy method for treating back pain.

FIG. 24 illustrates a flow diagram of one embodiment of a method 400 for identifying and treating back pain through radiotherapy of the basivertebral nerve 354. In one embodiment, method 400 is carried out with use of radiotherapy system 31 O; however other external therapy/surgery systems may be used to perform method 400.

First, imaging data (also called image data) of the target anatomy (e.g., vertebra 352) is acquired at pretreatment imaging step 402. Image data (e.g. real-time or preacquired x-rays) may be obtained from one or more imaging sources 320, and/or from an outside imaging source (e.g., x-ray, CT, MRI, OCT, angiography, Doppler, ultrasound, etc.). The image data may be used to determine coordinates and dimensions of the target vertebra 312 used in acquiring or identifying the target location or treatments site T. In some embodiments, imaging is not performed. In some embodiments, imaging may be supplemented or replaced by non-imaging techniques that facilitate targeted treatment. In one embodiment, imaging is performed using the same system (e.g., transducer) that provides therapy.

In one embodiment, patient feedback may be obtained through a series of steps 404 through 418 to verify that source center point Cp is correctly positioned at the target treatment site T. In one embodiment, this verification is achieved by determining a pretreatment dose location (PDL) at step 404, which corresponds to the physician's (and/or other medical practitioner's) best estimate for the target basivertebral nerve location T, and delivering one or more identification doses. In another embodiment, the pretreatment dose location PDL is assumed to be the target location T, and the treatment dose TD is delivered at step 420, effectively skipping feedback steps 404 through 418.

In accordance with several embodiments, determining the pretreatment dose location PDL at step 404 generally involves analysis of data acquired from pretreatment imaging step 402. Reference points RPb and RPr (shown in FIGS. 20 through 23) may first be identified to aid in the determination of the treatment target. Once the reference point RPb on the target vertebra 352 is identified, the pretreatment dose location PDL corresponding to expected target T (Xt, Yt, Zt) may be set according to a calculated coordinate distance (e.g., corresponding to a predicted basivertebral nerve location) from the reference point RPb (Xr, Yr, Zr). For example, target T may be at coordinate (Xr+O, Yr+Yd, Zr+Zd), where distances Yd and Zd are computed based at least in part on the pre-acquired imaging data of the anatomy and one or more predetermined metrics. For example, distance Yd may be calculated according to the Y coordinate point corresponding to 75% of the distance from the anterior end of the vertebral body 356 to the posterior end of the vertebral body 356. Distance Zd may be calculated according to the Z coordinate point corresponding to a midline of vertebral body 356. Since the tip of the spinous process 358 generally corresponds to the X coordinate of the basivertebral nerve 354, the reference coordinate Xr will typically be equal to the target coordinate Xt. In some embodiments, reference RPr on table 340 may be used as the starting point from which motion of the gantry 312 is based to center the source 330 about the pretreatment dose location PDL (e.g., PDL=Cp).

In one embodiment, at step 408, an identification dose is delivered to the pretreatment dose location PDL. This identification dose is generally a fraction of the treatment dose TD, and may be prescribed to elicit some response from the patient relating to the patient's pain. At step 410, patient feedback is acquired to verify a change in the sensation of pain within the region. The patient's change in pain sensation may be positive (e.g., temporarily alleviate or lessen pain via numbing effect, etc.) or negative (e.g., the small dose aggravates the nerve ends, thereby causing more pain).

If no change in pain is experienced by the patient 350, the source 330 center point Cp may be adjusted to a new pretreatment dose location (PDLx) at step 414. In some embodiments, an additional identification dose is then delivered at step 416. Patient feedback is then elicited for some change in sensation relating to the patient's pain at step 418. If no change in pain is still experienced by the patient 350, the source 330 center point Cp may be adjusted to yet another pretreatment dose location (PDLx) at step 414. In some embodiments, the loop continues in a scanning fashion until the patient identifies a change in pain sensation, thus verifying that the target dose location T is the last treatment dose location (PDL) at step 412.

Next, in accordance with several embodiments, the treatment dose TD is delivered to the target T. Embodiments with radial drive 324 may be operated to change the delivery angle during treatment and minimize the dose to non-target tissues. The treatment dose TD is generally prescribed before treatment, and can be a factor of the patient's age, anatomy, desired treatment volume 364 (see FIG. 22), etc. In some embodiments, the treatment dose is configured to denervate the basivertebral nerve 354 to inhibit transmission of pain signals from within the vertebral body 356.

In one embodiment, the prescribed treatment dose is configured to deliver therapeutic treatment that is targeted to block nerve conduction without ablating the nerve, e.g., thermal treatment is delivered to the nerve that results in denervation of the basivertebral nerve 354 without necrosis of tissue. This denervation without ablation or necrosis may be achieved via delivery of a lesser amount of energy or agent to the tissue site (either in the form of less exposure time, concentration, intensity, etc.) than is required for ablation, but an amount sufficient to achieve some amount of temporary or permanent denervation.

In one embodiment, the treatment dose for delivery of gamma radiation delivered to the patient will typically range between 10 Gy and 70 Gy (e.g., between about 10 Gy and about 30 Gy, between about 20 Gy and about 50 Gy, between about 30 Gy and about 60 Gy, between about 40 Gy and about 70 Gy, or overlapping ranges thereof). However, because the treatment region is contained within the large bony mass vertebral body 356, higher doses may be contemplated, as there is little risk to surrounding tissues that are more vulnerable. The dose may be varied based on the treatment volume 364, or other variables, such as treatment time and dose concentration. A prescription of 35 instances of a 2 Gy dose might be replaced by 15 instances of a 3 Gy dose, a technique known as "hypofractionation." Taken to its logical extreme, this dose might be replaced with a single 45 Gy dose if the dosage delivered to healthy tissue can be reduced significantly.

In several embodiments, the identification dose used in steps 408 through 416 is generally a much smaller dose than treatment dose TD, so as not to damage healthy tissue. An example dose may range from 0.5 Gy to 5 Gy (e.g., between about 0.5 Gy and about 2 Gy, between about 1 Gy and about 2.5 Gy, between about 1.5 Gy and about 3 Gy, between about 2 Gy and about 5 Gy, or overlapping ranges thereof. However, this range may also change based on considerations such as anatomy, patient, etc.

In some embodiments, one or more radioactive implants are used to deliver radiotherapy instead of or in combination with external beam therapy. The one or more radioactive implants may be inductively powered or activated from outside the body over time (e.g., periodically or as desired or required). In some embodiments, the radioactive implants include an internal battery. The radioactive implants may deliver radioactive therapy over time without additional activation. The radioactive implants may be permanent or removable. In some embodiments, a radioactive implant comprises a plurality of radioactive sources or a plurality of radioactive seeds. In accordance with several embodiments, treatment time is subject to rate of radioactive decay of the radioactive implants. In some embodiments, the radiotherapy is delivered over a matter of minutes (e.g., 10 to 60 minutes, 20 to 40 minutes, 15 to 50 minutes, or overlapping ranges thereof), a matter of hours (e.g., 1 to 24 hours, 2 to 6 hours, 8-12 hours, or overlapping ranges thereof), a matter of days (e.g., 1 to 3 days, 2 to 8 days, 2 to 4 days, or overlapping ranges thereof), a matter of months (e.g., 1 to 12 months, 2 to 6 months, 4 to 10 months, 3 to 9 months, or overlapping ranges thereof), or a matter of years (e.g., 1 to 10 years, 2 to 6 years, 3 to 6 years, or overlapping ranges thereof).

Figure 25:
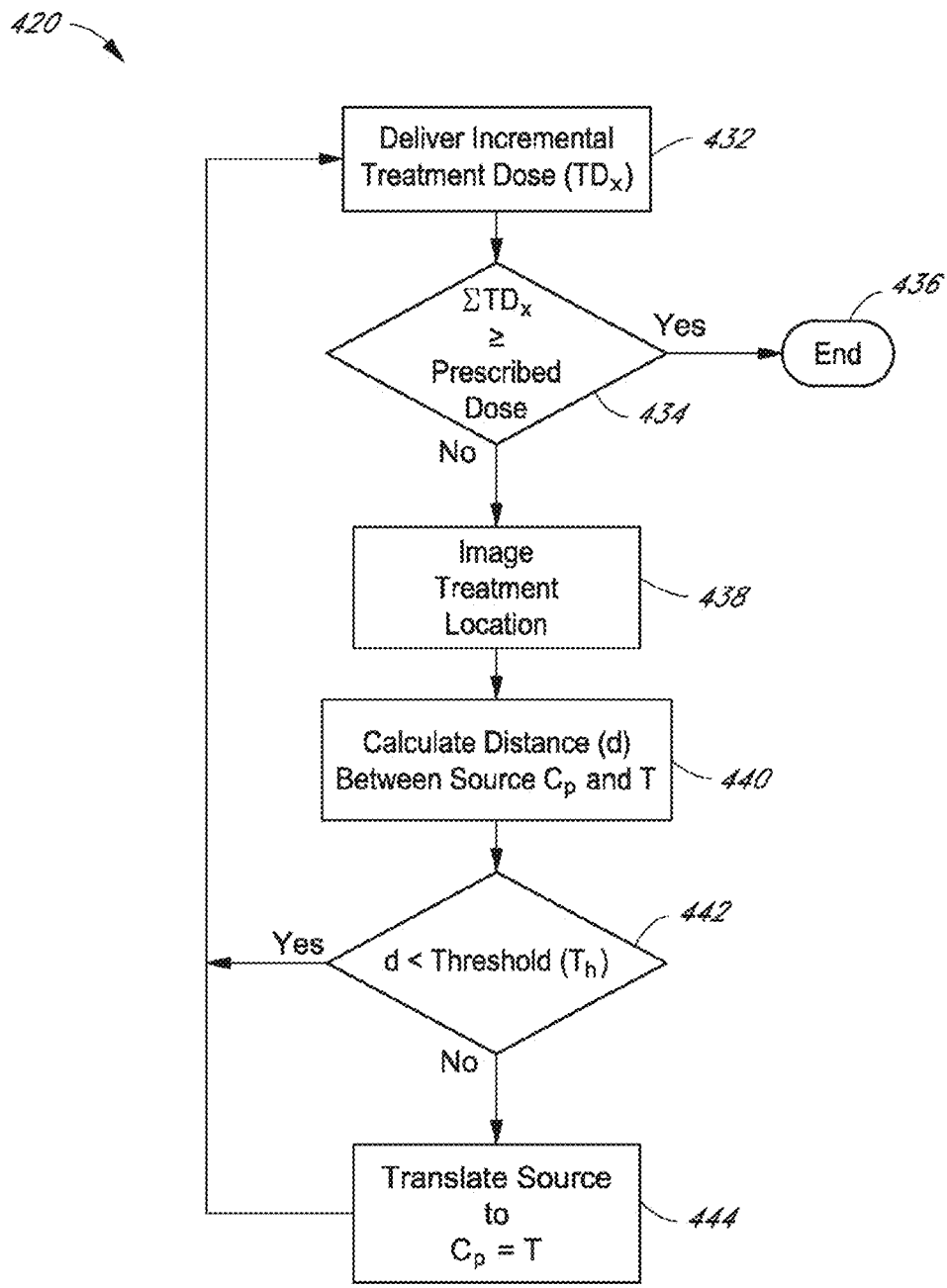
FIG. 25 is an embodiment of a flow diagram of the treatment delivery method of FIG. 24.

Referring now to FIG. 25, in one embodiment, the application programming modules 318 may be configured to acquire real-time imaging data from imaging sources 320 to provide a motion-driven delivery of the treatment dose at step 420. In some embodiments, this ensures that the source Cp is delivering the dose to the target T, even in the event of incidental patient motion. An incremental treatment dose (e.g., an amount TDx equal to total treatment dose TD divided by number of increments) is delivered at step 432. At step 434, the routine determines if the total prescribed dose TD has been delivered. If yes, the routine ends at step 436. If not, the treatment location is imaged with respect to table 340 or restraint support 342 at step 438 (e.g., vertebra reference point RPb with respect to reference point RPr). At step 440, the distanced between source center point Cp and newly acquired target T data is calculated. The distanced is then compared against a threshold value Th at step 442. The treatment dose TD may be adjusted according to the desired sensitivity of the system 400. If distance d is less than value Th, the routine returns back to step 432 to deliver another incremental dose TDx. If distance d is greater than value Th, the source 330 (e.g., via linear motion of gantry 312) is translated at step 444 such that CP=T, and then the routine returns back to step 432 to deliver another incremental dose TDx.

While motion tracking dosing routine 420 of FIG. 25 may be used in place of physical restraint 326, in accordance with several embodiments, it is generally preferred to use the motion tracking in combination with restraint 326 to ensure delivery of energy to the proper target location T.

Although the treatments and therapies were described with reference to intraosseous nerves (e.g., basivertebral nerves) within the spine, the disclosed methods and systems may be used to modulate (e.g., ablate, stimulate) nerves within other bones in other locations of the body.

Conditional language, for example, among others, "can," "could," "might," or "may," unless specifically stated otherwise, or otherwise understood within the context as used, is generally intended to convey that certain embodiments include, while other embodiments do not include, certain features, elements and/or steps.

Although certain embodiments and examples have been described herein, aspects of the methods and devices shown and described in the present disclosure may be differently combined and/or modified to form still further embodiments. Additionally, the methods described herein may be practiced using any device suitable for performing the recited steps. Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure (including the figures) herein of any particular feature, aspect, method, property, characteristic, quality, attribute, element, or the like in connection with various embodiments can be used in all other embodiments set forth herein.

For purposes of this disclosure, certain aspects, advantages, and novel features of the inventions are described herein. Embodiments embodied or carried out in a manner may achieve one advantage or group of advantages as taught herein without necessarily achieving other advantages. The headings used herein are merely provided to enhance readability and are not intended to limit the scope of the embodiments disclosed in a particular section to the features or elements disclosed in that section. The features or elements from one embodiment of the disclosure can be employed by other embodiments of the disclosure. For example, features described in one figure may be used in conjunction with embodiments illustrated in other figures.

Embodiments of the invention may be described with reference to flowchart illustrations of methods and systems according to embodiments of the invention, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

Although the description above contains many details, these should not be construed as limiting the scope of the invention but as merely providing illustrations of some of the embodiments of this invention. Therefore, it will be appreciated that the scope of the invention fully encompasses other embodiments which may become obvious to those skilled in the art, and that the scope of the invention is accordingly to be limited by nothing other than the appended claims, in which reference to an element in the singular is not intended to mean "one and only one" unless explicitly so stated, but rather "one or more."

What is claimed is:

1. A method for treating back pain of a body of a subject, the method comprising:

positioning a focal point of an external energy source to align with a portion of a nerve that travels within a vertebral body at a location outside the vertebral body, wherein the external energy source is positioned external to the body of the subject; and delivering a treatment dose of therapeutic energy sufficient to denervate the portion of the nerve.

2. The method of claim 1, wherein the therapeutic energy comprises radiation energy.

3. The method of claim 1, wherein the therapeutic energy comprises ultrasonic energy.

4. The method of claim 3, wherein the ultrasonic energy comprises high-intensity focused ultrasonic energy.

5. The method of claim 1, wherein the external energy source comprises a plurality of energy sources.

6. The method of claim 1, wherein the nerve is a branch of a sinuvertebral nerve.

7. The method of claim 1, wherein the vertebral body is of a lumbar vertebra.

8. The method of claim 1, wherein the vertebral body is of an S1 vertebra.

9. The method of claim 1, further comprising determining the focal point based on imaging.

10. A method for treating back pain of a subject, the method comprising:

positioning a focal point of an external energy source to align with a portion of a nerve that travels within a vertebral body at a location outside the vertebral body, wherein the external energy source is positioned external to a body of the subject; and delivering a treatment dose of therapeutic energy sufficient to permanently block conduction along the portion of the nerve.

11. The method of claim 10, wherein the therapeutic energy comprises radiation energy.

12. The method of claim 10 wherein the therapeutic energy comprises ultrasonic energy.

13. The method of claim 12, wherein the nerve travels through a basivertebral foramen of the vertebral body.

14. The method of claim 12, wherein the nerve is a branch of a sinuvertebral nerve.

15. The method of claim 12, wherein the vertebral body is of a lumbar vertebra.

16. The method of claim 12, wherein the vertebral body is of a sacral vertebra.

17. The method of claim 12, further comprising determining the focal point based on imaging.

18. A method for treating back pain of a subject, the method comprising:

positioning a focal point of an external energy source to align with a portion of a nerve that travels within a vertebral body through a basivertebral foramen, wherein the external energy source is positioned external to the body of the subject; and delivering a treatment dose of therapeutic energy sufficient to modulate the portion of the nerve.

19. The method of claim 18, wherein the treatment dose of therapeutic energy is sufficient to ablate the portion of the nerve.

20. The method of claim 18, wherein the nerve is a basivertebral nerve, and wherein the focal point is located at a location within the vertebral body.

* * * * *